(12) United States Patent
Chun et al.

(10) Patent No.: US 9,783,845 B2
(45) Date of Patent: Oct. 10, 2017

(54) DETECTION OF TARGET NUCLEIC ACID SEQUENCE BY PTO CLEAVAGE AND EXTENSION-DEPENDENT NON-HYBRIDIZATION ASSAY

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

(*) Notice: Subject to any disclaimer, the term of this patent is extended or adjusted under 35 U.S.C. 154(b) by 0 days.

(21) Appl. No.: 14/655,847

(22) PCT Filed: Dec. 27, 2013

(86) PCT No.: PCT/KR2013/012312
§ 371 (c)(1),
(2) Date: Jun. 26, 2015

(87) PCT Pub. No.: WO2014/104818
PCT Pub. Date: Jul. 3, 2014

(65) Prior Publication Data
US 2016/0060690 A1    Mar. 3, 2016

(30) Foreign Application Priority Data

Dec. 27, 2012 (KR) .................. 10-2012-0154834
Jan. 25, 2013 (KR) .................. 10-2013-0008580
Mar. 29, 2013 (KR) .................. 10-2013-0034670

(51) Int. Cl.
*C12Q 1/68* (2006.01)

(52) U.S. Cl.
CPC ......... *C12Q 1/6853* (2013.01); *C12Q 1/6816* (2013.01); *C12Q 1/6823* (2013.01); *C12Q 1/6834* (2013.01); *C12Q 1/6851* (2013.01)

(58) Field of Classification Search
None
See application file for complete search history.

(56) References Cited

U.S. PATENT DOCUMENTS

| | | |
|---|---|---|
| 5,210,015 A | 5/1993 | Gelfand et al. |
| 5,487,972 A | 1/1996 | Gelfand et al. |
| 5,538,848 A | 7/1996 | Livak et al. |
| 5,691,142 A | 11/1997 | Dahlberg et al. |
| 5,994,069 A | 11/1999 | Hall et al. |
| 6,326,145 B1 | 12/2001 | Whitcombe et al. |
| 6,893,819 B1 | 5/2005 | Sorge |
| 7,309,573 B2 | 12/2007 | Sorge |
| 7,381,532 B2 | 6/2008 | Sorge |
| 2008/0241838 A1 | 10/2008 | Scaboo et al. |
| 2009/0023151 A1 | 1/2009 | Dawson et al. |
| 2010/0129812 A1 | 5/2010 | Yoo |

FOREIGN PATENT DOCUMENTS

| | | |
|---|---|---|
| WO | 2005051967 A2 | 6/2005 |
| WO | 2012096523 A2 | 7/2012 |
| WO | 2012134195 A2 | 10/2012 |

OTHER PUBLICATIONS

Parashar, D., et al., Applications of real-time PCR Technology to mycobacterial research, Indian Journal of Medical Research, Oct. 2006, 124, 4; ProQuest Health & Medical Complete, pp. 385-398.
Bernard, P., et al., Homogeneous Amplification and Variant Detection by Fluorescent Hybridization Probes, Clinical Chemistry 46, No. 2, 2000, pp. 147-148.
Goel, G., et al., A Review, Molecular beacon: a multitask probe, Journal of Applied Microbiology, 2005, vol. 99, pp. 435-442.

*Primary Examiner* — James Martinell
(74) *Attorney, Agent, or Firm* — Gianna Julian-Arnold; Saul Ewing LLP

(57) ABSTRACT

The present invention relates to the detection of a target nucleic acid sequence by a PCE-NH (PTO Cleavage and Extension-Dependent Non-Hybridization) assay. The present invention adopts the occurrence of the inhibition of the hybridization between the HO with the CTO by the formation of the target-dependent extended duplex. Therefore, the present invention may detect target sequences even when the HO is not cleaved. In this regard, the design of the 5'-tagging portion of PTO, CTO and HO sequences may be readily performed and the conditions for reactions may be also easily established. In addition, the detection of the hybrid between the CTO and the HO may be performed in a different vessel from that for the extension of the CTO.

25 Claims, 28 Drawing Sheets

A. Probing and Tagging Oligonucleotide (PTO)

B. Capturing and Templating Oligonucleotide (CTO)

C. Hybridizing Oligonucleotide (HO)

A. Hybridization

B. Primer extension & Cleavage of PTO

C. Hybridization of PTO fragment to CTO & Extension

D. Melting analysis of CTO-HO hybrid

A. Hybridization

B. Primer extension & Cleavage of PTO

C. Hybridization of PTO fragment to CTO & Extension of PTO fragment and displacement or cleavage of HO

D. Melting analysis of CTO-HO hybrid

A. Hybridization

B. Primer extension & Cleavage of PTO

C. Hybridization of PTO fragment to CTO & Extension

Cleaved PTO                    Uncleaved PTO

D. Melting analysis of CTO-HO hybrid

Cleaved PTO                    Uncleaved PTO

A. Hybridization

B. Primer extension & Cleavage of PTO

C. Hybridization of PTO fragment to CTO & Extension

D. Melting analysis of CTO-HO hybrid

A. Hybridization

B. Primer extension & Cleavage of PTO

C. Hybridization of PTO fragment to CTO & Extension

D. Melting analysis of CTO-HO hybrid

A. Hybridization

B. Primer extension & Cleavage of PTO

C. Hybridization of PTO fragment to CTO & Extension

D. Melting analysis of CTO-HO hybrid

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension of PTO fragment and displacement or cleavage of HO

D. Hybridization of HO to CTO and Detection

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension of PTO fragment and displacement or cleavage of HO

D. Hybridization of HO to CTO and Detection

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension

Cleaved PTO                                   Uncleaved PTO

D. Hybridization of HO to CTO and Detection

Cleaved PTO                                   Uncleaved PTO

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension

D. Hybridization of HO to CTO and Detection

A. Hybridization

B. Primer extension & Cleavage of PTO

C. Hybridization of PTO fragment to CTO & Extension

D. Hybridization of HO to CTO and Detection

Syn-ES  0 pmole

Syn-ES  0.1 pmole

Syn-ES  0.5 pmole

Syn-ES  1 pmole

Syn-ES  2 pmole

Syn-ES  3 pmole

Fig. 19B

| Syn-ES [1] (pmole) | CTO [2] (pmole) | HO [3] (pmole) | Tm [4] (°C) | -d(RFU)/dT [5] |
|---|---|---|---|---|
| 0 | 1 | 1 | 57.0 | 192.12 |
| 0.1 | 1 | 1 | 57.0 | 180.68 |
| 0.5 | 1 | 1 | 57.0 | 92.49 |
| 1 | 1 | 1 | 57.0 | - |
| 2 | 1 | 1 | 57.0 | - |
| 3 | 1 | 1 | 57.0 | - |

[1] Syn-ES (Synthetic Extended strand) has a nucleotide sequence complementary to CTO forming a extended duplex.
[2] CTO (Capturing and Templating Oligonucleotide) is blocked with a carbon spacer at its 3'-end.
[3] HO (Hybridizing Oligonucleotide) has a fluorescent molecule at its 5'-end and a quencher molecule at its 3'-end.
[4] Tm represents melting temperature of the CTO-HO Hybrid.
[5] RFU represents relative fluorescence units.

Fig. 20A

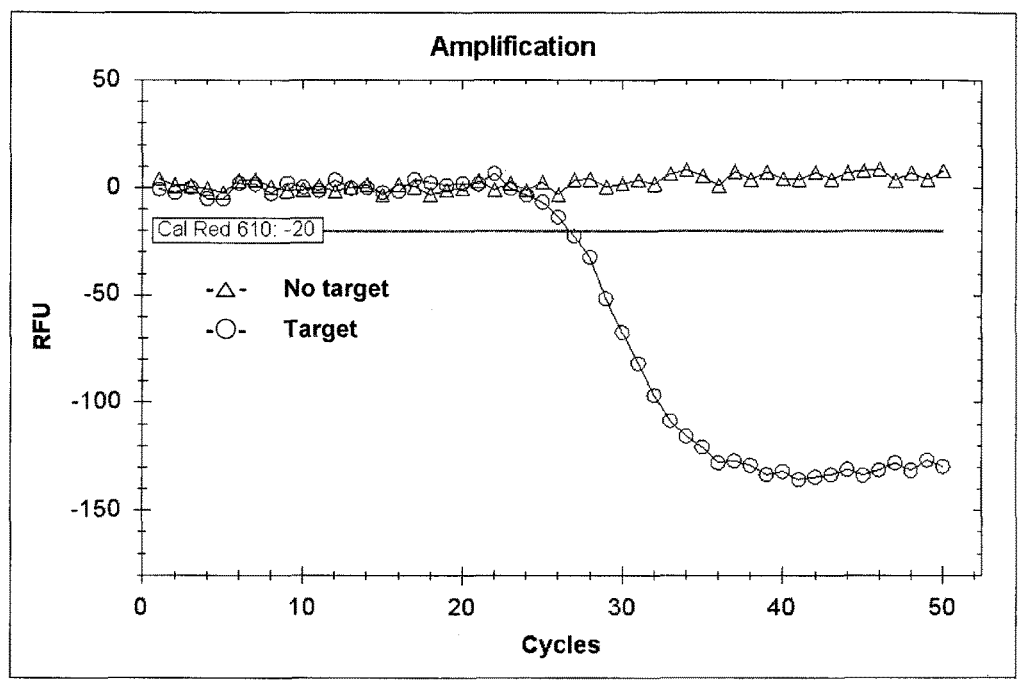

| Target [1] | Primer [2] | PTO [3] | CTO [4] | HO [5] | Ct |
|---|---|---|---|---|---|
| + | + | + | + | + | 26.0 |
| - | + | + | + | + | - |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] HO (Hybridizing Oligonucleotide) has a fluorescent molecule at its 5'-end and a quencher molecule at its 3'-end.

Fig. 20B

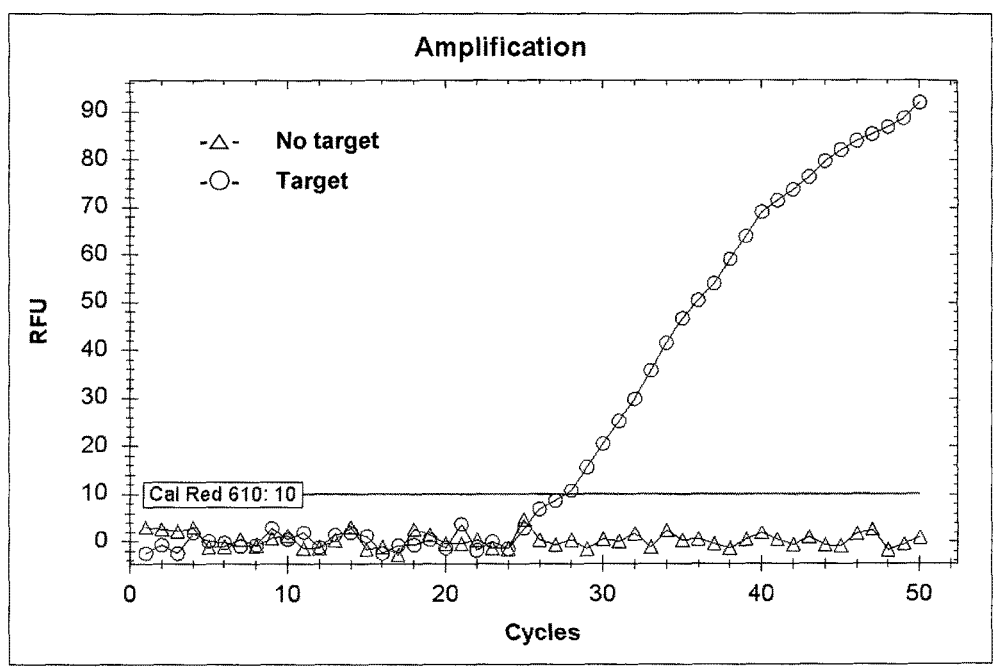

| Target [1] | Primer [2] | PTO [3] | CTO [4] | HO [5] | Ct |
|---|---|---|---|---|---|
| + | + | + | + | + | 27.6 |
| - | + | + | + | + | - |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] HO (Hybridizing Oligonucleotide) has a fluorescent molecule at its 5'-end and a quencher molecule at its 3'-end.

Fig. 20C

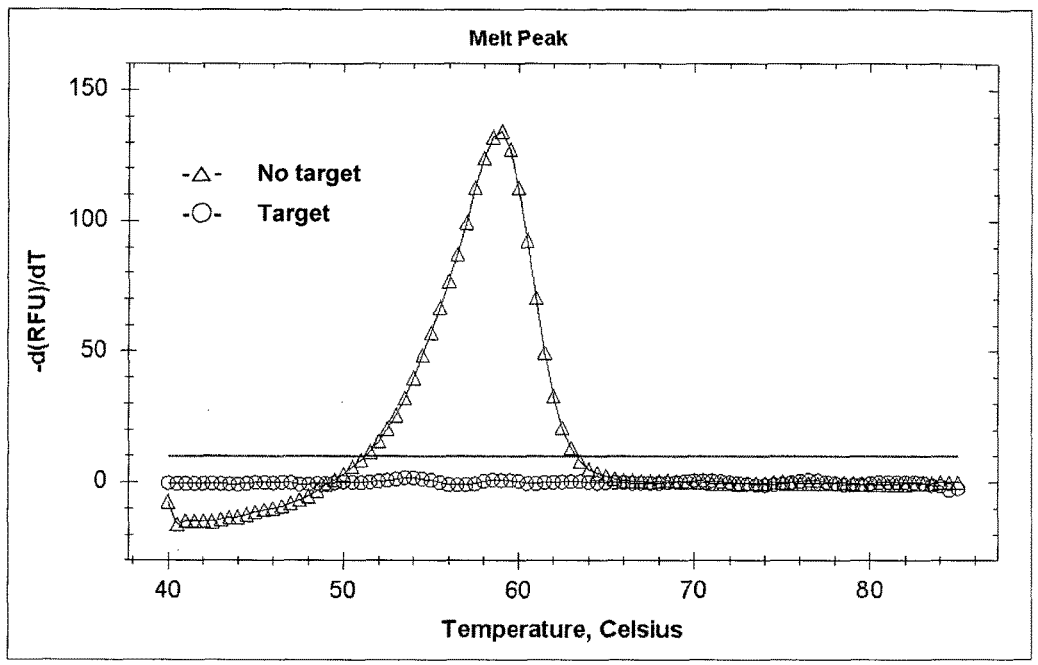

| Target [1] | Primer [2] | PTO [3] | CTO [4] | HO [5] | Tm [6] (℃) |
|---|---|---|---|---|---|
| + | + | + | + | + | - |
| - | + | + | + | + | 59.0 |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] HO (Hybridizing Oligonucleotide) has a fluorescent molecule at its 5'-end and a quencher molecule at its 3'-end.
[6] Tm represents the melting temperature of the CTO-HO Hybrid.

Fig. 21A

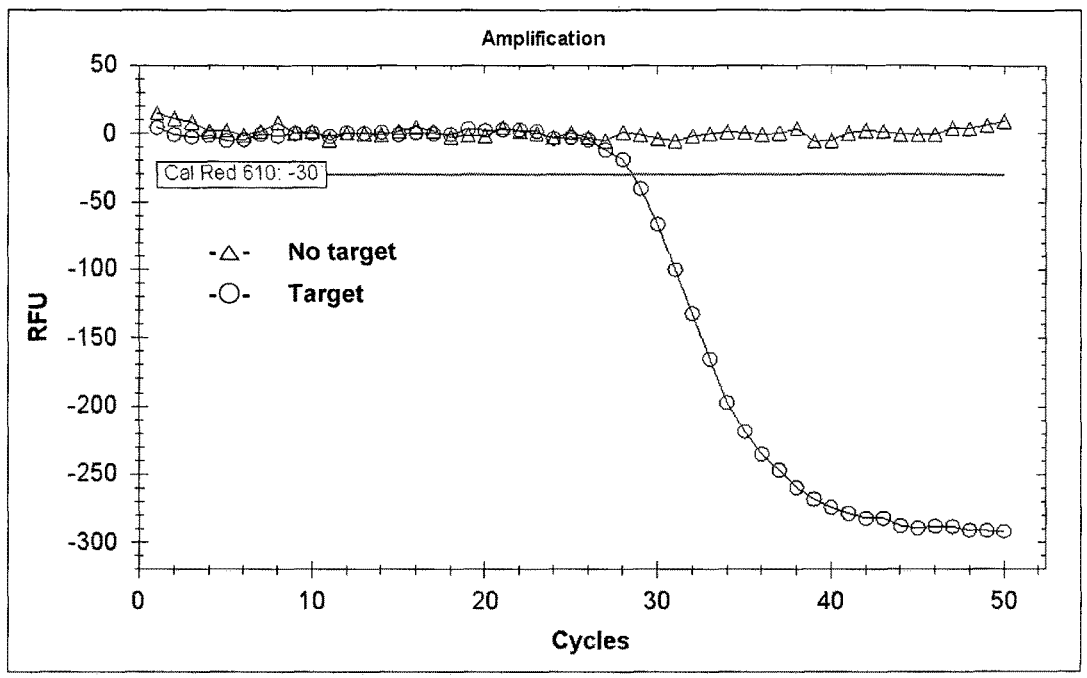

| Target [1] | Primer [2] | PTO [3] | CTO [4] | HO [5] | Ct |
|---|---|---|---|---|---|
| + | + | + | + | + | 28.2 |
| − | + | + | + | + | − |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] HO (Hybridizing Oligonucleotide) has a fluorescent molecule at its 5'-end and a quencher molecule at its 3'-end.

Fig. 21B

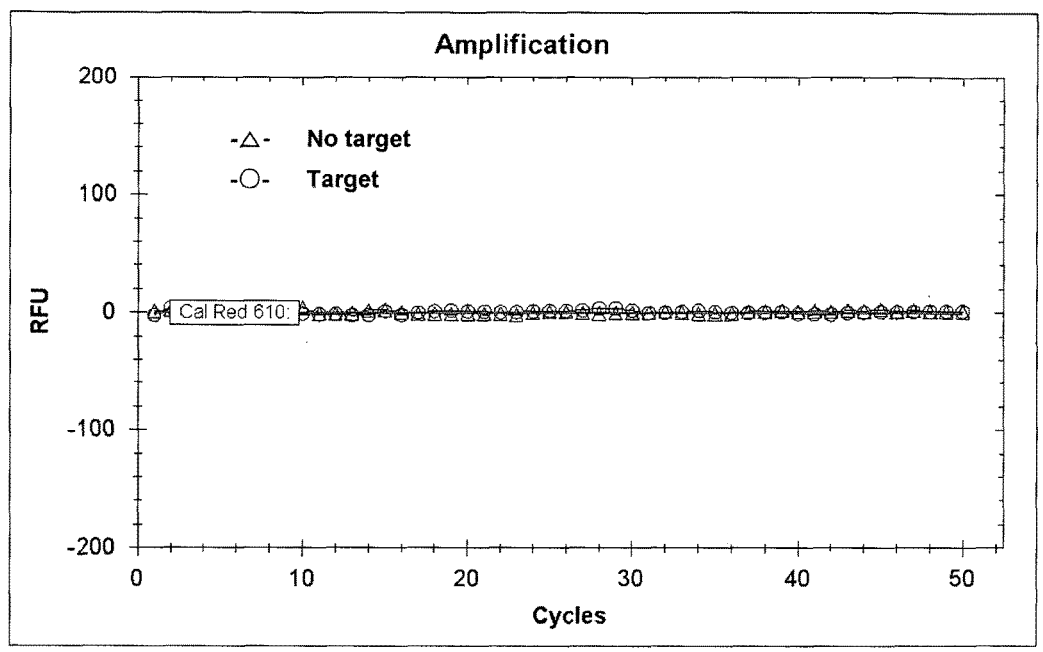

| Target [1] | Primer [2] | PTO [3] | CTO [4] | HO [5] | Ct |
|---|---|---|---|---|---|
| + | + | + | + | + | - |
| - | + | + | + | + | - |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] HO (Hybridizing Oligonucleotide) has a fluorescent molecule at its 5'-end and a quencher molecule at its 3'-end.

Fig. 21C

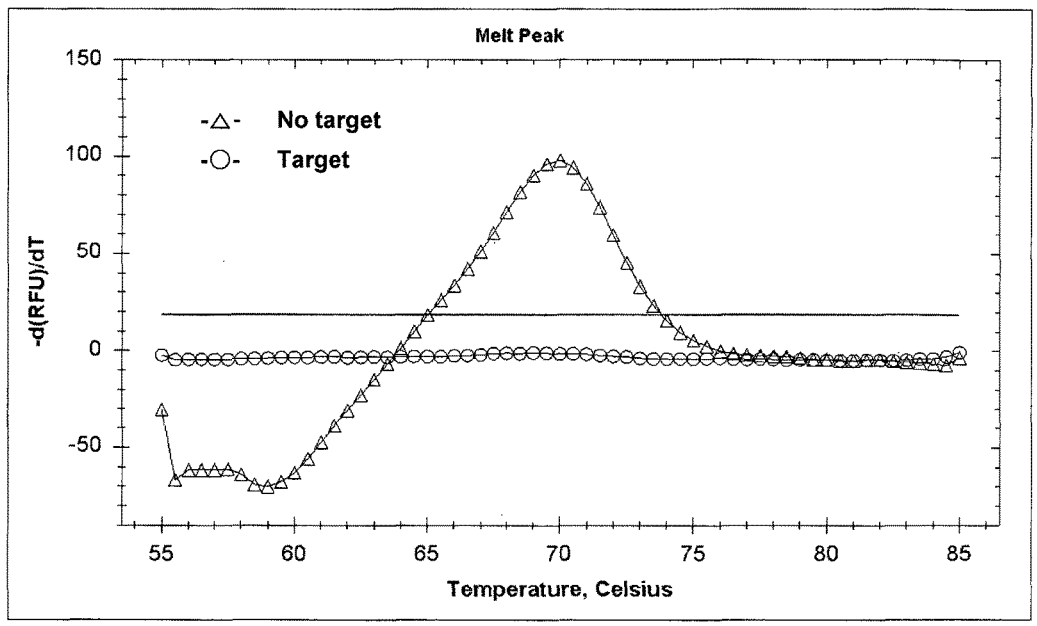

| Target [1] | Primer [2] | PTO [3] | CTO [4] | HO [5] | Tm [6] (℃) |
|---|---|---|---|---|---|
| + | + | + | + | + | - |
| - | + | + | + | + | 70.0 |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) is blocked with a carbon spacer at its 3'-end.
[5] HO (Hybridizing Oligonucleotide) has a fluorescent molecule at its 5'-end and a quencher molecule at its 3'-end.
[6] Tm represents the melting temperature of the CTO-HO Hybrid.

Fig. 22

A. Fluorescent image

No target      Target

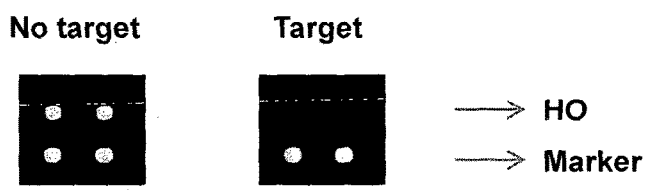

→ HO
→ Marker

B. Fluorescence intensity

| Target [1] | Primers [2] | PTO [3] | CTO [4] | RFU [5] |
|---|---|---|---|---|
| − | + | + | + | 65,441.5 (±2.1) |
| + | + | + | + | 829.5 (±58.7) |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) has a fluorescent molecule at its 3'-end.
[5] RFU represents relative fluorescence units.

Fig. 23

A. Fluorescent image

No target    Target

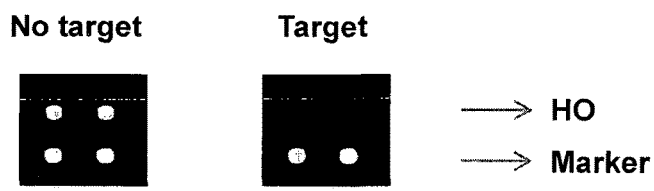

⟶ HO
⟶ Marker

B. Fluorescence intensity

| Target [1] | Primers [2] | PTO [3] | CTO [4] | RFU [5] |
|---|---|---|---|---|
| - | + | + | + | 65,467.5 (±0.7) |
| + | + | + | + | 34.5 (±2.1) |

[1] Target is genomic DNA of *Neisseria gonorrhoeae* gene.
[2] Primers are an upstream primer and a downstream primer for PCR.
[3] PTO (Probing and Tagging Oligonucleotide) is blocked with a carbon spacer at its 3'-end.
[4] CTO (Capturing and Templating Oligonucleotide) has a fluorescent molecule at its 3'-end.
[5] RFU represents relative fluorescence units.

SEQUENCE LISTING

<160> NUMBER OF SEQ ID NOS: 12

<210> SEQ ID NO 1
<211> LENGTH: 40
<212> TYPE: DNA
<213> ORGANISM: Artificial Sequence
<220> FEATURE:
<223> OTHER INFORMATION: Synthetic sequence

<400> SEQUENCE: 1
acgacggctt ggctgagcgc tggataccct ggacgatatg            40

<210> SEQ ID NO 2
<211> LENGTH: 40
<212> TYPE: DNA
<213> ORGANISM: Artificial Sequence
<220> FEATURE:
<223> OTHER INFORMATION: Synthetic sequence

<400> SEQUENCE: 2
catatcgtcc agggtatcca gcgctcagcc aagccgtcgt            40

<210> SEQ ID NO 3
<211> LENGTH: 15
<212> TYPE: DNA
<213> ORGANISM: Artificial Sequence
<220> FEATURE:
<223> OTHER INFORMATION: Synthetic sequence

<400> SEQUENCE: 3
gcgctggata ccctg            15

<210> SEQ ID NO 4
<211> LENGTH: 37
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (22)..(26)
<223> OTHER INFORMATION: n is a, c, g, or t

<400> SEQUENCE: 4
tacgcctgct actttcacgc tnnnnngtaa tcagatg            37

<210> SEQ ID NO 5
<211> LENGTH: 37
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (22)..(26)
<223> OTHER INFORMATION: n is a, c, g, or t

<400> SEQUENCE: 5
caatggatcg gtatcactcg cnnnnncgag caagaac            37

<210> SEQ ID NO 6
<211> LENGTH: 35
<212> TYPE: DNA
<213> ORGANISM: Artificial Sequence
<220> FEATURE:
<223> OTHER INFORMATION: Synthetic sequence

<400> SEQUENCE: 6

```
acgacggctt ggctgcccct cattggcgtg tttcg                                35
```

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence

<400> SEQUENCE: 7

```
tacgcctgct actttcacgc t                                               21
```

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8

```
caatggatcg gtatcactcg c                                               21
```

<210> SEQ ID NO 9
<211> LENGTH: 20
<212> TYPE: DNA
<213> ORGANISM: Artificial Sequence
<220> FEATURE:
<223> OTHER INFORMATION: Synthetic sequence

<400> SEQUENCE: 9

```
acgacggctt ggctgagcgc                                                 20
```

<210> SEQ ID NO 10
<211> LENGTH: 40
<212> TYPE: DNA
<213> ORGANISM: Artificial Sequence
<220> FEATURE:
<223> OTHER INFORMATION: Synthetic sequence

<400> SEQUENCE: 10

```
catatcgtcc agggtatcca gcgctcagcc aagccgtcgt                           40
```

<210> SEQ ID NO 11
<211> LENGTH: 34
<212> TYPE: DNA
<213> ORGANISM: Artificial Sequence
<220> FEATURE:
<223> OTHER INFORMATION: Synthetic sequence

<400> SEQUENCE: 11

```
gcgctggata ccctggacga tatgtttttt tttt                                 34
```

<210> SEQ ID NO 12
<211> LENGTH: 10
<212> TYPE: DNA
<213> ORGANISM: Artificial Sequence
<220> FEATURE:
<223> OTHER INFORMATION: Synthetic sequence

<400> SEQUENCE: 12

```
atatatatat                                                            10
```

DETECTION OF TARGET NUCLEIC ACID SEQUENCE BY PTO CLEAVAGE AND EXTENSION-DEPENDENT NON-HYBRIDIZATION ASSAY

CROSS-REFERENCE TO RELATED APPLICATIONS

This application claims the priority of PCT/KR2013/012312, filed on Dec. 27, 2013, which claims priority to Korean Patent Application No. 10-2012-0154834, filed Dec. 27, 2012, Korean Patent Application No. 10-2013-0008580, filed Jan. 25, 2013, and Korean Patent Application No. 10-2013-0034670, filed Mar. 29, 2013, the entire contents of each of which are hereby incorporated in total by reference.

SEQUENCE LISTING

This application incorporates by reference the Sequence Listing contained in an ASCII text file named "361406-00024_SeqList.txt" submitted via EFS-Web. The text file was created on Jun. 24, 2015, and is 3 kb in size.

BACKGROUND OF THE INVENTION

Field of the Invention

The present invention relates to the detection of a target nucleic acid sequence by a PCE-NH (PTO Cleavage and Extension-Dependent Non-Hybridization) assay.

Description of the Related Art

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis. However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected.

U.S. Pat. No. 7,309,573 disclose a method including formation of a released flap produced by a nucleic acid synthesis; extension of the released flap; cleavage of an oligonucleotide during extension of the flap and detection of a signal generated by the cleavage of the oligonucleotide.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences, in which target detection is accomplished by probe hybridization, enzymatic probe cleavage, extension and detection of extended product using HO (hybridizing oligonucleotide). The present protocols are well adopted to liquid phase reactions as well as solid phase reactions, and ensure detection of multiple target sequences with more improved accuracy and convenience.

Therefore, it is an object of this invention to provide a method for detecting a target nucleic acid sequence from a DNA or a mixture of nucleic acids by a PCE-NH (PTO Cleavage and Extension-Dependent Non-Hybridization) assay.

It is another object of this invention to provide a kit for detecting a target nucleic acid sequence from a DNA or a mixture of nucleic acids by a PCE-NH (PTO Cleavage and Extension-Dependent Non-Hybridization) assay.

Other objects and advantages of the present invention will become apparent from the detailed description to follow taken in conjugation with the appended claims and drawings.

BRIEF DESCRIPTION OF THE DRAWINGS

FIG. 2A illustrates hybridization; FIG. 2B illustrates primer extension and cleavage of PTO; FIG. 2C illustrates hybridization of PTO fragment to CTO and extension; and FIG. 2D illustrates melting analysis of CTO-HO hybrid. The HO has a reporter molecule and a quencher molecule. The formation of the extended duplex prevents the formation of the hybrid between the CTO and the HO by inhibition of the hybridization between the HO and the CTO.

FIG. 3A illustrates hybridization; FIG. 3B illustrates primer extension and cleavage of PTO; FIG. 3C illustrates hybridization of PTO fragment to CTO and extension of PTO fragment and displacement or cleavage of HO; FIG. 3D illustrates melting analysis of CTO-HO hybrid. The HO has a reporter molecule and a quencher molecule. The formation of the extended duplex prevents the formation of the hybrid between the CTO and the HO by cleavage of the HO as well as inhibition of the hybridization between the HO and the CTO.

FIG. 4A illustrates hybridization; FIG. 4B illustrates primer extension and cleavage of PTO; FIG. 4C illustrates hybridization of PTO fragment to CTO and extension; and FIG. 4D illustrates melting analysis of CTO-HO hybrid. The HO has a reporter molecule and the CTO has a quencher molecule.

FIG. 5A illustrates hybridization; FIG. 5B illustrates primer extension and cleavage of PTO; FIG. 5C illustrates hybridization of PTO fragment to CTO and extension; and FIG. 5D illustrates melting analysis of CTO-HO hybrid. The HO has a single fluorescence label to show different signal intensity depending on its presence on a single-strand or a double-strand.

FIG. 6A illustrates hybridization; FIG. 6B illustrates primer extension and cleavage of PTO; FIG. 6C illustrates hybridization of PTO fragment to CTO and extension; and FIG. 6D illustrates melting analysis of CTO-HO hybrid. The HO has a reporter molecule and a quencher molecule. The HO comprises a nucleotide sequence being competitive with the PTO fragment in terms of hybridization with the CTO.

FIG. 7A illustrates hybridization; FIG. 7B illustrates primer extension and cleavage of PTO; FIG. 7C illustrates hybridization of PTO fragment to CTO and extension; and FIG. 7D illustrates melting analysis of CTO-HO hybrid. The HO has a reporter molecule and the CTO has a quencher molecule. The HO comprises a nucleotide sequence being competitive with the PTO fragment in terms of hybridization with the CTO.

FIG. 8A illustrates hybridization; FIG. 8B illustrates primer extension and cleavage of PTO; FIG. 8C illustrates hybridization of PTO fragment to CTO and extension; and FIG. 8D illustrates hybridization of HO to CTO and Detection. The CTO has a single label and the HO is immobilized on a solid substrate. The formation of the extended duplex prevents the formation of the hybrid between the CTO and the HO by inhibition of the hybridization between the HO and the CTO.

FIG. 9A illustrates hybridization; FIG. 9B illustrates primer extension and cleavage of PTO; FIG. 9C illustrates hybridization of PTO fragment to CTO and extension of PTO fragment and displacement or cleavage of HO; and FIG. 9D illustrates hybridization of HO to CTO and Detection. The CTO has a single label and the HO is immobilized on a solid substrate. The formation of the extended duplex prevents the formation of the hybrid between the CTO and the HO by cleavage or displacement of the HO as well as inhibition of the hybridization between the HO and the CTO.

FIG. 10A illustrates hybridization; FIG. 10B illustrates primer extension and cleavage of PTO; FIG. 10C illustrates hybridization of PTO fragment to CTO and extension; and FIG. 10D illustrates hybridization of HO to CTO and Detection. The HO has a single label and the CTO is immobilized on a solid substrate. The formation of the extended duplex prevents the formation of the hybrid between the CTO and the HO by inhibition of the hybridization between the HO and the CTO.

FIG. 11A illustrates hybridization; FIG. 11B illustrates primer extension and cleavage of PTO; FIG. 11C illustrates hybridization of PTO fragment to CTO and extension of PTO fragment and displacement or cleavage of HO; and FIG. 11D illustrates hybridization of HO to CTO and Detection. The HO has a single label and the CTO is immobilized on a solid substrate. The formation of the extended duplex prevents the formation of the hybrid between the CTO and the HO by cleavage or displacement of the HO as well as inhibition of the hybridization between the HO and the CTO.

FIG. 12A illustrates hybridization; FIG. 12B illustrates primer extension and cleavage of PTO; FIG. 12C illustrates hybridization of PTO fragment to CTO and extension; and FIG. 12D illustrates hybridization of HO to CTO and Detection. The CTO has a single label and the HO is immobilized on a solid substrate. The HO comprises a nucleotide sequence being competitive with the PTO fragment in terms of hybridization with the CTO.

FIG. 13A illustrates hybridization; FIG. 13B illustrates primer extension and cleavage of PTO; FIG. 13C illustrates hybridization of PTO fragment to CTO and extension; and FIG. 13D illustrates hybridization of HO to CTO and Detection. The HO has a single label and the CTO is immobilized on a solid substrate. The HO comprises a nucleotide sequence being competitive with the PTO fragment in terms of hybridization with the CTO.

FIG. 14A illustrates hybridization; FIG. 14B illustrates primer extension and cleavage of PTO; FIG. 14C illustrates hybridization of PTO fragment to CTO and extension; and FIG. 14D illustrates hybridization of HO to CTO and Detection. The HO has a reporter molecule and a quencher molecule.

FIG. 15A illustrates hybridization; FIG. 15B illustrates primer extension and cleavage of PTO; FIG. 15C illustrates hybridization of PTO fragment to CTO and extension; and FIG. 15D illustrates hybridization of HO to CTO and Detection. The HO has a reporter molecule and the CTO has a quencher molecule.

FIG. 16A illustrates hybridization; FIG. 16B illustrates primer extension and cleavage of PTO; FIG. 16C illustrates hybridization of PTO fragment to CTO and extension; and FIG. 16D illustrates hybridization of HO to CTO and Detection. The HO has a single fluorescence label to show different signal intensity depending on its presence on a single-strand or a double-strand.

FIG. 17A illustrates hybridization; FIG. 17B illustrates primer extension and cleavage of PTO; FIG. 17C illustrates hybridization of PTO fragment to CTO and extension; and FIG. 17D illustrates hybridization of HO to CTO and Detection. The HO has a reporter molecule and a quencher molecule. The HO comprises a nucleotide sequence being competitive with the PTO fragment in terms of hybridization with the CTO.

FIG. 18A illustrates hybridization; FIG. 18B illustrates primer extension and cleavage of PTO; FIG. 18C illustrates hybridization of PTO fragment to CTO and extension; and FIG. 18D illustrates hybridization of HO to CTO and Detection. The HO has a reporter molecule and the CTO has a quencher molecule. The HO comprises a nucleotide sequence being competitive with the PTO fragment in terms of hybridization with the CTO.

FIGS. 19A and 19B represent results to evaluate whether the hybridization of HO to CTO is inhibited by the extended duplex. Syn-Es denotes synthetic extended strands.

FIG. 20A represents results of target detection by the PCE-NH assay in a real-time manner at a pre-determined temperature (hybridization temp. 55° C.). The results address a target detection using signals from the inhibition by the extended duplex.

FIG. 20B represents results of target detection by the PCE-NH assay in a real-time manner at a pre-determined temperature (denaturation temp. 95° C.). This result shows that some HOs can be cleaved during the reaction.

FIG. 20C represents results of target detection by the PCE-NH assay in a melting analysis manner.

FIG. 21A represents results of target detection by the PCE-NH assay in a real-time manner at a pre-determined temperature (hybridization temp. 60° C.). The HO comprises a nucleotide sequence being competitive with the PTO fragment in terms of hybridization with the CTO. The signal detected is provided from the inhibition of the hybridization between the HO and the CTO. The signal provided from the cleavage of HO is excluded.

FIG. 21B represents results of target detection by the PCE-NH assay in a real-time manner at a pre-determined temperature (denaturation temp. 95° C.). The HO comprises a nucleotide sequence being competitive with the PTO fragment in terms of hybridization with the CTO. This result shows that the HOs were not cleaved during the reaction.

FIG. 21C represents results of target detection by the PCE-NH assay in a melting analysis manner. The HO comprises a nucleotide sequence being competitive with the PTO fragment in terms of hybridization with the CTO.

FIG. 22 represents results of target detection by the PCE-NH assay using a single-labeled CTO and an immobilized HO on a solid phase.

FIG. 23 represents results of target detection by the PCE-NH assay using a single-labeled CTO and an immobilized HO on a solid phase in which the extension step and HO hybridization step were performed in separated tubes and the HO did not undergo cleavage.

DETAILED DESCRIPTION OF THIS INVENTION

Figure 1:
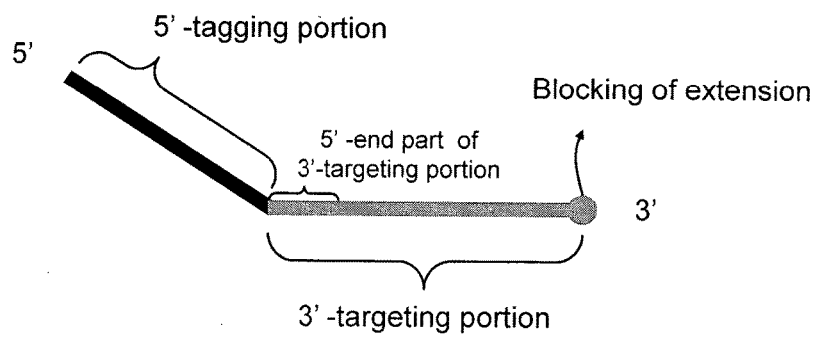
FIG. 1A shows the schematic structures of PTO (Probing and Tagging Oligonucleotide)
FIG. 1B shows CTO (Capturing and Templating Oligonucleotide) and FIG. 1C shows HO (hybridizing oligonucleotide) each as used in a PCE-NH (PTO Cleavage and Extension-Dependent Non-Hybridization) assay. Particularly, the 3'-ends of the PTO, CTO and HO are blocked to prohibit their extension.
Figure 1:
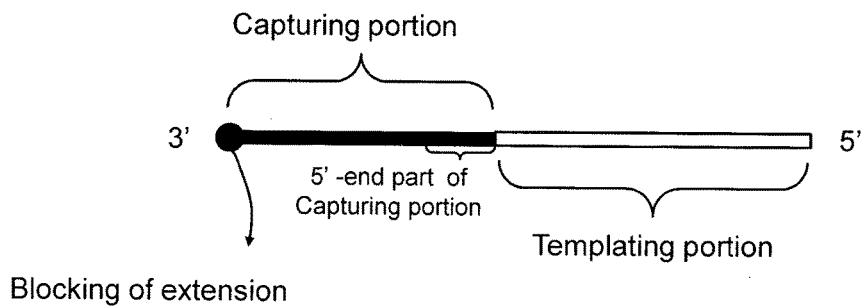
Figure 1:
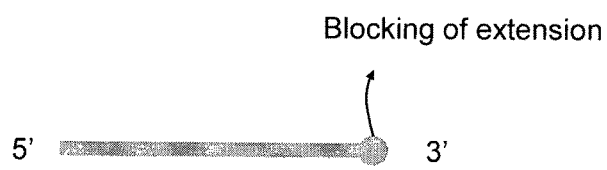

The present invention is directed to a novel method for detecting a target nucleic acid sequence by a PCE-NH (PTO Cleavage and Extension-Dependent Non-Hybridization) assay and a kit for detecting a target nucleic acid sequence by a PCE-NH assay. The present invention is performed by probe hybridization, enzymatic probe cleavage, extension and detection of extended product using HO (hybridizing oligonucleotide). The present invention can be classified into three aspects by fashions for the detection of extended product using HO.

I. First Aspect of Target Detection Process by a PCE-NH Assay

In one aspect of the present invention, there is provided a method for detecting a target nucleic acid sequence in a nucleic acid sample by a PCE-NH (PTO Cleavage and Extension-Dependent Non-Hybridization) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) performing a melting analysis or a hybridization analysis for the resultant of the step (d) over a range of temperatures with a HO (hybridizing oligonucleotide) comprising a hybridizing nucleotide sequence complementary to the CTO; wherein when the target nucleic acid sequence is not present in the nucleic acid sample, the extended duplex is not formed and the CTO and the HO form a hybrid, thereby providing a signal indicative of the presence of the hybrid between the CTO and the HO; wherein when the target nucleic acid sequence is present in the nucleic acid sample, the extended duplex is formed to prevent the formation of the hybrid between the CTO and the HO, thereby not providing the signal; wherein the signal is provided by (i) a label linked to the HO, (ii) a label linked to the CTO, (iii) a label linked to the HO and a label linked to the CTO, or (iv) an intercalating label; and (f) detecting the signal indicative of the presence of the hybrid between the CTO and the HO; wherein the presence of the hybrid between the CTO and the HO indicates the absence of the target nucleic acid sequence; wherein the absence of the hybrid between the CTO and the HO indicates the presence of the target nucleic acid sequence.

The present inventors have made intensive researches to develop novel approaches to detect target sequences with more improved accuracy and convenience, inter alia, in a multiplex manner. As a result, we have established novel protocols for detection of target sequences in which target detection is accomplished by probe hybridization, enzymatic probe cleavage, extension and melting analysis (or hybridization analysis) using the HO (hybridizing oligonucleotide). The present protocols are well adopted to liquid phase reactions as well as solid phase reactions, and ensure detection of multiple target sequences with more improved accuracy and convenience.

The present invention employs successive events including probe hybridization; cleavage of the PTO (Probing and Tagging Oligonucleotide) and extension; formation of an extended duplex; and melting analysis or a hybridization analysis using the HO. In the melting analysis or a hybridization analysis, no formation of the hybrid with the HO indicates the presence of a target nucleic acid sequence. Therefore, it is named as a PCE-NH (PTO Cleavage and Extension-Dependent Non-Hybridization) assay.

As the extended duplex is formed to prevent the formation of the hybrid between the CTO and the HO only if the target nucleic acid exists, no signal indicative of the presence of the hybrid between the CTO indicates the presence of the target nucleic acid.

The term "prevent the formation of the hybrid between the CTO and the HO" with referring to the extended duplex means all events relating to non-formation of the hybrid between the CTO and the HO by the extended duplex. For example, the term includes inhibition of the hybridization between the HO and the CTO by the extended duplex, and cleavage of the HO (i.e., cleavage of the HO during the extension of the PTO fragment) resulting in consumption of HO to form the hybrid.

The present invention is characterized by the use of $T_m$ value of the CTO/HO hybrid as a discrimination factor for detection of the presence or absence of CTO/HO hybrid. The CTO/HO hybrid has its distinguishable $T_m$ value being dependent on a sequence and/or length of the CTO and the HO. By a melting analysis or a hybridization analysis, the presence or absence of the CTO/HO hybrid is determined based on its $T_m$ value.

In particular, the present invention is applicable to detect a target nucleic acid sequence even when the HO is not cleaved (i.e., the hybridization between the HO and the CTO is inhibited by the formation of the extended duplex) as well as when the HO is cleaved.

Conventional technologies with signal generation from probes hybridized with target sequences and then cleaved may not give a melting curve. Unlikely, the present invention uses extinguishment (or decrease) of melting signals provided the hybrid between the CTO and the HO whose sequences are irrelevant to sequences of targets. Therefore, the present invention may detect target sequences by melting analysis even when the HO is cleaved dependent on the presence of target sequences.

The first aspect of the PCE-NH assay comprising melting or hybridization analysis will be described in more detail as follows:

Step (a): Hybridization of an Upstream Oligonucleotide and a PTO with a Target Nucleic Acid Sequence According to the present invention, a target nucleic acid sequence is first hybridized with an upstream oligonucleotide and a PTO (Probing and Tagging Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

In a certain embodiment, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is suitable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", for instance, perfectly complementary.

The 5'-tagging portion of the PTO comprises a nucleotide sequence non-complementary to the target nucleic acid sequence. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", for instance, perfectly non-complementary.

For example, the term "non-complementary" in conjunction with the 5'-tagging portion of the PTO means that the 5'-tagging portion is sufficiently non-complementary not to hybridize selectively to a target nucleic acid sequence under the designated annealing conditions or stringent conditions, encompassing the terms "substantially non-complementary" and "perfectly non-complementary", for instance, perfectly non-complementary.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 1.

In an embodiment, the hybridization in step (a) is preformed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the capturing portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. In certain embodiment, the 3'-end of the PTO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to an embodiment of this invention, the 5'-tagging portion of the PTO not involved in the hybridization with the target nucleic acid sequence forms a single-strand.

The upstream oligonucleotide is located upstream of the PTO.

In addition, the upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to an embodiment, the upstream oligonucleotide is located distantly to the PTO sufficient to induce the PTO cleavage in an extension-dependent manner.

According to an embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO. In certain embodiment, the overlapped sequence is 1-10 nucleotides, 1-5 nucleotides or 1-3 nucleotides in length. Where the upstream oligonucleotide has a partial-overlapped sequence with the 5'-part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to an embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to an embodiment, the method is performed in the presence of a downstream primer. The downstream primer generates additionally a target nucleic acid sequence to be hybridized with the PTO, enhancing sensitivity in target detection.

According to an embodiment, when the upstream primer and the downstream primer are used, a template-dependent nucleic acid polymerase is additionally employed for extension of the primers.

According to an embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40(2007)).

According to an embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041).

Step (b): Release of a Fragment from the PTO Cleavage

Afterwards, the resultant of the step (a) is contacted to an enzyme having a 5' nuclease activity under conditions for cleavage of the PTO. The PTO hybridized with the target nucleic acid sequence is digested by the enzyme having the 5' nuclease activity to release a fragment comprising the 5'-tagging portion or a part of the 5'-tagging portion of the PTO.

The term used herein "conditions for cleavage of the PTO" means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, $MgCl_2$ and temperature.

Figure 2:
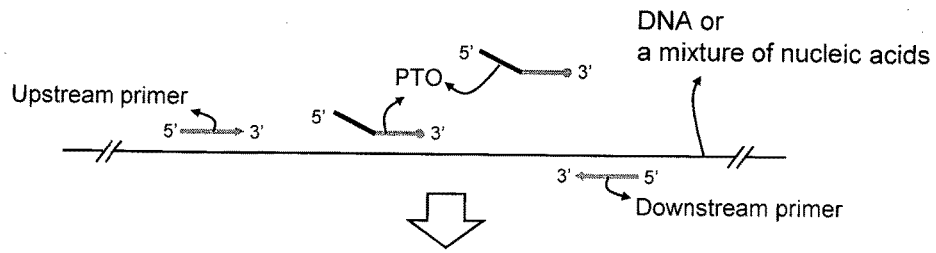
FIGS. 2A, 2B, 2C, and 2D represent schematically the first aspect of PCE-NH assay comprising melting analysis.
Figure 2:
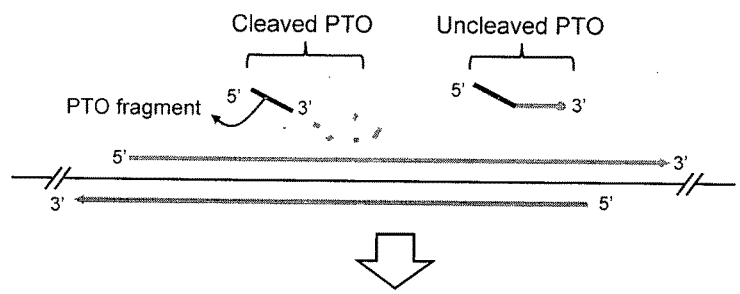
Figure 2:
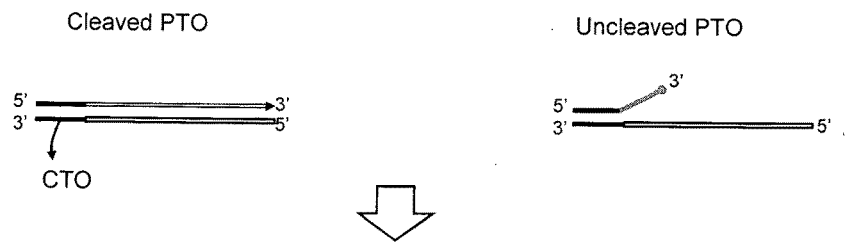
Figure 2:

When the PTO is hybridized with the target nucleic acid sequence, its 3'-targeting portion is involved in the hybridization and the 5'-tagging portion forms a single-strand with no hybridization with the target nucleic acid sequence (see FIG. 2). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging portion of the PTO.

According to an embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the term used herein "a fragment comprising the 5'-tagging portion or a part of the 5'-tagging portion of the PTO" in conjunction with cleavage of the PTO by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO" may be also described as "PTO fragment".

According to an embodiment, the PTO has a blocker portion containing a blocker resistant to cleavage by the enzyme having 5' nuclease activity and the blocker portion is used to control an initial cleavage site and/or successive cleavages.

According to an embodiment, the PTO has a blocker portion containing as a blocker at least one nucleotide resistant to cleavage by the enzyme having 5' nuclease activity.

For example, to induce cleavage at the junction site between a hybridization portion of the PTO (3'-targeting portion) and a non-hybridization portion (5'-tagging portion), the 5'-end part of 3'-targeting portion of PTO may be blocked with blockers.

The number of blockers contained in the blocker portion may be not limited, including 1-10, 2-10, 3-8 or 3-6 blockers. The blockers present in the PTO may be in a continuous or intermittent manner, suitably a continuous manner. The nucleotides as blockers with a backbone resistant to the 5' to 3' exonuclease activity include any one known to one of skill in the art. For example, it includes various phosphorothioate linkages, phosphonate linkages, phosphoroamidate linkages and 2'-carbohydrates modifications. According to an embodiment, nucleotides having a backbone resistant to the 5' to 3' exonuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

According to an embodiment, a nucleotide as a blocker includes LNA (locked nucleic acid).

The term "part" used in conjunction with the PTO or CTO such as the part of the 5'-tagging portion of the PTO, the 5'-end part of the 3'-targeting portion of the PTO and the 5'-end part of the capturing portion of the CTO refers to a nucleotide sequence composed of 1-40, 1-30, 1-20, 1-15, 1-10 or 1-5 nucleotides, suitably 1, 2, 3 or 4 nucleotides.

According to an embodiment, the enzyme having the 5' nuclease activity is DNA polymerase having a 5' nuclease activity or FEN nuclease, suitably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis, Thermis flavus, Thermococcus Thermus antranikanii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis; Thermococcus barossi, Thermococcus gorgonarius, Thermotoga maritima, Thermotoga neapolitana, Thermosiphoafricanus, Pyrococcus woesei, Pyrococcus horikoshii, Pyrococcus abyssi, Pyrodictium occultum, Aquifex pyrophilus* and *Aquifex aeolieus*. In certain embodiment, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataficus, Pyrobaculum aerophilum, Thermococcus litoralis, Archaeaglobus venefi-*

*cus, Archaeaglobus profundus, Acidianus brierlyi, Acidanus ambivalens, Desulfurococcus amylolyticus, Desulfurococcus mobilis, Pyrodictium brockii, Thermococcus gorgonarius, Thermococcus zilligii, Methanopyrus kandleri, Methanococcus igneus, Pyrococcus honkoshii, Aeropyrum pernix*, and *Archaeaglobus veneficus*.

Where the upstream primer is used in the step (a), the conditions for cleavage of the PTO may comprise extension reaction of the upstream primer.

According to an embodiment, the upstream primer is used in the step (a), a template-dependent polymerase is used for extension of the upstream primer and the template-dependent polymerase is identical to the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Step (c): Hybridization of the Fragment Released from the PTO with CTO

The fragment released from the PTO is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The CTO is acted as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released, the capturing portion of the CTO may be designed to comprise a nucleotide sequence complementary to the 5'-tagging portion. When the fragment having the 5'-tagging portion and a 5'-end part of the 3'-targeting portion is released, the capturing portion of the CTO may be designed to comprise a nucleotide sequence complementary to the 5'-tagging portion and the 5'-end part of the 3'-targeting portion. When the fragment having a part of the 5'-tagging portion of the PTO is released, the capturing portion of the CTO may be designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

When the fragment comprising the 5'-tagging portion and a 5'-end part of the 3'-targeting portion is released, the 5'-end part of the capturing portion of the CTO (see FIG. 1) may be designed to have a nucleotide sequence complementary to the cleaved 5'-end part of the 3'-targeting portion, overcoming problems associated with mismatch nucleotides.

In an embodiment, the nucleotide sequence of the 5'-end part of the capturing portion of the CTO complementary to the cleaved 5'-end part of the 3'-targeting portion may be selected depending on anticipated cleavage sites on the 3'-targeting portion of the PTO. The nucleotide sequence of the 5'-end part of the capturing portion of the CTO complementary to the cleaved 5'-end part of the 3'-targeting portion may be 1-10 nucleotides, 1-5 nucleotides or 1-3 nucleotides in length.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. Specifically, the 3'-end of the CTO is blocked to prohibit its extension. The non-extendible blocking of the CTO may be achieved in accordance with conventional methods. For instance, the blocking may be performed by adding to the 3'-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The fragment released from the PTO is hybridized with the CTO, providing a form suitable in extension of the fragment. Although an undigested PTO is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

Step (d): Extension of the Fragment

The extension reaction is carried out using the resultant of the step (c) and a template-dependent nucleic acid polymerase. The fragment hybridized with the capturing portion of the CTO is extended to form an extended strand complementary to the templating portion of the CTO, thereby forming the extended duplex. In contrast, uncleaved PTO hybridized with the capturing portion of the CTO is not extended such that no extended duplex is formed.

The term used herein "extended strand" in conjunction with the fragment means a sequence composed of the fragment and its extended sequence. The term used herein "extended duplex" means a duplex formed by extension reaction in which the fragment hybridized with the capturing portion of the CTO is extended using the templating portion of the CTO as a template and the template-dependent nucleic acid polymerase.

The template-dependent nucleic acid polymerase used in the step (d) may include any nucleic acid polymerases, for example, Klenow fragment of *E. coli* DNA polymerase I, a thermostable DNA polymerase and bacteriophage T7 DNA polymerase.

Specifically, the polymerase is a thermostable DNA polymerase which may be obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis*; *Thermococcus barossi*, *Thermococcus gorgonarius*, *Thermotoga maritima*, *Thermotoga neapolitana*, *Thermosiphoafricanus*, *Pyrococcus furiosus* (Pfu), *Pyrococcus woesei*, *Pyrococcus horikoshii*, *Pyrococcus abyssi*, *Pyrodictium occultum*, *Aquifex pyrophilus* and *Aquifex aeolieus*. More specifically, the template-dependent nucleic acid polymerase is Taq polymerase.

According to an embodiment, the enzyme having the 5' nuclease activity used in the step (b) is identical to the template-dependent nucleic acid polymerase used in the step (d). Specifically, the enzyme having the 5' nuclease activity used in the step (b), the template-dependent nucleic acid polymerase used for extension of the upstream primer and the template-dependent nucleic acid polymerase used in the step (d) are identical to one another.

Step (e): Melting or Hybridization Analysis with HO

Following the extension reaction, a melting analysis or a hybridization analysis for the resultant of the step (d) over a range of temperatures with a HO (hybridizing oligonucleotide) is performed to measure whether a signal indicative of the presence of the hybrid between the CTO and the HO is generated or not.

When the target nucleic acid sequence is not present in the nucleic acid sample, the extended duplex is not formed and the CTO and the HO form a hybrid, thereby providing a signal indicative of the presence of the hybrid between the CTO and the HO. When the target nucleic acid sequence is present in the nucleic acid sample, the extended duplex is formed to prevent the formation of the hybrid between the CTO and the HO, thereby not providing the signal.

The step (e) is performed using the HO.

The HO comprises a hybridizing nucleotide sequence complementary to the CTO. Where the extended duplex is not formed and the CTO is then in a single strand, the HO is hybridized with the CTO to form the hybrid. The hybrid is formed and/or melted over a range of temperatures during the melting or hybridization analysis to give the signal indicative of the presence of the hybrid between the CTO and the HO. Where the extended duplex is formed and the CTO is then in a double strand, the extended duplex prevents the formation of the hybrid between the CTO and the HO, thereby providing no signal indicative of the presence of the hybrid between the CTO and the HO during the melting or hybridization analysis.

The length of the HO may be widely varied. For example, the HO is 5-100 nucleotides, 5-80 nucleotides, 5-60 nucleotides, 5-40 nucleotides, 5-20 nucleotides, 5-10 nucleotides, 10-100 nucleotides, 10-80 nucleotides, 10-60 nucleotides, 10-40 nucleotides, 10-30 nucleotides, 10-20 nucleotides, 15-100 nucleotides, 15-80 nucleotides, 15-60 nucleotides, 15-40 nucleotides, 15-30 nucleotides, 15-20 nucleotides, 20-100 nucleotides, 20-80 nucleotides, 20-60 nucleotides, 20-40 nucleotides or 20-30 nucleotides in length.

In the present invention, the extended duplex of the CTO/extended strand may be more stable duplex than the hybrid of the CTO/HO. For this, the $T_m$ value of the HO may be lower than that of the CTO. According to an embodiment, the $T_m$ value of the hybrid of the CTO/HO is lower at least 10° C., 20° C., 30° C. or 40° C. than that of the extended duplex of the CTO/extended strand.

In an embodiment of this invention, the HO is blocked at its 3'-end to prohibit its extension.

The prevention of the hybrid formation between the CTO and the HO by the extended duplex may be achieved in several fashions depending on the occurrence time point of contact opportunity between the CTO and the HO.

Figure 3:
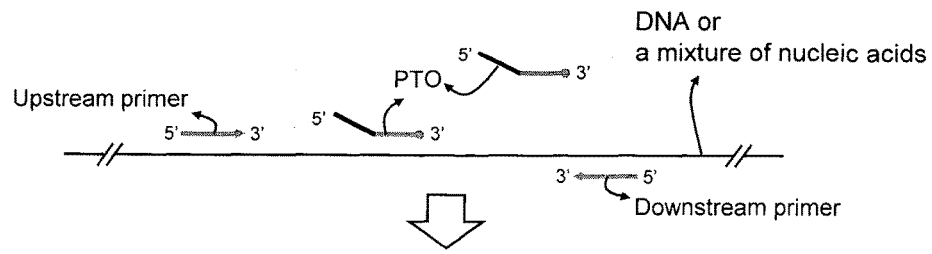
FIGS. 3A, 3B, 3C, and 3D represent schematically the first aspect of PCE-NH assay comprising melting analysis.
Figure 3:
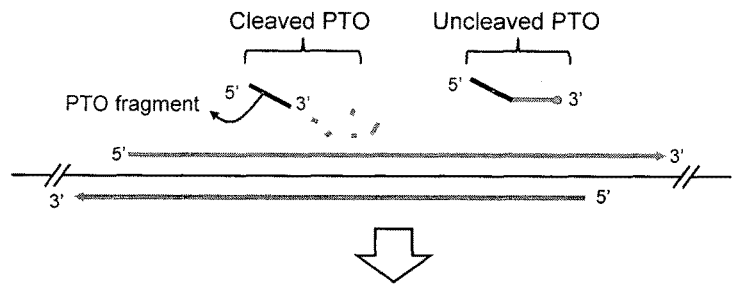
Figure 3:
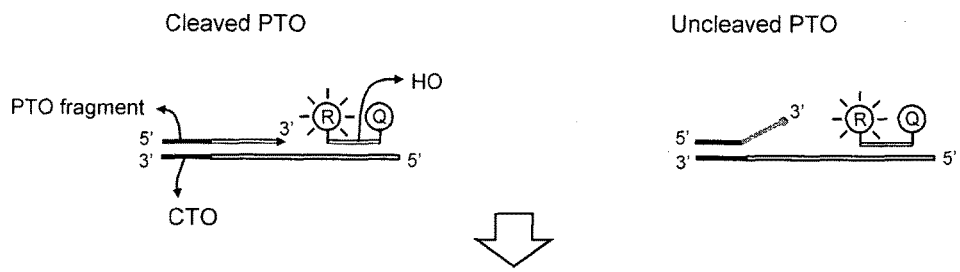
Figure 3:
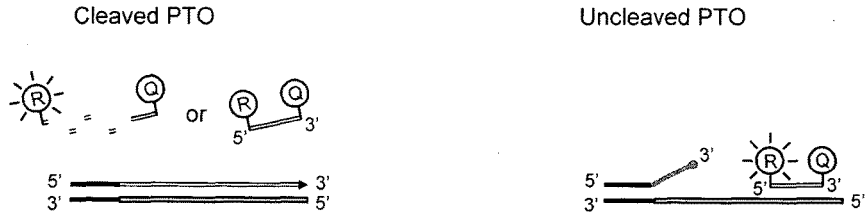

For example, where the CTO and the HO are first contacted with each other in the step (e) (e.g., performing the steps (a)-(d) and (e)-(f) in separate reaction vessels), the present invention may be carried out as depicted in FIG. 2. The HO is not contacted to the CTO prior to the extension of the PTO fragment but involved in hybridization with the resultant of the extension reaction. In the melting analysis step, the formation of the extended duplex prevents the formation of the hybrid of the CTO/HO due to the inhibition of the hybridization of the HO with the CTO.

Where the CTO and the HO are contacted with each other in the step (d) (e.g., performing the steps (a)-(f) in a single reaction vessel), the present invention may be carried out as depicted in FIG. 3. The HO may be hybridized with the CTO prior to the extension and involved in the extension reaction. When the HO is hybridized with the CTO prior to the extension of the fragment, the extension of the fragment cleaves or displaces the HO from the CTO. Particularly, where the HO is cleaved during the extension reaction, the formation of the extended duplex prevents the formation of the hybrid of the CTO/HO in the melting analysis step due to the consumption of the HO by the cleavage. Where the HO is hybridized with the CTO in the step (d), the formation of the extended duplex may permit to release (displace) the HO from the CTO (strand displacement of HO). In such case, the displaced HO may not form the hybrid with the CTO in the melting or hybridization analysis due to the inhibition of the hybridization of the HO with the CTO.

According to an embodiment, the cleavage and/or strand displacement of the HO by the extension of the PTO fragment is dependent on types of template-dependent nucleic acid polymerase or reaction conditions.

Even if the CTO and the HO have a chance to be contacted with each other in the step (d), some of the HOs may not be even hybridized with the CTO prior to the extension. In such case, the HOs may not form the hybrid with the CTO in the step (e) due to the inhibition of the hybridization of the HO with the CTO.

According to an embodiment, with adjusting reaction conditions (e.g. reaction temperature and $T_m$ value of the HO and the PTO fragment) in the step (d), the HO may not be hybridized with the CTO prior to the extension and not involved in the extension reaction.

Without regard to the step in which the HO is first contacted to the CTO, the extended duplex is formed to prevent the formation of the hybrid between the CTO and the HO in the presence of the target nucleic acid sequence by the following fashions (i) the inhibition of the hybridization of the HO with the CTO and/or (ii) the consumption of the HO by the cleavage.

In the absence of the target nucleic acid sequence, the extended duplex is not formed and the hybrid between the CTO and the HO is therefore formed.

According to an embodiment, the step (d) is performed in the presence of the HOs and the HOs are hybridized with the CTO and/or not hybridized with the CTO. According to an embodiment, the step (d) is performed in the presence of the HOs; wherein (i) the fragment hybridized with the capturing portion of the CTO is extended prior to the hybridization of the HO and/or (ii) when the HO is hybridized with the CTO prior to the extension of the fragment, the extension of the fragment cleaves or displaces the HO from the CTO, thereby the formation of the extended duplex prevents the formation of the hybrid between the CTO and the HO in the step (e) due to the inhibition of the hybridization of the HO with the CTO and/or the consumption of the HO by the cleavage According to an embodiment, the hybridization between the HO and the CTO may be prevalent than non-hybridization or not, depending on conditions for the extension reaction of the fragment hybridized with the CTO.

The target-dependent formation of the extended duplex prevents the HO from hybridization with the CTO even when the HO comprises a complementary sequence to the CTO. Even when the HO is hybridized with the CTO prior to the formation of the extended duplex, it is separated, released or removed from the CTO (e.g., by cleavage or displacement of the HO).

The HO comprises a hybridizing nucleotide sequence complementary to the CTO. The nucleotide sequence of the HO may be designed to comprise a complementary to a region of CTO other than a region to be hybridized with the PTO fragment. In this case, the HO is not competitive with the PTO fragment (or uncleaved PTO) in binding to the CTO.

According to an embodiment, the HO comprises a nucleotide sequence complementary to the templating portion of the CTO.

Figure 6:
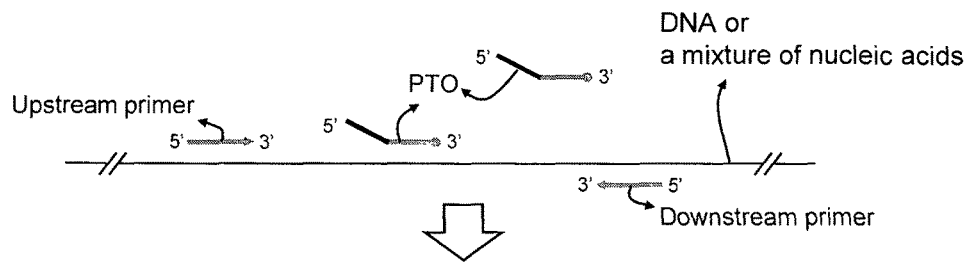
FIGS. 6A, 6B, 6C, and 6D represent schematically the first aspect of PCE-NH assay comprising melting analysis.
Figure 6:
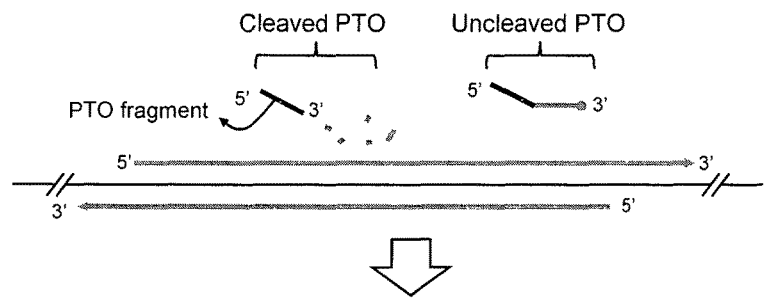
Figure 6:
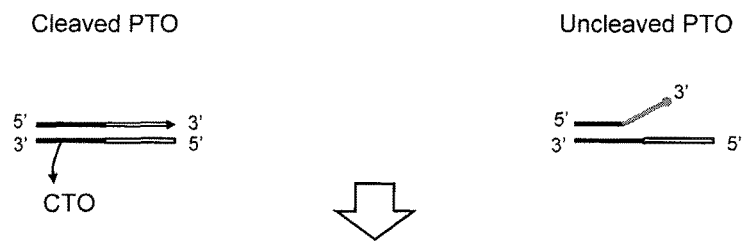
Figure 6:
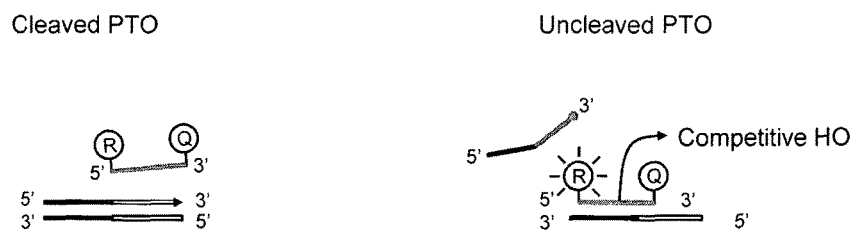
Figure 7:
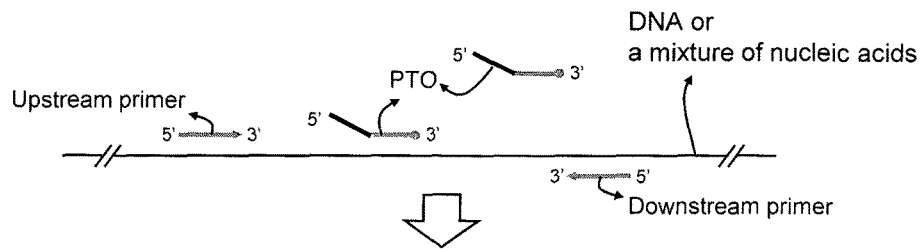
FIGS. 7A, 7B, 7C, and 7D represent schematically the first aspect of PCE-NH assay comprising melting analysis.
Figure 7:
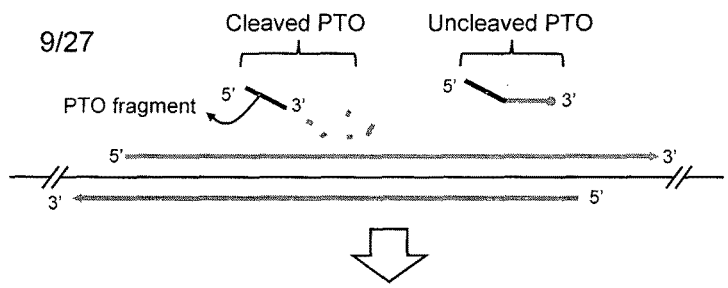
Figure 7:
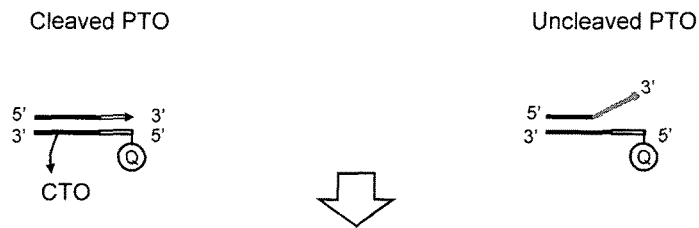
Figure 7:
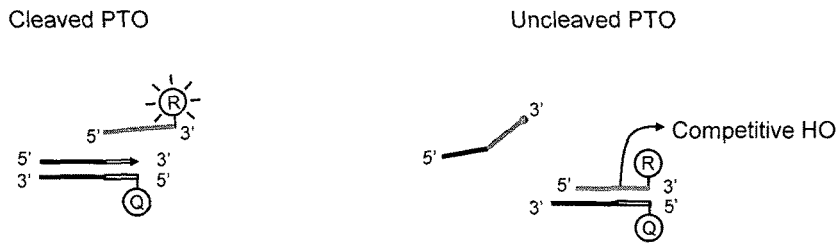

In certain embodiment, the HO may be designed to comprise a nucleotide sequence being competitive with the fragment (or uncleaved PTO) in terms of hybridization with the CTO (see FIGS. 6 and 7). In certain embodiment, such competitive HO is not cleaved by the fragment or its extension product or not displaced during the extension reaction. For instance, the HO may be designed to comprise a nucleotide sequence hybridizable with the capturing portion of the CTO.

The term used "a nucleotide sequence hybridizable with the capturing portion of the CTO" in conjunction with a sequence of the HO refers to a portion of the HO to form a double strand with the capturing portion of the CTO when the HO is hybridized with the CTO. The nucleotide sequence of the HO hybridizable with the capturing portion of the CTO may be all sequence or a partial sequence of the HO. The nucleotide sequence hybridizable with the capturing portion of the CTO corresponds to all sequence or a partial sequence (e.g., 10%, 30%, 40%, 50%, 60%, 70%, 80% 90% or 95%) in the HO.

Where the HO comprises nucleotide sequence hybridizable with the capturing portion of the CTO, it may have an overlapping sequence with the PTO fragment and/or the 5'-tagging portion of the uncleaved PTO. In this case, (i) the HO and the PTO fragment, or (ii) the HO and the 5'-tagging portion of the uncleaved PTO are competitive in terms of hybridization with the CTO.

The term used herein "competitive HO" refers to a HO comprising a competitive sequence with the PTO fragment or the uncleaved PTO (e.g., the 5'-tagging portion of the uncleaved PTO) in terms of hybridization with the CTO. According to an embodiment, the competitive HO is less competitive than the PTO fragment (practically, the extended strand of the PTO fragment) and more competitive than the 5'-tagging portion of the uncleaved PTO in terms of hybridization with the CTO.

Where the target nucleic acid sequence is present and the competitive HO is present in the step (c) and/or (d), the competition between the competitive HO and the PTO fragment in hybridization with the CTO may become problematic. In such case, it is preferable that the PTO fragment rather than the competitive HO is hybridized with the CTO and extended to produce the extended strand. As the PTO fragment hybridized with the CTO is extended, it is more advantageous than the competitive HO in hybridization with CTO.

In certain embodiment, the step (c) is performed under conditions that are more favorable to hybridization between the PTO fragment and the CTO than hybridization between the HO and the CTO. Such favorable conditions may be accomplished by various methods. For example, the 3'-end of the HO may be blocked for the favorable conditions. The HO with blocked 3'-end is hybridized with the CTO but is not extended, which increases probability of dissociation from the CTO due to competition with the PTO fragment. The PTO fragment hybridized with the CTO is extended to the extended strand, which may be more stably maintained. Therefore, the extended duplex is much more prevalent than CTO/HO hybrid in the resultant after the steps (c) and (d). Consequently, the number (or amount) of the CTO/HO hybrid is relatively decreased due to the extended duplex in the presence of the target nucleic acid sequence compared with the case of absence of the target nucleic acid sequence.

Where the target nucleic acid sequence is absent, the cleavage of the PTO does not occur to remain as an uncleaved PTO. Where both the uncleaved PTO and the competitive HO exist, the 5'-tagging portion of the uncleaved PTO and the competitive HO are competitive in hybridization with the CTO because they have an overlapping sequence with each other. Where the target nucleic acid sequence is absent, the competitive HO has to be more advantageous than the 5'-tagging portion of the uncleaved PTO in hybridization with the CTO because the principle underlying the present invention requires the hybridization of the HO with the CTO.

Where the $T_m$ value of the PTO fragment is higher than that of the competitive HO, it is more advantageous than the competitive HO in hybridization with the CTO. Considering the competition between the 5'-tagging portion of the uncleaved PTO and the competitive HO, the higher $T_m$ value of the PTO fragment is not always preferable. Even when the $T_m$ value of the PTO fragment is lower than that of the competitive HO, it may be more advantageous than the competitive HO in hybridization with the CTO due to extension of the PTO fragment hybridized with the CTO. In such case, the competitive HO may be more advantageous than the 5'-tagging portion of the uncleaved PTO in hybridization with the CTO.

With considerable factors or matters described above, suitable competitive HOs should be designed. According to an embodiment, the difference between the $T_m$ values of the CTO/HO hybrid and the PTO fragment/CTO hybrid is within ±40° C., ±30° C., ±20° C., ±15° C., ±10° C., ±5° C. or ±3° C.

According to an embodiment, the difference between the $T_m$ values of the CTO/HO hybrid and the 5'-tagging portion of the uncleaved PTO/CTO hybrid is within ±40° C., ±30° C., ±20° C., ±15° C., ±10° C., ±5° C. or ±3° C.

According to an embodiment, where the HO and the uncleaved PTO may be hybridized with the CTO in a competitive manner, the $T_m$ value of CTO/HO may be higher (e.g., at least 2° C., 4° C., 6° C., 8° C., 10° C., 15° C. or 20° C.) than that of CTO/uncleaved PTO.

The $T_m$ value of the uncleaved PTO/CTO hybrid is determined by a portion of the PTO sequence to be hybridized with the CTO. For example, where the 5'-tagging portion of the uncleaved PTO is to be hybridized with the CTO, the $T_m$ value of the 5'-tagging portion is a determinative factor for the $T_m$ value of the uncleaved PTO/CTO hybrid.

The term used herein "$T_m$ value of the uncleaved PTO" means a $T_m$ value determined by a portion of the uncleaved PTO sequence to be hybridized with the CTO, unless otherwise indicated.

According to an embodiment, the extended strand of the fragment has higher $T_m$ value than the HO and the HO has higher $T_m$ value the 5'-tagging portion of the PTO.

According to an embodiment, given hybridization with CTO, the $T_m$ value of the extended strand of the PTO fragment is higher than that of that of the HO and the $T_m$ value of the HO is higher than that of the uncleaved PTO.

According to an embodiment, the HO and the PTO fragment is designed to be not hybridized with the CTO through only a portion other than the overlapping portion. In such case, the simultaneous hybridization of the HO and the PTO fragment with the CTO may be prevented.

The $T_m$ value is determined by length and G/C content of nucleotides hybridized. According to an embodiment, the $T_m$ value may be calculated by conventional methods such as Wallace rule (R. B. Wallace, et al., *Nucleic Acids Research*, 6:3543-3547(1979)) and nearest-neighbor method (Santa-Lucia J. Jr., et al., *Biochemistry*, 35:3555-3562(1996)); Sugimoto N., et al., *Nucleic Acids Res.*, 24:4501-4505(1996)).

According to an embodiment, the $T_m$ value refers to actual $T_m$ values under reaction conditions actually practiced.

In the PCE-NH comprising melting analysis or hybridization, the signal indicative of the presence of the hybrid between the CTO and the HO may be provided by various labeling systems: (i) a label linked to the HO, (ii) a label linked to the CTO, (iii) a label linked to the HO and a label linked to the CTO, and (iv) an intercalating label.

According to a embodiment, as long as a signal in the case of the formation of the hybrid between the CTO and the HO is different from a signal in the case of no formation of the hybrid between the CTO and the HO, various types and locations of labels may be adopted in the present invention. The present invention requires, in principle, to provide a signal suitable in a melting or hybridization analysis. In this regard, the expression described above includes, for example, the following meaning: As long as a signal provided in the case that the CTO and the HO are associated to form a hybrid is different from a signal provided in the case that the CTO and the HO are dissociated from each other, various types and locations of labels may be adopted in the present invention. The expression used herein "a signal in the case of the formation of the hybrid between the CTO and the HO is different from a signal in the case of no formation of the hybrid between the CTO and the HO" includes, for example, the following meaning: "a signal provided in the case that the CTO and the HO are associated to form a hybrid is different from a signal provided in the case that the CTO and the HO are dissociated from each other". The labels for signaling described below have to possess the following feature: A signal provided in the case that the CTO and the HO are associated to form a hybrid is different from a signal provided in the case that the CTO and the HO are dissociated from each other.

According to an embodiment, the signal difference is provided by such a phenomenon as signal generation and signal distinction.

According to an embodiment, the signal difference is provided by such a phenomenon as the change of intensity (signal increase and signal decrease).

The labels useful in the present invention include a multitude of labels known to one of skill in the art, for example, including a single label, an interactive dual label and an intercalating label.

The label useful in the present invention includes an interactive dual label (see FIGS. 2-4 and 6-7).

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively. Interactive dual label includes the label pair providing detectable signal based on contact-mediated quenching (Salvatore et al., Nucleic Acids Research, 2002 (30) no. 21 e122 and Johansson et al., J. AM. CHEM. SOC 2002 (124) pp 6950-6956). In the present invention, the interactive label system includes any or all cases inducing signal changes by interaction between at least two molecules (e.g. dyes).

According to an embodiment of this invention, the signal indicative for the presence or absence of the CTO-HO hybrid is generated by interactive label systems, particularly the FRET label system (i.e., interactive dual label system).

According to an embodiment, the HO or the CTO has an interactive dual label comprising a reporter molecule and a quencher molecule; wherein the interactive dual label is positioned at a site such that a signal from the interactive dual label in the case of the formation of the hybrid between the CTO and the HO is different from a signal from the interactive dual label in the case of no formation of the hybrid between the CTO and the HO.

According to an embodiment, the HO has an interactive dual label comprising a reporter molecule and a quencher molecule.

When the HO is in a single stranded state, the reporter molecule and the quencher molecule on the HO are conformationally adjacent to each other to allow the quencher molecule to quench the signal from the reporter molecule. Where the target nucleic acid sequence is absent and the CTO/HO hybrid is formed, the reporter molecule and the quencher molecule on the HO are conformationally separated to allow the quencher molecule to unquench the signal from the reporter molecule, thereby causing signal change to provide a signal indicative of the presence of the CTO/HO hybrid during the melting or hybridization analysis (see FIGS. 2 and 3). Where the target nucleic acid sequence is present and the CTO/HO hybrid is not formed, the signal change does not occur to provide no signal indicative of the presence of the CTO/HO hybrid during the melting or hybridization analysis (see FIGS. 2 and 3).

The expression used herein "the reporter molecule and the quencher molecule are conformationally adjacent" means that the reporter molecule and the quencher molecule are three-dimensionally adjacent to each other by a conformational structure of the HO or CTO such as random coil and hairpin structure.

The expression used herein "the reporter molecule and the quencher molecule are conformationally separated" means that the reporter molecule and the quencher molecule are three-dimensionally separated by change of a conformational structure of the HO or CTO upon the formation of a double strand.

According to an embodiment, the templating portion of the CTO has an interactive dual label comprising a reporter molecule and a quencher molecule, and the HO comprises a complementary sequence to a label-linked region of the CTO. Where the CTO is in a single stranded form, the reporter molecule and the quencher molecule on the CTO are conformationally adjacent to each other to allow the quencher molecule to quench the signal from the reporter molecule. Where the target nucleic acid sequence is absent and the CTO/HO hybrid is formed, the reporter molecule and the quencher molecule on the CTO are conformationally separated to allow the quencher molecule to unquench the signal from the reporter molecule, thereby causing signal change to provide a signal indicative of the presence of the CTO/HO hybrid during the melting or hybridization analysis. Where the target nucleic acid sequence is present and the CTO/HO hybrid is not formed, the signal change does not occur, resulting in no signal indicative of the presence of the CTO/HO hybrid during the melting or hybridization analysis.

Where the present invention uses the CTO with an interactive dual label, the extended duplex of the CTO/extended strand may provide signals in the melting analysis. As the $T_m$ value of the extended duplex is different from that of the CTO/HO hybrid, the signal from the CTO/HO hybrid may be differentially detected from the signal from the extended duplex. It would be appreciated that the present invention using signals from the CTO/HO hybrid is distinctly different from those using signals from extended duplexes.

According to an embodiment, the reporter molecule and the quencher molecule may be located at any site on the HO or CTO, so long as the signal from the reporter molecule is quenched and unquenched depending on melting of the CTO/HO hybrid or hybridization of the CTO and HO.

According to an embodiment, one of the reporter molecule and the quencher molecule on the HO is located at its 5'-end or at 1-5 nucleotides apart from its 5'-end and the other is located to quench and unquench the signal from the reporter molecule depending on conformation of the HO. According to an embodiment, one of the reporter molecule and the quencher molecule on the HO is located at its 3'-end or at 1-5 nucleotides apart from its 3'-end and the other is located to quench and unquench the signal from the reporter molecule depending on conformation of the HO. In certain embodiments, the reporter molecule and the quencher molecule each is located at both ends of the HO.

According to an embodiment, one of the reporter molecule and the quencher molecule on the CTO is located at its 5'-end or at 1-5 nucleotides apart from its 5'-end and the other is located to quench and unquench the signal from the reporter molecule depending on conformation of the CTO. According to an embodiment, one of the reporter molecule and the quencher molecule on the CTO is located at its 3'-end or at 1-5 nucleotides apart from its 3'-end and the other is located to quench and unquench the signal from the reporter molecule depending on conformation of the CTO.

The reporter molecule and the quencher molecule useful in the present invention may include the fluorescent label described herein.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule (or dark quencher molecule) capable of quenching a fluorescence of a wide range of wavelengths or a specific wavelength may be used in the present invention. Examples of those are BHQ and DABCYL. In the signaling system comprised of reporter and quencher, the reporter encompasses a donor of FRET and the quencher encompasses the other partner (acceptor) of FRET. For example, a fluorescein dye is used as the reporter and a rhodamine dye as the quencher.

According to an embodiment, where the quencher molecule is fluorescent, the signal detection is performed by measuring signal change from the quencher molecule or signal changes from both the quencher molecule and the reporter molecule.

Figure 4:
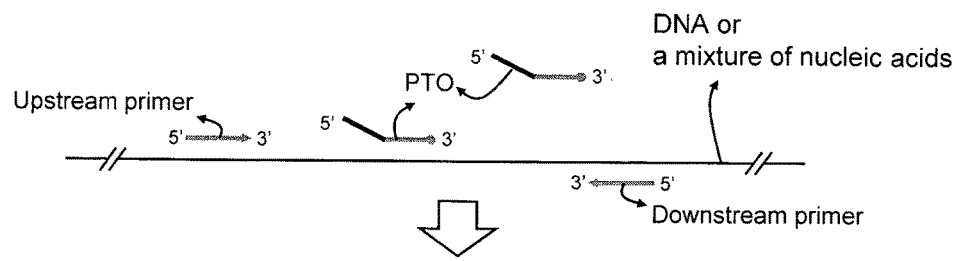
FIGS. 4A, 4B, 4C, and 4D represent schematically the first aspect of PCE-NH assay comprising melting analysis.
Figure 4:
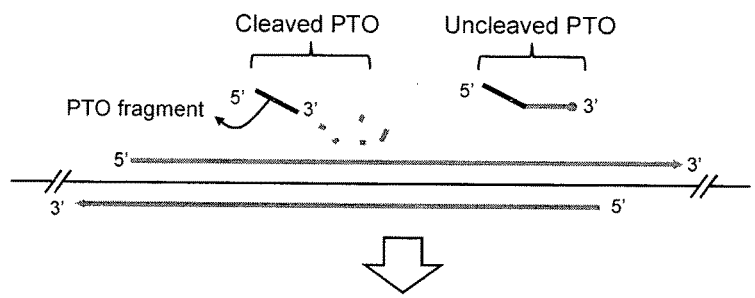
Figure 4:
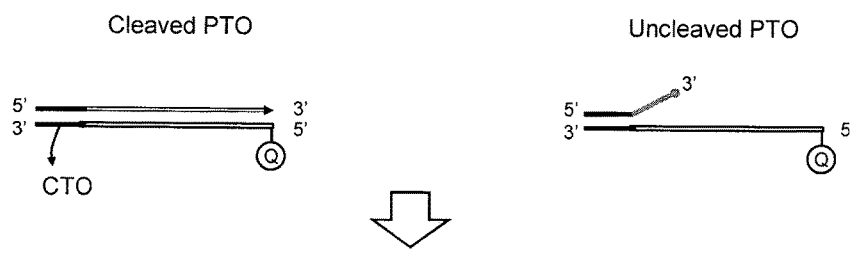
Figure 4:

The present inventions may use an interstrand-interactive dual label system (see FIG. 4).

According to an embodiment, the HO has one of an interactive dual label comprising a reporter molecule and a quencher molecule and the CTO has the other of the interactive dual label; wherein the interactive dual label is positioned at a site such that a signal from the interactive dual label in the case of the formation of the hybrid between the CTO and the HO is different from a signal from the interactive dual label in the case of no formation of the hybrid between the CTO and the HO.

The interstrand-interactive dual label uses interaction between the label linked to the CTO (e.g., donor molecule) and the label to the HO (e.g., acceptor molecule).

The HO has one of an interactive dual label comprising a reporter molecule and a quencher molecule and the CTO has the other of the interactive dual label. The hybridization between the CTO and the HO results in signal change from the interstrand-interactive dual label, providing the signal indicative of the presence of the CTO/HO hybrid (see FIG. 4). In certain embodiment, the label to the CTO is linked to the templating portion.

In certain embodiment, the reporter molecule and the quencher molecule each is linked to the 3'-end of the HO and the 5'-end of the CTO.

Figure 5:
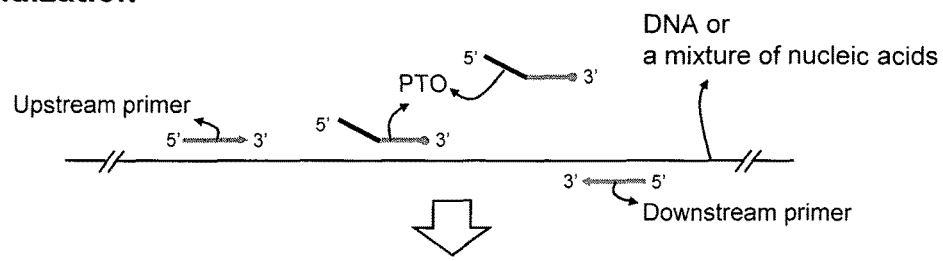
FIGS. 5A, 5B, 5C, and 5D represent schematically the first aspect of PCE-NH assay comprising melting analysis.
Figure 5:
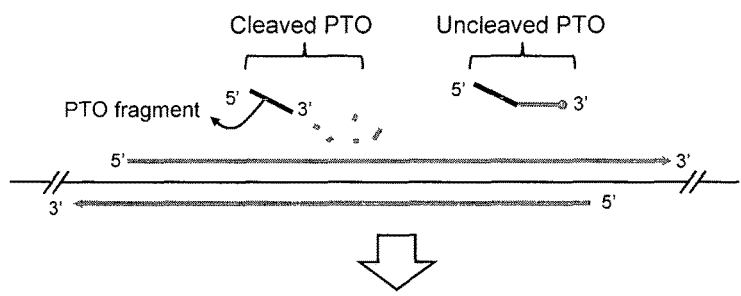
Figure 5:
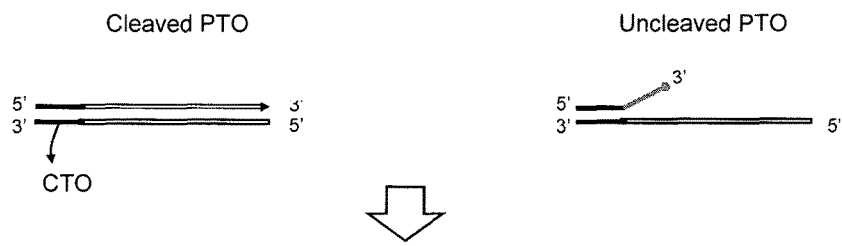
Figure 5:

In certain embodiment, the present method is performed using one additional HO comprising a hybridizing nucleotide sequence complementary to the CTO and the two HOs are hybridized with the CTO in an adjacent manner to each other; wherein one of the two HOs has one of an interactive dual label comprising a reporter molecule and a quencher molecule and the other of the two HOs has the other of the interactive dual label; wherein the interactive dual label is positioned at a site such that a signal from the interactive dual label in the case of the formation of the hybrid between the CTO and the two HOs is different from a signal from the interactive dual label in the case of no formation of the hybrid between the CTO and the two HOs.

Where the two HOs are not hybridized with the CTO, they are separated from each other to separate the reporter molecule from the quencher molecule, thereby no quenching of the signal from the reporter molecule. Where two HOs are hybridized with the CTO in an adjacent manner to each other, the hybridization allows the quencher molecule to quench the signal from the reporter molecule, thereby causing signal change to provide a signal indicative of the presence of the CTO/HO hybrid during the melting or hybridization analysis. Where the target nucleic acid sequence is present and the CTO/HO hybrid is not formed, the signal change does not result in no signal indicative of the presence of the CTO/HO hybrid during the melting or hybridization analysis.

Where the single label is used, it may be linked to either the HO or the CTO (see FIG. 5).

According to an embodiment, the HO or the CTO has a single label; wherein the single label is positioned at a site such that a signal from the single label in the case of the formation of the hybrid between the CTO and the HO is different from a signal from the single label in the case of no formation of the hybrid between the CTO and the HO.

The single label has to be capable of providing a different signal depending on its presence on a double strand or single strand. The single label includes a fluorescent label, a luminescent label, a chemiluminescent label, an electrochemical label and a metal label. Preferably, the single label includes a fluorescent label.

In certain embodiment, the single label is a fluorescent label capable of generating signals different intensities depending on whether nucleic acid sequences having the single label is in a single strand or a double strand.

FIG. 5 illustrates the present invention using a single label. In FIG. 5, the HO has a single label. Where the HO is hybridized with the CTO during the melting analysis, the signal from the single label to the HO is changed. In contrast, where the HO is not hybridized with the CTO, the signal from the single label to the HO is not changed.

In an embodiment, where the CTO has a single label, the HO comprises a complementary sequence to a label-linked region of the CTO. Where the HO is hybridized with the CTO during the melting analysis, the signal from the single label to the CTO is changed. In contrast, where the HO is not hybridized with the CTO, the signal from the single label to the CTO is not changed. In this case, the extended duplex of the CTO/extended strand may provide signals in the melting analysis. As the $T_m$ value of the extended duplex is different from that of the CTO/HO hybrid, the signal from the CTO/HO hybrid may be differentially detected from the signal from the extended duplex. It would be appreciated that the present invention using signals from the CTO/HO hybrid is distinctly different from those using signals from extended duplexes.

In an embodiment, the templating portion of the CTO has a single label and the HO comprises a complementary sequence to a label-linked region of the CTO.

The types and positions of the fluorescent label are disclosed in U.S. Pat. Nos. 7,537,886 and 7,348,141.

The fluorescent label useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™(576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer.

For example, the fluorescent label include JOE, FAM, TAMRA, ROX and fluorescein-based label.

The label may be linked to either the HO or the CTO by conventional methods. For instance, the label is linked to the HO or the CTO through a spacer containing carbon atoms (e.g., 3-carbon spacer, 6-carbon spacer or 12-carbon spacer).

The present invention may employ an intercalating label for providing the signal indicative of the presence of the hybrid between the CTO and the HO. Exemplified intercalating dyes useful in this invention include SYBR™ Green I, PO-PRO™-1, BO-PRO™-1, SYTO™43, SYTO™44, SYTO™45, SYTOX™Blue, POPO™-1, POPO™-3, BOBO™-1, BOBO™-3, LO-PRO™-1, JO-PRO™-1, YO-PRO™1, TO-PRO™1, SYTO™ 11, SYTO™ 13, SYTO™ 15, SYTO™ 16, SYTO™ 20, SYTO™ 23, TOTO™-3, YOYO™3, GelStar™ and thiazole orange. The intercalating dyes intercalate specifically into double-stranded nucleic acid molecules to generate signals.

Where the present invention uses intercalating dyes, the extended duplex of the CTO/extended strand may provide signals in the melting or hybridization analysis. As the $T_m$ value of the extended duplex is different from that of the CTO/HO hybrid, the signal from the CTO/HO hybrid may be differentially detected from the signal from the extended duplex. It would be appreciated that the present invention using signals from the CTO/HO hybrid is distinctly different from those using signals from extended duplexes.

The HO used in the present invention may be any probe so long as it is capable of generating signals upon hybridization during a melting or hybridization analysis, including Molecular Beacon™ (U.S. Pat. No. 5,925,517), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), LUX™ (I. A. Nazarenko, et al. Nucleic Acids Res 2002, 30:2089-2095. and U.S. Pat. No. 7,537,886, Hybridization probe (Bernard P S, et al., Clin Chem 2000, 46, 147-148 and Deepti Parashar et al., Indian J Med Res 124, review article October 2006 385-398).

The melting or hybridization analysis in the step (e) may be carried out by various processes known to one of skill in the art.

The term used herein "melting analysis" means a method in which a signal indicative of the presence of the CTO/HO hybrid is obtained by melting of a duplex, including a method to measure signals at two different temperatures, melting curve analysis, melting pattern analysis and melting peak analysis.

The term used herein "hybridization analysis" (or "annealing analysis") means a method in which a target signal indicative of the presence of the CTO/HO hybrid is obtained during the formation of a duplex, including a method to measure signals at two different temperatures, hybridization curve analysis, hybridization pattern analysis and hybridization peak analysis.

In general, where a target signal can be generated by the melting analysis, it also may be obtained by the hybridization analysis; and vice versa. Unless otherwise indicated herein, the term "melting analysis" is intended to encompass the hybridization analysis.

The melting curve or hybridization curve may be obtained by conventional technologies, for example, as described in U.S. Pat. Nos. 6,174,670 and 5,789,167, Drobyshev et al, Gene 188: 45(1997); Kochinsky and Mirzabekov *Human Mutation* 19:343(2002); Livehits et al *J. Biomol. Structure Dynam.* 11:783(1994); and Howell et al *Nature Biotechnology* 17:87(1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

Step (f): Detection of Signal Indicating the Presence of the CTO/HO Hybrid

In the melting or hybridization analysis, the signal indicative of the presence of the hybrid between the CTO and the HO is detected. The presence of the hybrid between the CTO and the HO indicates the absence of the target nucleic acid sequence and the absence of the hybrid between the CTO and the HO indicates the presence of the target nucleic acid sequence.

In certain embodiment, the melting analysis is performed at least twice for quantitative analysis. The area or height of melting peaks obtained in melting analysis is affected by the CTO/HO hybrid, providing information as to the initial amount of target nucleic acid sequences. The cycle number of melting analysis at which the melting peak area or height crosses a threshold value is measured to quantify the amount of target nucleic acid sequences.

For example, the present invention may be carried out by (i) repeating the steps (a)-(d) with denaturation between the repeating cycles (ii) performing a melting analysis for the CTO/HO hybrid; and (iii) repeating at least twice the steps (i) and (ii). The data may be obtained in a predetermined repetition interval with at least two points. Then, melting analysis results (e.g., the melting peak area or height) are plotted against each cycle number (or cumulative cycle number) of melting analysis and compared, thereby quantifying the amount of target nucleic acid sequences. The number of the repetition of the steps (a)-(d) may be optionally adjusted.

Alternatively, melting analysis results (e.g., the melting peak area or height) are plotted against each cycle number (or cumulative cycle number) of melting analysis and compared, thereby quantifying the amount of target nucleic acid sequences.

According to an embodiment, a signal in the case of the presence of target sequences is different from a signal in the case of the absence of target sequences. Where the target sequence is detected by a melting analysis or hybridization analysis, such signal difference includes differences in heights or areas of melting peaks. In an embodiment, such signal difference is by at least 10%, at least 30%, at least 50%, at least 70% or at least 90%.

According to an embodiment, the method is performed using a control group having no target nucleic acid sequence or a predetermined amount of the target nucleic acid sequence. The present invention is carried out for the nucleic acid sample of interest together with the control group and the results are compared, ensuring more accurate determination of the presence or amount of the target nucleic acid sequence in the nucleic acid sample.

The present invention may be carried out either in a liquid phase or on a solid phase.

Target Detection on a Solid Phase

According to an embodiment, the present invention is performed on the solid phase, and one of the CTO and HO is immobilized on the solid substrate or to become immobilized on a solid substrate before the detection of the signal in the step (f) and the signal is detected on the solid substrate.

The immobilization of the CTO or HO may be done in two fashions.

In the first fashion, either the CTO or HO having been already immobilized on the solid substrate is involved in the steps (c)-(f). In the second fashion, either the CTO or HO is involved in a non-immobilized form in the steps (c), (d) or (e) and then immobilized on the solid substrate.

According to an embodiment, one of the CTO and HO become immobilized on a solid substrate between the step (d) and the step (e) in the PCE-NH assay comprising melting or hybridization analysis.

The labeling system for the solid phase reaction may be the same as that for the labeling systems described above. Furthermore, the single label for the solid phase reaction is more versatile than that described above. In the solid phase reaction, the single label is not required to possess the capability of generating signals different intensities depending on whether nucleic acid sequences having the single label is in a single strand or a double strand.

The single label includes, but not limited to, a chemical label (e.g., biotin), an enzymatic label (e.g., alkaline phosphatase, peroxidase, 3-galactosidase and β-glucosidase), a radioisotope label (e.g., $I^{125}$ and $C^{14}$), a fluorescent label, a luminescent label, a chemiluminescent label, and a metal label (e.g., gold). For the solid phase reaction, the immobilization of the CTO or HO may be done directly or indirectly (specifically indirectly) through its 5'-end or 3'-end (specifically the 3'-end) onto the surface of the solid substrate. Furthermore, the CTO or HO may be immobilized on the surface of the solid substrate in a covalent or non-covalent manner. Where the immobilized the CTO or HO is immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for immobilization. In addition, poly (T) tail or poly (A) tail may serve as linkers and significantly decrease space hindrance that is an inhibitory factor to enzymatic actions (e.g., enzymatic cleavage reactions), contributing to increase in hybridization efficiency. The poly (T) tail or poly (A) tail as linkers is not considered a sequence of probes.

According to an embodiment, the CTO or HO may be immobilized on the solid substrate via interaction between binding partners (e.g., biotin/streptavidin). For example, the CTO or HO with one of binding partners (biotin and streptavidin) may be immobilized on the solid substrate whose surface is modified with the other binding partner.

According to an embodiment, the CTO or HO may be immobilized on the solid substrate by a nucleotide sequence for immobilization. For example, the solid substrate whose surface is modified with the nucleotide sequence for immobilization may be used to immobilize the CTO or HO with additional sequence complementary to the nucleotide sequence for immobilization.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized CTO or HO on the microarray serves as hybridizable array elements. The to solid substrate to fabricate microarray includes, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. The solid substrate may be in the form of a dipstick, a plate, a particle (e.g., bead), an affinity column and a membrane. A plurality of immobilized CTOs or HOs in this invention may be immobilized on an addressable region or two or more addressable regions on a solid substrate that may comprise 2-1,000,000 addressable regions. Immobilized CTOs or HOs may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the oligonucleotides are physically separated. In this regard, the number of target nucleic acid sequences to be detected by the present invention on the solid phase is not limited.

Using confocal detection devices, the signal only on the solid substrate may be detected without influence of labels suspended in a liquid phase.

According to an embodiment, the method is performed with no use of the upstream oligonucleotide and the cleavage of the PTO in the step (b) occurs with no help of the upstream oligonucleotide or its extended strand. The embodiment using upstream oligonucleotide-independent 5' nuclease activity is described in more detail as follows:

Target Detection by a PCE-NH Assay Based on Upstream Oligonucleotide-Independent 5' Nuclease Activity In another aspect of the present invention, there is provided a method for detecting a target nucleic acid sequence in a nucleic acid sample by a PCE-NH (PTO Cleavage and Extension-Dependent Non-Hybridization) assay, comprising:

(a) hybridizing the target nucleic acid sequence with a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO; wherein the PTO hybridized with the target nucleic acid is cleaved by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) performing a melting analysis or a hybridization analysis for the resultant of the step (d) over a range of temperatures with a HO (hybridizing oligonucleotide) comprising a hybridizing nucleotide sequence complementary to the CTO; wherein when the target nucleic acid sequence is not present in the nucleic acid sample, the extended duplex is not formed and the CTO and the HO form a hybrid, thereby providing a signal indicative of the presence of the hybrid between the CTO and the HO; wherein when the target nucleic acid sequence is present in the nucleic acid sample, the extended duplex is formed to prevent the formation of the hybrid between the CTO and the HO, thereby not providing the signal; wherein the signal is provided by (i) a label linked to the HO, (ii) a label linked to the CTO, (iii) a label linked to the HO and a label linked to the CTO, or (iv) an intercalating label; and (f) detecting the signal indicative of the presence of the hybrid between the CTO and the HO; wherein the presence of the hybrid between the CTO and the HO indicates the absence of the target nucleic acid sequence; wherein the absence of the hybrid between the CTO and the HO indicates the presence of the target nucleic acid sequence.

Since the present method based on upstream oligonucleotide-independent 5' nuclease activity is the same as the first aspect of the PCE-NH assay using upstream oligonucleotides except for no use of upstream oligonucleotides, the common descriptions between them are omitted in order to avoid undue redundancy leading to the complexity of this specification.

Interestingly, the present method based on upstream oligonucleotide-independent 5' nuclease activity practically provides target signals by the PCE-NH assay even no use of upstream oligonucleotides.

For the present method, conventional enzymes having upstream oligonucleotide-independent 5' nuclease activity may be used. Among template-dependent polymerases having 5' nuclease activity, there are several enzymes having upstream oligonucleotide-independent 5' nuclease activity, e.g., Taq DNA polymerase.

Considering amplification of target nucleic acid sequences and cleavage efficiency of the PTO, the PCE-NH assay of the present invention is preferably performed using upstream oligonucleotides.

Kit for Target Detection

In still another aspect of this invention, there is provided a kit for detecting a target nucleic acid sequence in a nucleic acid sample by a PCE-NH (PTO Cleavage and Extension-Dependent Non-Hybridization) assay, comprising:

(a) an upstream oligonucleotide; wherein the upstream oligonucleotide comprises a hybridizing nucleotide sequence complementary to the target nucleic acid sequence;

(b) a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed; and (d) a HO (hybridizing oligonucleotide) comprising a hybridizing nucleotide sequence complementary to the CTO;

wherein when the target nucleic acid sequence is not present in the nucleic acid sample, the extended duplex is not formed and the CTO and the HO form a hybrid, thereby providing a signal indicative of the presence of the hybrid between the CTO and the HO; wherein when the target nucleic acid sequence is present in the nucleic acid sample, the extended duplex is formed to prevent the formation of the hybrid between the CTO and the HO, thereby not providing the signal; wherein the kit further comprises (i) a label linked to the HO, (ii) a label linked to the CTO, (iii) a label linked to the HO and a label linked to the CTO, or (iv) an intercalating label.

Since the kit of this invention is constructed to perform the detection method of the present invention described above, the common descriptions between them are omitted in order to avoid undue redundancy leading to the complexity of this specification.

In an embodiment of this invention, the kit further comprises an enzyme having a 5' nuclease activity. In an embodiment of this invention, the kit further comprises a template-dependent nucleic acid polymerase.

Other embodiments of the present kits may be described with reference to those of the present method described above.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

II. Second Aspect of Target Detection Process by a PCE-NH Assay

In another aspect of the present invention, there is provided a method for detecting a target nucleic acid sequence in a nucleic acid sample on a solid phase by a PCE-NH (PTO Cleavage and Extension-Dependent Non-Hybridization) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) hybridizing the resultant of the step (d) with a HO (hybridizing oligonucleotide) comprising a hybridizing nucleotide sequence complementary to the CTO under conditions suitable for hybridization between the CTO and the HO; wherein one of the CTO and the HO is labeled with a single label and the other unlabeled is immobilized on a solid substrate or is to become immobilized on a solid substrate before the detection of the signal in the step (f); wherein when the target nucleic acid sequence is not present in the nucleic acid sample, the extended duplex is not formed and the CTO and the HO form the hybrid, thereby providing a signal from the single label on the solid substrate; wherein when the target nucleic acid sequence is present in the nucleic acid sample, the extended duplex is formed to prevent the formation of the hybrid between the CTO and the HO, thereby providing no signal from the single label on the solid substrate; and (f) detecting the signal on the solid substrate to detect the hybrid between the CTO and the HO on the solid substrate; wherein the presence of the hybrid between the CTO and the HO indicates the absence of the target nucleic acid sequence; wherein the absence of the hybrid between the CTO and the HO indicates the presence of the target nucleic acid sequence.

The second aspect of this invention is based on PCE-NH (PTO Cleavage and Extension-Dependent Non-Hybridization) approach as the first aspect of this invention. The second aspect of this invention is characterized in that one of the CTO and the HO is labeled with a single label and the other unlabeled is immobilized on a solid substrate or is to become immobilized on a solid substrate before the detection of the signal in the step (f), and a signal can be detected at a pre-determined temperature.

The second aspect of this invention may be considered as a modified version of PCE-NH approach for the effective realization of the target detection by using solid substrate and a single label in which the signal from the single label is generated on the solid substrate in the absence of the target nucleic acid sequence and the signal from the single label is extinguished or decreased on the solid substrate in the presence of the target nucleic acid sequence by use of a combination of two oligonucleotides, the CTO and the HO. To achieve that one of the CTO and the HO is labeled with a single label and the other unlabeled is immobilized on a solid substrate or is to become immobilized on a solid substrate before the detection of the signal in the step (f) and the signal from the label is detected at the temperature suitable for hybridization between the CTO and the HO.

As the first aspect of this invention, the second aspect is also applicable to detect a target nucleic acid sequence even when the HO is not cleaved (i.e., the hybridization between the HO and the CTO is inhibited by the formation of the extended duplex) as well as when the HO is cleaved.

The second aspect of the PCE-NH assay on a solid phase will be described in more detail as follows:

Step (a): Hybridization of an Upstream Oligonucleotide and a PTO with a Target Nucleic Acid Sequence The step (a) may be described with reference to descriptions for the step (a) of the first aspect of the PCE-NH assay comprising melting or hybridization analysis.

Step (b): Release of a Fragment from the PTO Cleavage

The step (b) may be described with reference to descriptions for the step (b) of the first aspect of the PCE-NH assay comprising melting or hybridization analysis.

Step (c): Hybridization of the Fragment Released from the PTO with CTO

The step (c) may be described with reference to descriptions for the step (c) of the first aspect of the PCE-NH assay comprising melting or hybridization analysis.

Step (d): Extension of the Fragment

The step (d) may be described with reference to descriptions for the step (d) of the first aspect of the PCE-NH assay comprising melting or hybridization analysis.

Step (e): Hybridization the Extended Duplex with HO

Following the extension reaction, the resultant of the step (d) is hybridized with a HO (hybridizing oligonucleotide) comprising a hybridizing nucleotide sequence complementary to the CTO under conditions suitable for hybridization between the CTO and the HO. One of the CTO and the HO is labeled with a single label and the other unlabeled is immobilized on a solid substrate or is to become immobilized on a solid substrate before the detection of the signal in the step (f).

The second aspect of the present invention is characterized in that the single-labeled oligonucleotide is not immobilized on the solid substrate and provides signals on the solid substrate only when it is hybridized with the immobilized oligonucleotide on the solid substrate.

When the target nucleic acid sequence is not present in the nucleic acid sample, the extended duplex is not formed and the CTO and the HO form the hybrid, thereby providing a signal from the single label on the solid substrate. When the target nucleic acid sequence is present in the nucleic acid sample, the extended duplex is formed to prevent the formation of the hybrid between the CTO and the HO, thereby providing no signal from the single label on the solid substrate. According to an embodiment, the washing step is performed between the step (e) for hybridization of the HO with the resultant of the step (d) and the step (f) for the detection of the signal. According to an embodiment, before washing, it is necessary for one of the CTO or HO to be immobilized on the substrate.

Alternatively, the washing step is not required. Using confocal detection devices on a solid phase, signal existed only on the solid substrate may be detected with no influence of signal from labels present in a reaction solution.

The details of the HO may be described with reference to descriptions for the HO for the first aspect of the PCE-NH assay comprising melting or hybridization analysis.

Figure 8:
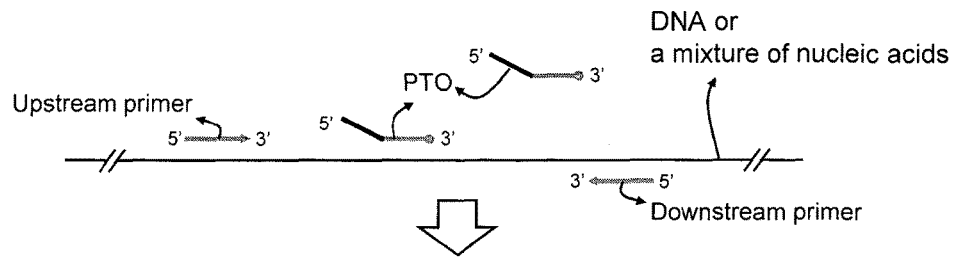
FIGS. 8A, 8B, 8C, and 8D represent schematically the second aspect of PCE-NH assay using a single label on a solid phase.
Figure 8:
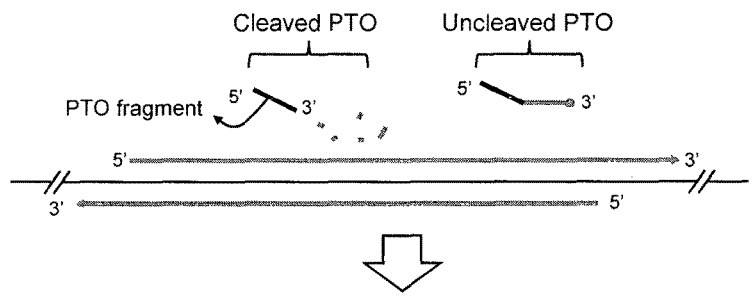
Figure 8:
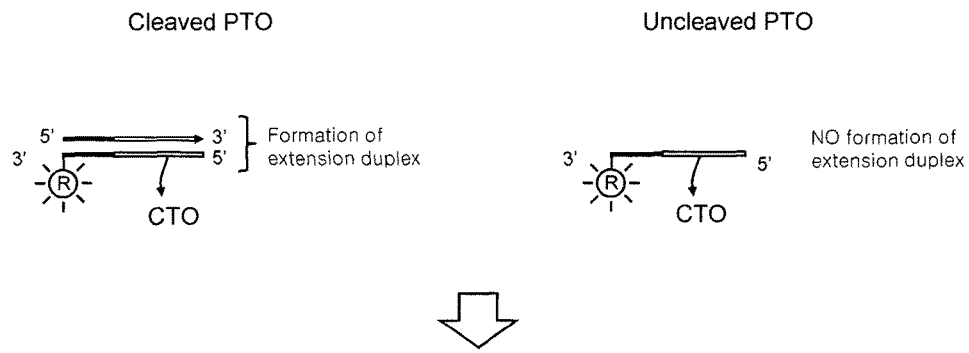
Figure 8:
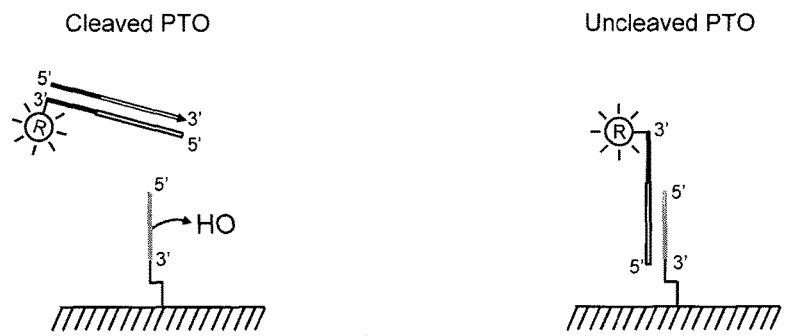
Figure 9:
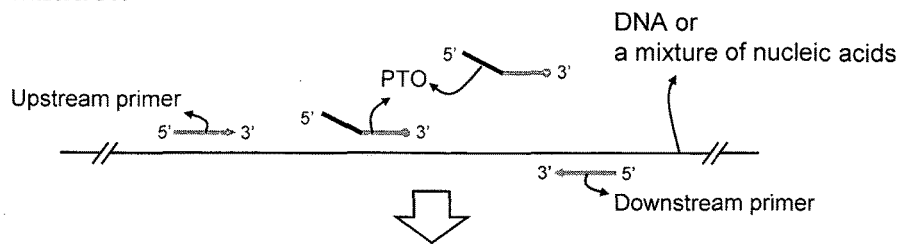
FIGS. 9A, 9B, 9C, and 9D represent schematically the second aspect of PCE-NH assay using a single label on a solid phase.
Figure 9:
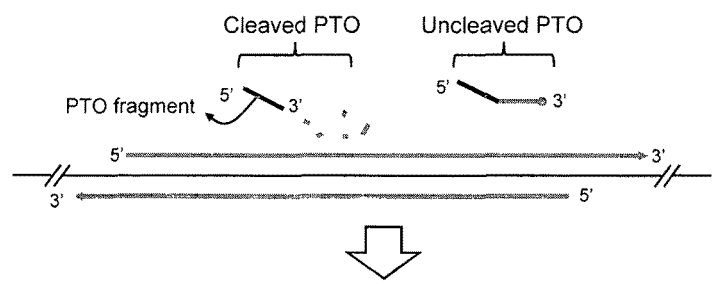
Figure 9:
Figure 9:
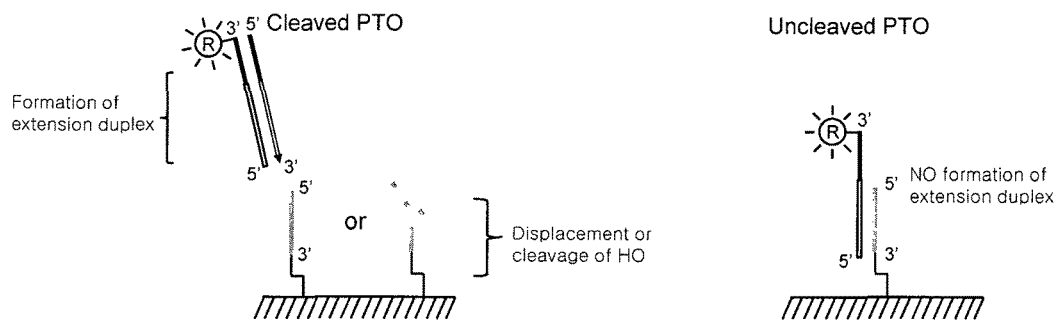
Figure 11:
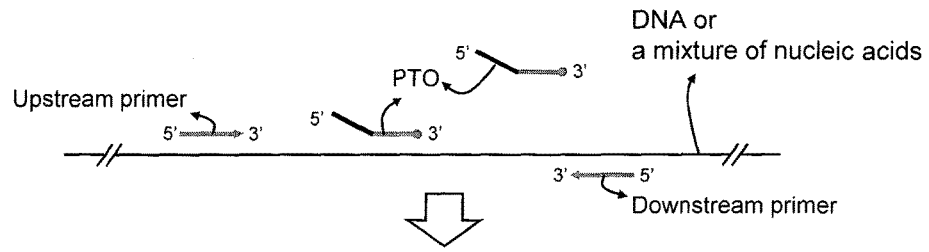
FIGS. 11A, 11B, 11C, and 11D represent schematically the second aspect of PCE-NH assay using a single label on a solid phase.
Figure 11:
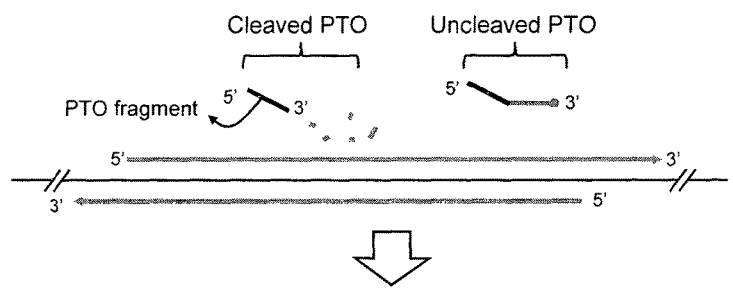
Figure 11:
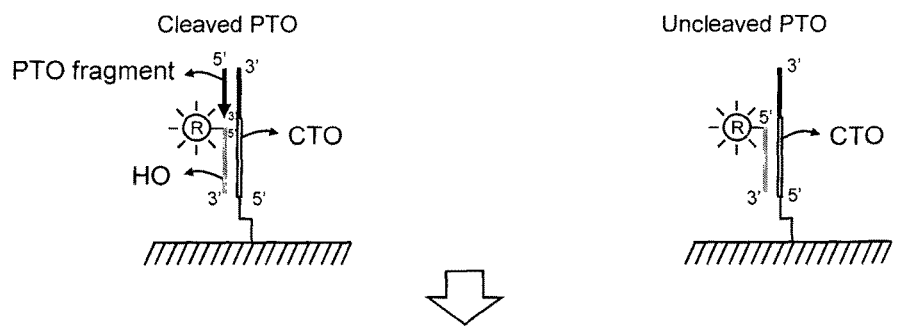
Figure 11:
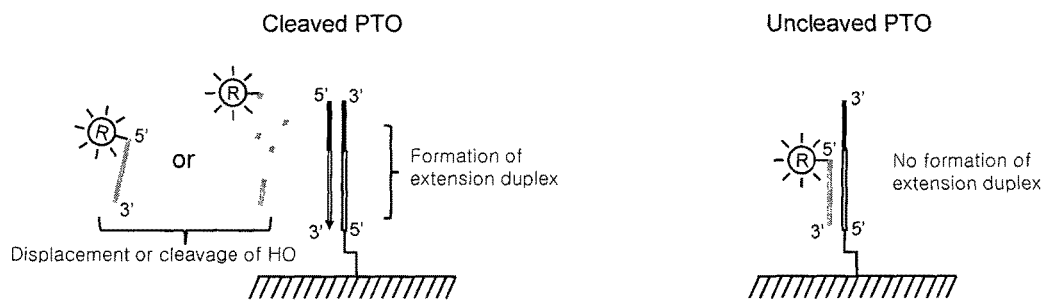
Figure 12:
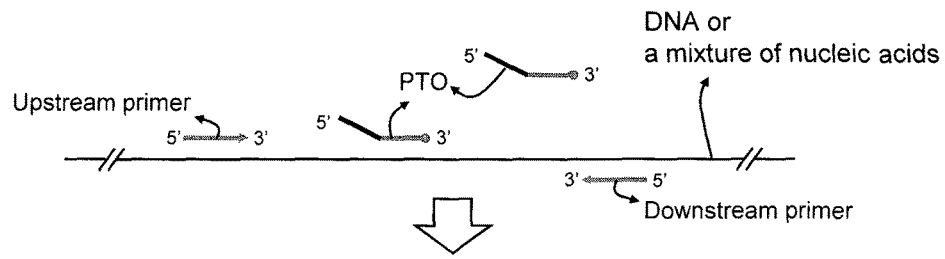
FIGS. 12A, 12B, 12C, and 12D represent schematically the second aspect of PCE-NH assay using a single label on a solid phase.
Figure 12:
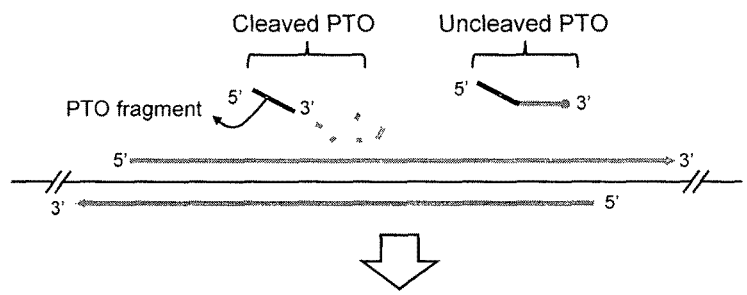
Figure 12:
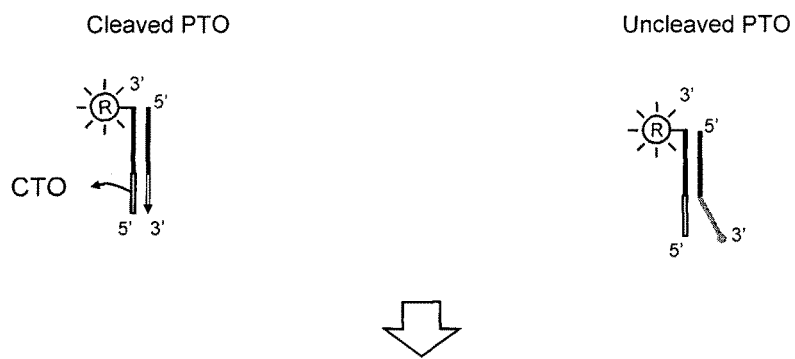
Figure 12:
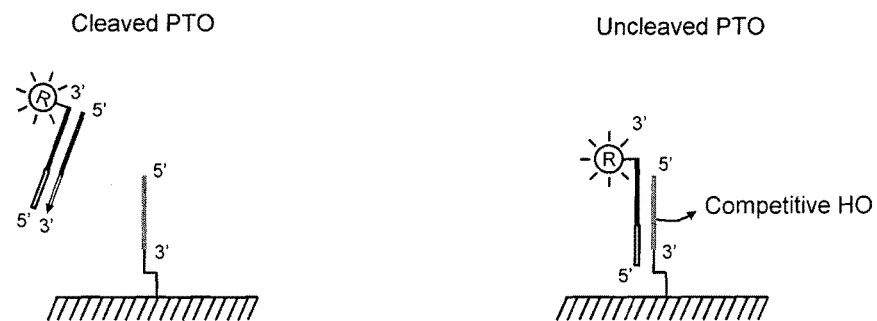
Figure 13:
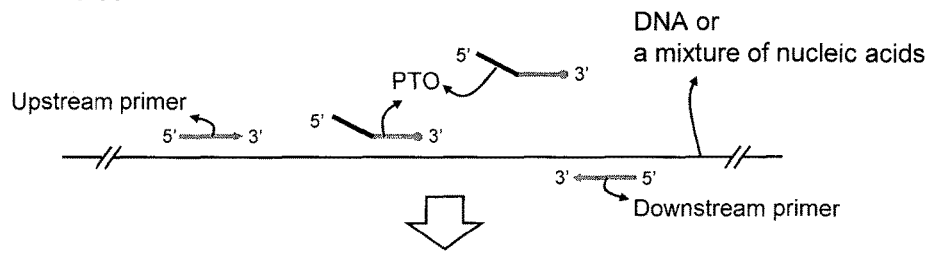
FIGS. 13A, 13B, 13C, and 13D represent schematically the second aspect of PCE-NH assay using a single label on a solid phase.
Figure 13:
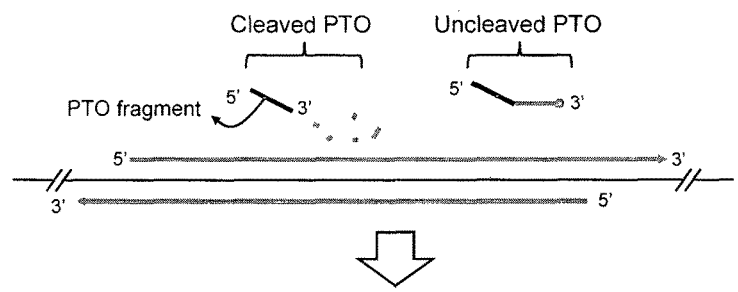
Figure 13:
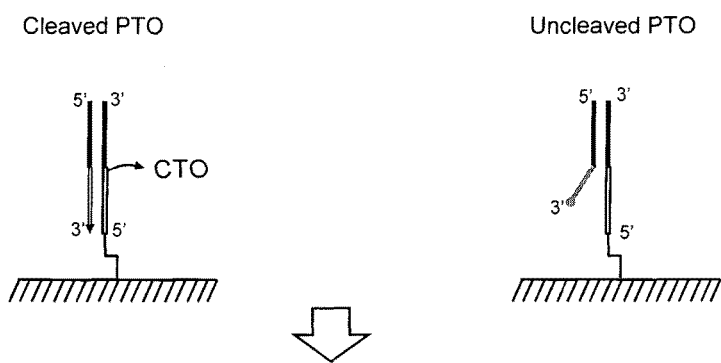
Figure 13:
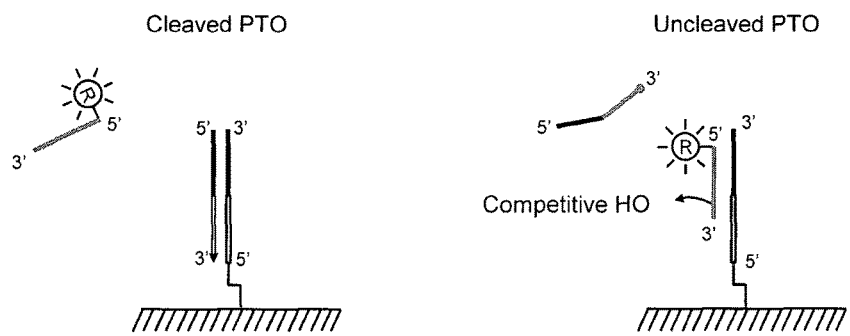

According to an embodiment, the CTO has the single label and the HO is immobilized on the solid substrate or to be immobilized on a solid substrate before the detection of the signal in the step (f) (e.g., FIGS. 8-9 and 12). Alternatively, the HO has the single label and the CTO is immobilized on the solid substrate or to be immobilized on a solid substrate before the detection of the signal in the step (f) (e.g., FIGS. 10-11 and 13).

According to an embodiment, the single label may be any label.

The single label includes, but not limited to, a chemical label (e.g., biotin), an enzymatic label (e.g., alkaline phosphatase, peroxidase, β-galactosidase and β-glucosidase), a radioisotope label (e.g., $I^{125}$ and $C^{14}$), a fluorescent label, a luminescent label, a chemiluminescent label, and a metal label (e.g., gold).

In the present method, the HO or the CTO has a single label; wherein the single label is positioned at a site such that a signal from the single label in the case of the formation of the hybrid between the CTO and the HO is different from a signal from the single label in the case of no formation of the hybrid between the CTO and the HO.

FIG. 8 illustrates the second aspect of this invention using the CTO having a single label and the immobilized HO. Where the target nucleic acid sequence is present in the nucleic acid sample, the extended duplex is formed to prevent the formation of the hybrid between the CTO and the HO, thereby providing no signal from the single label of the CTO on the solid substrate. When the target nucleic acid sequence is not present in the nucleic acid sample, the extended duplex is not formed and the CTO and the HO form the hybrid, thereby providing a signal from the single label of the CTO on the solid substrate.

The details as to the prevention of the hybrid formation between the CTO and the HO by the extended duplex may be also described with reference to descriptions about that for the first aspect of the PCE-NH assay comprising melting or hybridization analysis.

Figure 10:
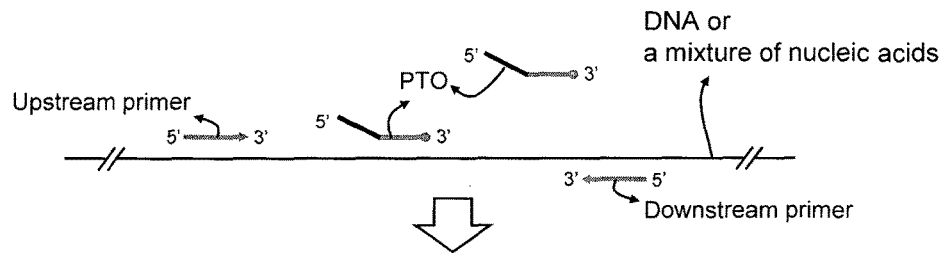
FIGS. 10A, 10B, 10C, and 10D represent schematically the second aspect of PCE-NH assay using a single label on a solid phase.
Figure 10:
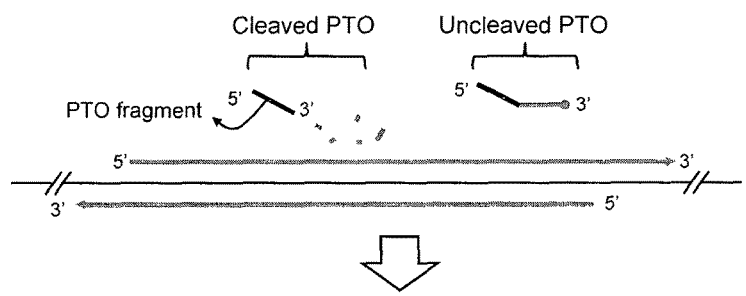
Figure 10:
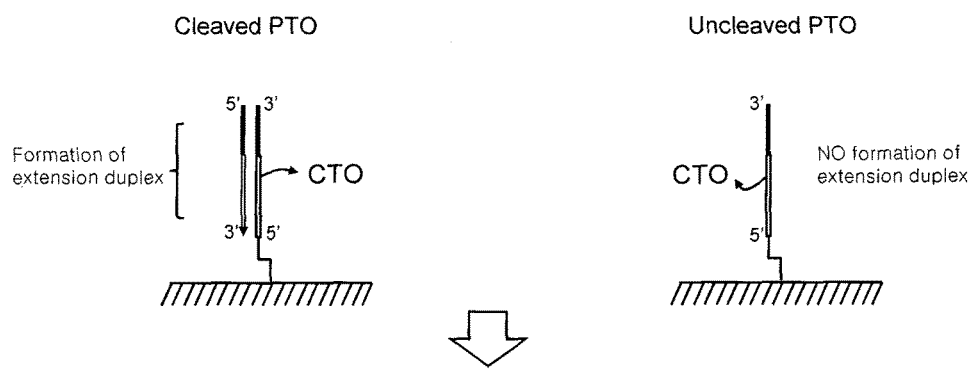
Figure 10:

For example, where the CTO and the HO are first contacted with each other in the step (e) (e.g., performing the steps (a)-(d) and (e)-(f) in separate reaction vessels), the present invention may be carried out as depicted in FIGS. 8 and 10. The HO is not contacted to the CTO prior to the extension of the PTO fragment but involved in hybridization with the resultant of the extension reaction. In the step (e), the formation of the extended duplex prevents the formation of the hybrid of the CTO/HO due to the inhibition of the hybridization of the HO with the CTO.

Where the CTO and the HO are contacted with each other in the step (d) (e.g., performing the steps (a)-(f) in a single reaction vessel), the present invention may be carried out as depicted in FIGS. 9 and 11. The HO may be hybridized with the CTO prior to the extension and involved in the extension reaction. When the HO is hybridized with the CTO prior to the extension of the fragment, the extension of the fragment cleaves or displaces the HO from the CTO. Particularly, where the HO is cleaved during the extension reaction, the formation of the extended duplex prevents the formation of the hybrid of the CTO/HO in the step (e) due to the consumption of the HO by the cleavage.

Even if the CTO and the HO have a chance to be contacted with each other in the step (d), some of the HOs may not be even hybridized with the CTO prior to the extension. In such case, the HOs may not form the hybrid with the CTO in the step (e) due to the inhibition of the hybridization of the HO with the CTO.

Without regard to the step in which the HO is first contacted to the CTO, the extended duplex is formed to prevent the formation of the hybrid between the CTO and the HO in the presence of the target nucleic acid sequence by the following fashions (i) the inhibition of the hybridization of the HO with the CTO and/or (ii) the consumption of the HO by the cleavage.

In the absence of the target nucleic acid sequence, the extended duplex is not formed and the hybrid between the CTO and the HO is therefore formed.

According to an embodiment, the step (d) is performed in the presence of the HOs and the HOs are hybridized with the CTO and/or not hybridized with the CTO. According to an embodiment, the step (d) is performed in the presence of the HOs; wherein (i) the fragment hybridized with the capturing portion of the CTO is extended prior to the hybridization of the HO and/or (ii) when the HO is hybridized with the CTO prior to the extension of the fragment, the extension of the fragment cleaves or displaces the HO from the CTO, thereby the formation of the extended duplex prevents the formation of the hybrid between the CTO and the HO in the step (f) due to the inhibition of the hybridization of the HO with the CTO and/or the consumption of the HO by the cleavage The HO comprises a hybridizing nucleotide sequence complementary to the CTO. The nucleotide sequence of the HO may be designed to comprise a complementary to a region of CTO other than a region to be hybridized with the PTO fragment. In certain embodiment, the HO may be designed to comprise a nucleotide sequence being competitive with the fragment (or uncleaved PTO) in terms of hybridization with the CTO (see FIGS. 12 and 13). Specifically, such competitive HO is not cleaved by the fragment or its extension product.

The details as to the competitive HO may be also described with reference to descriptions about that for the first aspect of the PCE-NH assay comprising melting or hybridization analysis.

According to an embodiment, one of the CTO and HO become immobilized on a solid substrate between the step (d) and the step (e) or between the step (e) and the step (f).

Step (f): Detection of Signal Indicating the Presence of the CTO/HO Hybrid

Finally, the signal on the solid substrate to detect the hybrid between the CTO and the HO on the solid substrate is detected. The presence of the hybrid between the CTO and the HO indicates the absence of the target nucleic acid sequence, and the absence of the hybrid between the CTO and the HO indicates the presence of the target nucleic acid sequence.

According to an embodiment, a signal in the case of the presence of target sequences is different from a signal in the case of the absence of target sequences. Where the target sequence is detected by the present method, such signal difference includes differences in intensity of the signal. In an embodiment, such signal difference is by at least 10%, at least 30%, at least 50%, at least 70% or at least 90%.

The present invention is characterized in that one of the CTO and the HO is labeled with a single label and the other unlabeled is immobilized on a solid substrate or is to become immobilized on a solid substrate before the detection of the signal in the step (f). The approach of the present invention that the signal from the single label is generated on the solid substrate in the absence of the target nucleic acid sequence and the signal from the single label is extinguished or decreased on the solid substrate in the presence of the target nucleic acid sequence becomes practical by such combination of the two oligonucleotides.

According to an embodiment, the detection of the signal on the solid substrate is performed by measuring the signal on the solid substrate at a predetermined temperature wherein the hybrid between the CTO and the HO maintains its double-stranded form.

The detection of the step (f) may be performed in a real-time manner, an end-point manner, or a predetermined time interval manner. Where the present invention further comprises repeating all or some of the steps (a)-(f) with denaturation between repeating cycles, the signal detection may be performed for each cycle of the repetition at a predetermined temperature (i.e. real-time manner), at the end of the repetition at a predetermined temperature (i.e. end-point manner) or at each of predetermined time intervals during the repetition at a predetermined temperature.

According to an embodiment, the detection of the signal on the solid substrate is performed by a melting or hybridization analysis over a range of temperatures. The details of the melting or hybridization analysis may be described with reference to descriptions for the melting or hybridization analysis for the first aspect of the PCE-NH assay comprising melting or hybridization analysis.

The signal detection may be performed in accordance with conventional methods such as benchtop fluorometers, fluorescence multi-well plate readers, fiber optic fluorometers, fluorescence microscopes and microchips/microfluidics systems coupled with fluorescence detection.

According to an embodiment, the method is performed with no use of the upstream oligonucleotide and the cleavage of the PTO in the step (b) occurs with no help of the upstream oligonucleotide or its extended strand. The embodiment using upstream oligonucleotide-independent 5' nuclease activity is described in more detail as follows:

Target Detection by a PCE-NH Assay Based on Upstream Oligonudeotide-Independent 5' Nuclease Activity In further aspect of this invention, there is provided a method for detecting a target nucleic acid sequence in a nucleic acid sample on a solid phase by a PCE-NH (PTO Cleavage and Extension-Dependent Non-Hybridization) assay, comprising:

(a) hybridizing the target nucleic acid sequence with a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO; wherein the PTO hybridized with the target nucleic acid is cleaved by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) hybridizing the resultant of the step (d) with a HO (hybridizing oligonucleotide) comprising a hybridizing nucleotide sequence complementary to the CTO under conditions suitable for hybridization between the CTO and the HO; wherein one of the CTO and the HO is labeled with a single label and the other unlabeled is immobilized on a solid substrate or is to become immobilized on a solid substrate immediately before the detection of the signal in the step (f); wherein when the target nucleic acid sequence is not present in the nucleic acid sample, the extended duplex is not formed and the CTO and the HO form the hybrid, thereby providing a signal from the single label on the solid substrate; wherein when the target nucleic acid sequence is present in the nucleic acid sample, the extended duplex is formed to prevent the formation of the hybrid between the CTO and the HO, thereby providing no signal from the single label on the solid substrate; and (f) detecting the signal on the solid substrate to detect the hybrid between the CTO and the HO on the solid substrate; wherein the presence of the hybrid between the CTO and the HO indicates the absence of the target nucleic acid sequence; wherein the absence of the hybrid between the CTO and the HO indicates the presence of the target nucleic acid sequence.

Since the present method based on upstream oligonucleotide-independent 5' nuclease activity is the same as those by the second aspect of the PCE-NH assay using upstream oligonucleotides except for no use of upstream oligonucleotides, the common descriptions between them are omitted in order to avoid undue redundancy leading to the complexity of this specification.

For the present method, conventional enzymes having upstream oligonucleotide-independent 5' nuclease activity may be used. Among template-dependent polymerases having 5' nuclease activity, there are several enzymes having upstream oligonucleotide-independent 5' nuclease activity, e.g., Taq DNA polymerase.

Kits for Target Detection

In further aspect of this invention, there is provided a kit for detecting a target nucleic acid sequence in a nucleic acid sample on a solid phase by a PCE-NH (PTO Cleavage and Extension-Dependent Non-Hybridization) assay, comprising:

(a) an upstream oligonucleotide; wherein the upstream oligonucleotide comprises a hybridizing nucleotide sequence complementary to the target nucleic acid sequence;

(b) a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed; and (d) a HO (hybridizing oligonucleotide) comprising a hybridizing nucleotide sequence complementary to the CTO;

wherein one of the CTO and the HO is labeled with a single label and the other unlabeled is immobilized on a solid substrate or is to become immobilized on a solid substrate immediately before the detection of a signal from the single label; wherein when the target nucleic acid sequence is present in the nucleic acid sample, the extended duplex is formed to prevent the formation of the hybrid between the CTO and the HO, thereby providing no signal from the single label on the solid substrate; wherein when the target nucleic acid sequence is not present in the nucleic acid sample, the extended duplex is not formed and the CTO and the HO form the hybrid, thereby providing a signal from the single label on the solid substrate.

Since the kit of this invention is constructed to perform the detection method of the present invention described above, the common descriptions between them are omitted in order to avoid undue redundancy leading to the complexity of this specification.

III. Third Aspect of Target Detection Process by a PCE-NH Assay

In another aspect of the present invention, there is provided a method for detecting a target nucleic acid sequence in a nucleic acid sample by a PCE-NH (PTO Cleavage and Extension-Dependent Non-Hybridization) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) hybridizing the resultant of the step (d) with a HO (hybridizing oligonucleotide) comprising a hybridizing nucleotide sequence complementary to the CTO under conditions suitable for hybridization between the CTO and the HO; wherein when the target nucleic acid sequence is not present in the nucleic acid sample, the extended duplex is not formed and the CTO and the HO form a hybrid, thereby providing a first signal indicative of the presence of the hybrid between the CTO and the HO; wherein when the target nucleic acid sequence is present in the nucleic acid sample, the extended duplex inhibits the hybridization of the HO with the CTO, thereby providing a second signal indicative of the presence of HO unhybridized with CTO; wherein the signals are provided by (i) a label linked to the HO, (ii) a label linked to the CTO, (iii) a label linked to the HO and a label linked to the CTO, or (iv) an intercalating label; and (f) detecting the first signal or the second signal at a predetermined temperature at which the hybrid between the CTO and the HO maintains its double-stranded form; wherein the presence of the hybrid between the CTO and the HO indicates the absence of the target nucleic acid sequence; wherein the absence of the hybrid between the CTO and the HO indicates the presence of the target nucleic acid sequence; wherein the difference in the first signal and the second signal allows to determine the presence or absence of the hybrid between the CTO and the HO to indicate the presence or absence of the target nucleic acid sequence in the nucleic acid sample.

The third aspect of this invention is based on PCE-NH (PTO Cleavage and Extension-Dependent Non-Hybridization) approach as the first aspect of this invention. However, the third aspect of this invention is characterized in that it focuses on the phenomenon that the extended duplex in the presence of the target nucleic acid sequence inhibits the hybridization of the HO with the CTO and that a signal is detected at a pre-determined temperature.

The present inventors have found that the formation of the extended duplex induce the inhibition of the hybridization of the HO with the CTO to result in no formation of the CTO/HO hybrid even when the HO is not cleaved, which may be successfully applied to detection of a target nucleic acid sequence. With using the underlying principle, the present invention requires that a signal in the case that the HO is not cleaved to maintain as a single strand form is different from a signal in the case that the HO forms the CTO/HO hybrid.

Because the present invention does not necessarily require the cleavage of the HO in the extension of the PTO fragment, the extension of the PTO fragment (i.e., steps (a)-(d)) and the hybridization between the HO and the CTO and the detection (i.e., steps (e)-(f)) may be performed separately. Where the HO having an interactive dual label is used and a target nucleic acid sequence is present, a signal from the cleavage of the HO shows a differentially different profile from a signal from the inhibition of the intact HO hybridization with the CTO.

The term used herein "inhibit the hybridization of the HO with the CTO" with referring to the extended duplex means that the extended strand in the extended duplex inhibits the binding (or annealing) of the uncleaved or intact HO to the CTO. The term "inhibit the hybridization of the HO with the CTO" may be considered as a restricted embodiment of the term "prevent the formation of the hybrid between the CTO and the HO".

Accordingly, the third aspect of this invention necessarily requires the occurrence of inhibiting the hybridization of the HO with the CTO. As discussed below, such requirement does not exclude the occurrence of preventing the formation of the hybrid between the CTO and the HO by cleavage or displacement of the HO by the extended strand.

The third aspect of the PCE-NH assay will be described in more detail as follows:

Step (a): Hybridization of an Upstream Oligonucleotide and a PTO with a Target Nucleic Acid Sequence The step (a) may be described with reference to descriptions for the step (a) of the first aspect of the PCE-NH assay comprising melting or hybridization analysis.

Step (b): Release of a Fragment from the PTO Cleavage

The step (b) may be described with reference to descriptions for the step (b) of the first aspect of the PCE-NH assay comprising melting or hybridization analysis.

Step (c): Hybridization of the Fragment Released from the PTO with CTO

The step (c) may be described with reference to descriptions for the step (c) of the first aspect of the PCE-NH assay comprising melting or hybridization analysis.

Step (d): Extension of the Fragment

The step (d) may be described with reference to descriptions for the step (d) of the first aspect of the PCE-NH assay comprising melting or hybridization analysis.

Step (e): Hybridization the Extended Duplex with HO

Following the extension reaction, the resultant of the step (d) is hybridized with a HO (hybridizing oligonucleotide) comprising a hybridizing nucleotide sequence complementary to the CTO under conditions suitable for hybridization between the CTO and the HO.

When the target nucleic acid sequence is not present in the nucleic acid sample, the extended duplex is not formed and the CTO and the HO form a hybrid, thereby providing a first signal indicative of the presence of the hybrid between the CTO and the HO. When the target nucleic acid sequence is present in the nucleic acid sample, the extended duplex inhibits the hybridization of the HO with the CTO, thereby providing a second signal indicative of the presence of HO unhybridized with CTO.

The hybridization between the CTO and the HO may occur first in the step (e). Alternatively, the hybridization between the CTO and the HO may occur first in the step (d). In certain embodiment, the step (d) is performed in the presence of the HOs; wherein (i) the fragment hybridized with the capturing portion of the CTO is extended prior to the hybridization of the HO and/or (ii) when the HO is hybridized with the CTO prior to the extension of the fragment, the extension of the fragment cleaves or displaces the HO from the CTO.

The extended duplex is formed to prevent the formation of the hybrid between the CTO and the HO in the presence of the target nucleic acid sequence by the following fashions (i) the inhibition of the hybridization of the HO with the CTO and/or (ii) the consumption of the HO by the cleavage.

The present method is characterized in that it uses the signal change provided by the inhibition of the hybridization of the uncleaved or intact HO with the CTO. In the present invention, the signal provided in the case that the HO is hybridized with the CTO is different from the signal provided in the case that the hybridization of the uncleaved or intact HO with the CTO is inhibited by the extended duplex at the pre-determined temperature suitable for hybridization between the CTO and the HO.

Where the step (d) is performed in the presence of the HOs, some HOs may be cleaved during the extension of the PTO fragment and a signal provided from the cleavage may co-exist.

The details of the HO may be described with reference to descriptions for the HO for the first aspect of the PCE-NH assay comprising melting or hybridization analysis.

The HO comprises a hybridizing nucleotide sequence complementary to the CTO. The nucleotide sequence of the HO may be designed to comprise a complementary to a region of CTO other than a region to be hybridized with the PTO fragment. Alternatively, the HO may comprise a nucleotide sequence being competitive with the fragment in terms of hybridization with the CTO (see FIGS. 17 and 18). Specifically, such competitive HO is not cleaved by the fragment or its extension product.

The first and second signals are provided by (i) a label linked to the HO, (ii) a label linked to the CTO, (iii) a label linked to the HO and a label linked to the CTO, or (iv) an intercalating label.

According to an embodiment of the present invention, as long as a signal provided in the case that the CTO and the HO are associated to form a hybrid is different from a signal provided in the case that the CTO and the HO are dissociated from each other, various types and locations of labels may be adopted in the present invention.

The term used herein "the HO" in conjunction with the expression "the CTO and the HO are dissociated from each other" refers to an uncleaved or intact HO.

Figure 14:
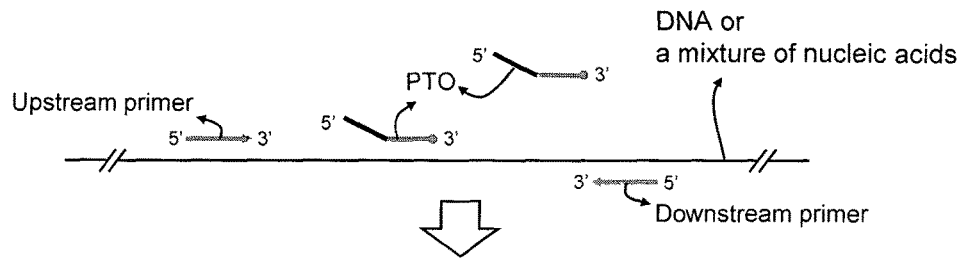
FIGS. 14A, 14B, 14C, and 14D represent schematically the third aspect of PCE-NH assay comprising detection at a pre-determined temperature based on a novel reaction in which the formation of the extended duplex inhibits the hybridization of the HO with the CTO.
Figure 14:
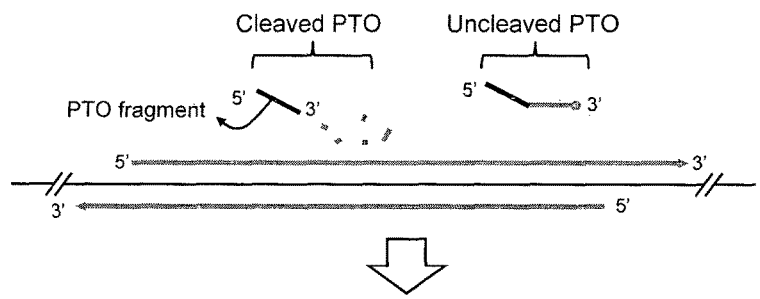
Figure 14:
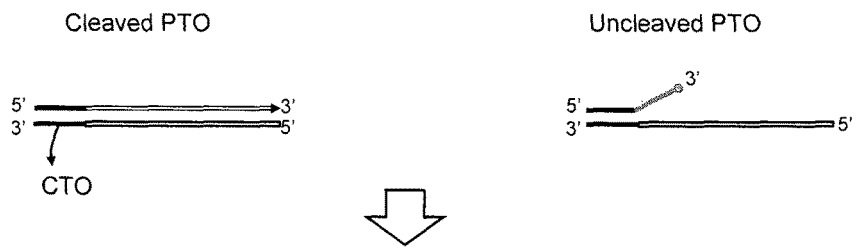
Figure 14:
Figure 17:
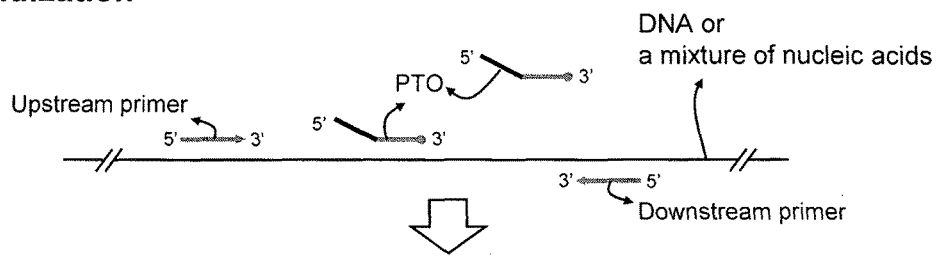
FIGS. 17A, 17B, 17C, and 17D represent schematically the third aspect of PCE-NH assay comprising detection at a pre-determined temperature based on a novel reaction in which the formation of the extended duplex inhibits the hybridization of the HO with the CTO.
Figure 17:
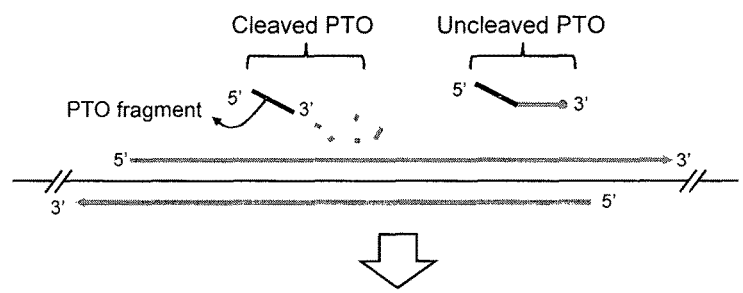
Figure 17:
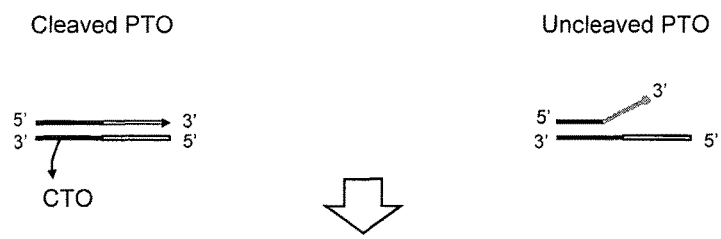
Figure 17:
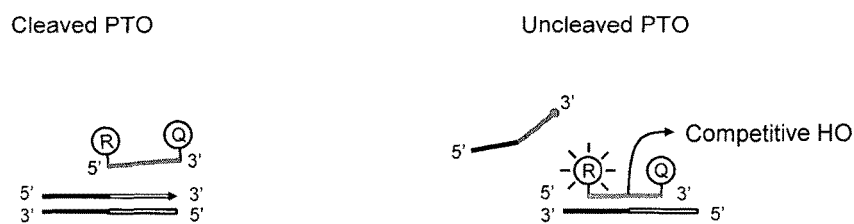

According to an embodiment, the HO or the CTO has an interactive dual label comprising a reporter molecule and a quencher molecule; wherein the interactive dual label is positioned at a site such that a signal from the interactive dual label in the case that the CTO and the HO are associated to form a hybrid is different from a signal from the interactive dual label in the case that the CTO and the HO are dissociated from each other (see FIGS. 14 and 17).

Where the HO having an interactive dual label is used, a signal from the cleavage of the HO shows a differentially different pattern from a signal from the inhibition of the hybridization between the HO and the CTO.

When the HO is in a single stranded state, the reporter molecule and the quencher molecule on the HO are conformationally adjacent to each other to allow the quencher molecule to quench the signal from the reporter molecule. Where the target nucleic acid sequence is absent and the CTO/HO hybrid is formed, the reporter molecule and the quencher molecule on the HO are conformationally separated to allow the quencher molecule to unquench the signal from the reporter molecule.

When the target nucleic acid sequence is present, the target-dependent formation of the extended duplex inhibits the hybridization of the HO with the CTO, thereby enabling the HO to be in a single stranded state, resulting in quenching the to signal form the reporter molecule. The number of the HOs in a single strand is increased upon increasing the number of the extended duplex, and in turn the signal intensity finally detected shows decreased patterns.

Meanwhile, when the target nucleic acid sequence is present, the HO hybridized with the CTO may be cleaved during the extension of the PTO fragment. The cleavage causes the reporter molecule and the quencher molecule to be separated permanently, which results in unquenching perfectly the signal from the reporter molecule. The unquenching extent by cleavage of the HO is larger than the unquenching extent by hybridization of the HO with the CTO. Therefore, where signal provided by cleavage of the HO is detected, the signal intensity shows increased patterns upon increasing the number of the cleaved HOs.

While both situations including the inhibition of hybridization between the intact HO and the CTO and the cleavage of the HO may coexist, the signal pattern may be provided depending on a prevailing situation.

Figure 15:
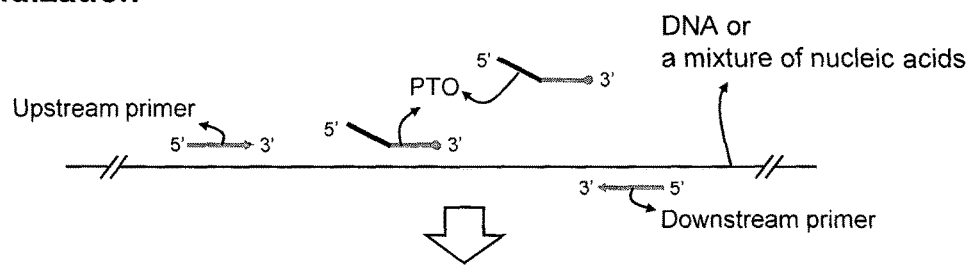
FIGS. 15A, 15B, 15C, and 15D represent schematically the third aspect of PCE-NH assay comprising detection at a pre-determined temperature based on a novel reaction in which the formation of the extended duplex inhibits the hybridization of the HO with the CTO.
Figure 15:
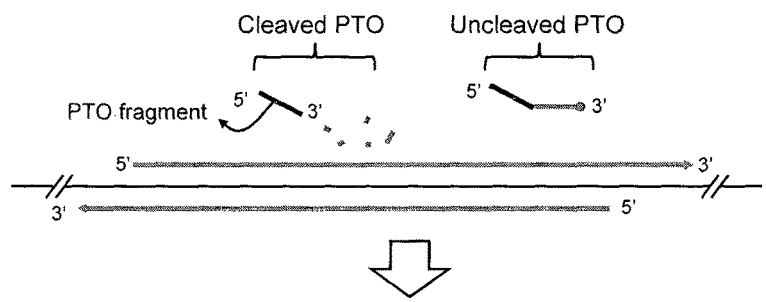
Figure 15:
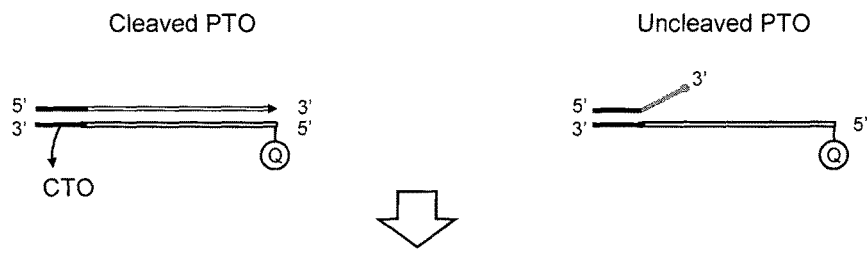
Figure 15:
Figure 18:
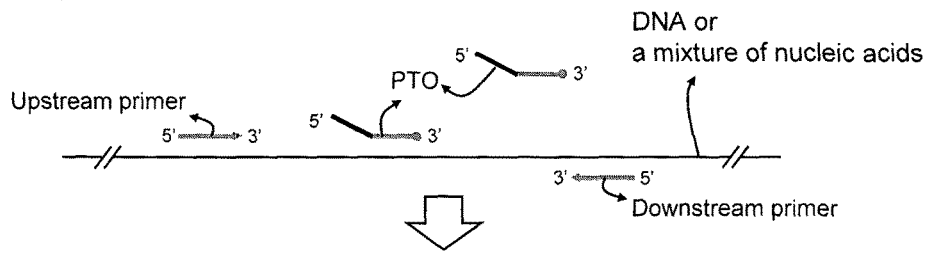
FIGS. 18A, 18B, 18C, and 18D represent schematically the third aspect of PCE-NH assay comprising detection at a pre-determined temperature based on a novel reaction in which the formation of the extended duplex inhibits the hybridization of the HO with the CTO.
Figure 18:
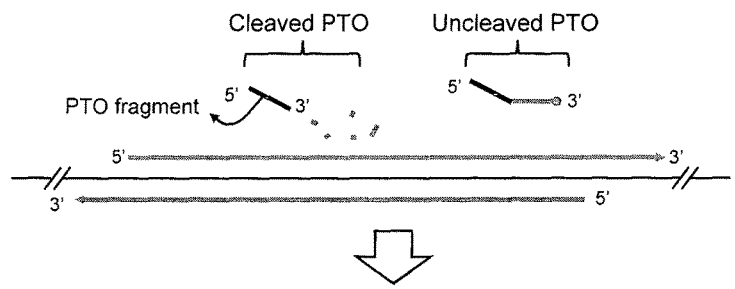
Figure 18:
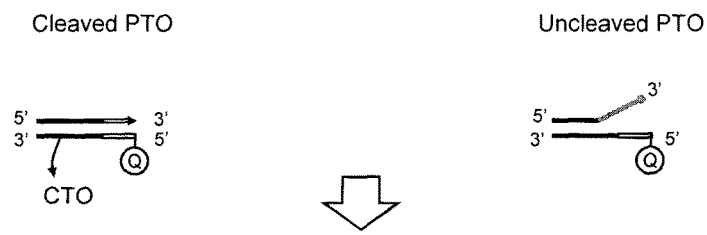
Figure 18:
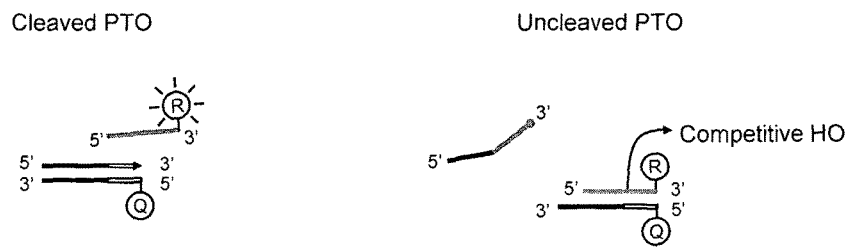

According to an embodiment, the HO has one of an interactive dual label comprising a reporter molecule and a quencher molecule and the CTO has the other of the interactive dual label; wherein the interactive dual label is positioned at a site such that a signal from the interactive dual label in the case that the CTO and the HO are associated to form a hybrid is different from a signal from the interactive dual label in the case that the CTO and the HO are dissociated from each other (see FIGS. 15 and 18).

In certain embodiment, the present method is performed using one additional HO comprising a hybridizing nucleotide sequence complementary to the CTO and the two HOs are hybridized with the CTO in an adjacent manner to each other; wherein one of the two HOs has one of an interactive dual label comprising a reporter molecule and a quencher molecule and the other of the two HOs has the other of the interactive dual label; wherein the interactive dual label is positioned at a site such that a signal from the interactive dual label in the case that the CTO and the two HOs are associated to form a hybrid is different from a signal from the interactive dual label in the case that the CTO and the two HOs are dissociated from each other.

Figure 16:
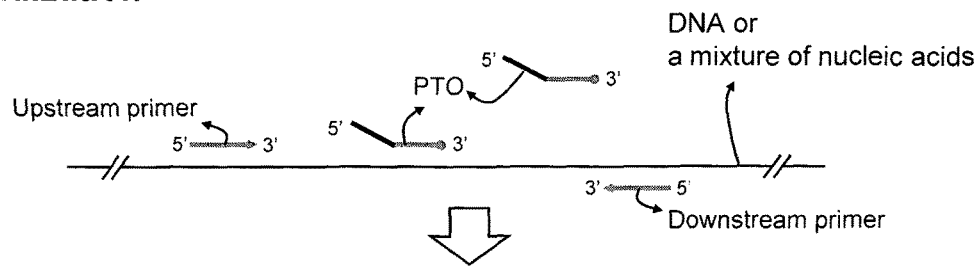
FIGS. 16A, 16B, 16C, and 16D represent schematically the third aspect of PCE-NH assay comprising detection at a pre-determined temperature based on a novel reaction in which the formation of the extended duplex inhibits the hybridization of the HO with the CTO.
Figure 16:
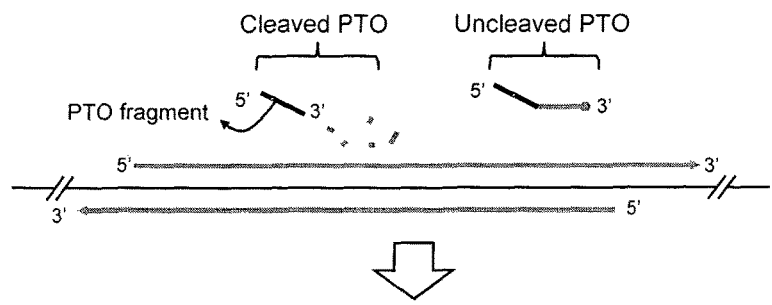
Figure 16:
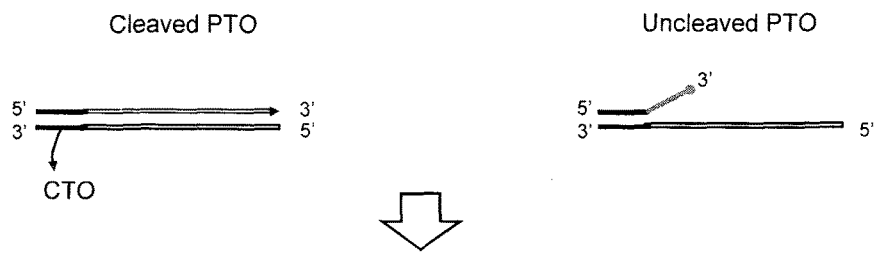
Figure 16:

According to an embodiment, the HO or the CTO has a single label; wherein the single label is positioned at a site such that a signal from the single label in the case that the CTO and the HO are associated to form a hybrid is different from a signal from the single label in the case that the CTO and the HO are dissociated from each other (see FIG. 16).

The details (including signaling mechanism and label positions, and so on) of the labeling systems may be described with reference to descriptions for the labeling systems for the first aspect of the PCE-NH assay comprising melting or hybridization analysis.

Step (f): Detection of the First or Second Signal at a Predetermined Temperature Finally, the first signal or the second signal is detected at a predetermined temperature at which the hybrid between the CTO and the HO maintains its double-stranded form.

The presence of the hybrid between the CTO and the HO indicates the absence of the target nucleic acid sequence and the absence of the hybrid between the CTO and the HO indicates the presence of the target nucleic acid sequence. The difference in the first signal and the second signal allows to determine the presence or absence of the hybrid between the CTO and the HO to indicate the presence or absence of the target nucleic acid sequence in the nucleic acid sample.

According to an embodiment, the first signal and the second signal is discriminated by such a phenomenon as signal generation and signal distinction.

According to an embodiment, the first signal and the second signal is discriminated by such a phenomenon as the change of intensity (signal increase and signal decrease).

According to an embodiment, a signal in the case of the presence of target sequences is different from a signal in the case of the absence of target sequences. Where the target sequence is detected by the present method, such signal difference includes differences in intensity of the signal. In an embodiment, such signal difference is by at least 10%, at least 30%, at least 50%, at least 70% or at least 90%.

The temperature at which the hybrid between the CTO and the HO maintains its double-stranded form may be routinely determined in considering $T_m$ values of the CTO and the HO.

The detection of the step (f) may be performed in a real-time manner, an end-point manner, or a predetermined time interval manner. Where the present invention further comprises repeating all or some of the steps (a)-(f) with denaturation between repeating cycles, the signal detection may be performed for each cycle of the repetition at a predetermined temperature (i.e. real-time manner), at the end of the repetition at a predetermined temperature (i.e. end-point manner) or at each of predetermined time intervals during the repetition at a predetermined temperature.

According to an embodiment, the method is performed using a control group having no target nucleic acid sequence or a predetermined amount of the target nucleic acid sequence.

The present invention may be carried out either in a liquid phase or on a solid phase.

Target Detection on a Solid Phase

According to an embodiment, the present invention is performed on the solid phase, and one of the CTO and HO is immobilized on the solid substrate or to become immobilized on a solid substrate before the detection of the signal in the step (f) and the signal is detected on the solid substrate.

According to an embodiment, one of the CTO and HO become immobilized on a solid substrate between the step (d) and the step (e) or between the step (e) and the step (f).

The details of the target detection on a solid phase for the third aspect will be described with reference to descriptions for the first aspect of the PCE-NH assay comprising melting or hybridization analysis.

According to an embodiment, the method is performed with no use of the upstream oligonucleotide and the cleavage of the PTO in the step (b) occurs with no help of the upstream oligonucleotide or its extended strand. The embodiment using upstream oligonucleotide-independent 5' nuclease activity is described in more detail as follows:

Target Detection by a PCE-NH Assay Based on Upstream Oligonucleotide-Independent 5' Nuclease Activity In further aspect of the present invention, there is provided a method for detecting a target nucleic acid sequence in a nucleic acid sample by a PCE-NH (PTO Cleavage and Extension-Dependent Non-Hybridization) assay, comprising:

(a) hybridizing the target nucleic acid sequence with a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO; wherein the PTO hybridized with the target nucleic acid is cleaved by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) hybridizing the resultant of the step (d) with a HO (hybridizing oligonucleotide) comprising a hybridizing nucleotide sequence complementary to the CTO under conditions suitable for hybridization between the CTO and the HO; wherein when the target nucleic acid sequence is not present in the nucleic acid sample, the extended duplex is not formed and the CTO and the HO form a hybrid, thereby providing a first signal indicative of the presence of the hybrid between the CTO and the HO; wherein when the target nucleic acid sequence is present in the nucleic acid sample, the extended duplex inhibits the hybridization of the HO with the CTO, thereby providing a second signal indicative of the presence of HO unhybridized with CTO; wherein the signals are provided by (i) a label linked to the HO, (ii) a label linked to the CTO, (iii) a label linked to the HO and a label linked to the CTO, or (iv) an intercalating label; and (f) detecting the first signal or the second signal at a predetermined temperature at which the hybrid between the CTO and the HO maintains its double-stranded form; wherein the presence of the hybrid between the CTO and the HO indicates the absence of the target nucleic acid sequence; wherein the absence of the hybrid between the CTO and the HO indicates the presence of the target nucleic acid sequence; wherein the difference in the first signal and the second signal allows to determine the presence or absence of the hybrid between the CTO and the HO to indicate the presence or absence of the target nucleic acid sequence in the nucleic acid sample.

Since the present method based on upstream oligonucleotide-independent 5' nuclease activity is the same as the third aspect of the PCE-NH assay using upstream oligonucleotides except for no use of upstream oligonucleotides, the common descriptions between them are omitted in order to avoid undue redundancy leading to the complexity of this specification.

Kit for Target Detection

In still another aspect of this invention, there is provided a kit for detecting a target nucleic acid sequence in a nucleic acid sample by a PCE-NH (PTO Cleavage and Extension-Dependent Non-Hybridization) assay, comprising:

(a) an upstream oligonucleotide; wherein the upstream oligonucleotide comprises a hybridizing nucleotide sequence complementary to the target nucleic acid sequence;

(b) a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO;

wherein the fragment released from the PTO is hybridized with the capturing portion of the CTO; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed; and (d) a HO (hybridizing oligonucleotide) comprising a hybridizing nucleotide sequence complementary to the CTO;

wherein when the target nucleic acid sequence is not present in the nucleic acid sample, the extended duplex is not formed and the CTO and the HO form a hybrid, thereby providing a first signal indicative of the presence of the hybrid between the CTO and the HO; wherein when the target nucleic acid sequence is present in the nucleic acid sample, the extended duplex inhibits the hybridization of the HO with the CTO, thereby providing a second signal indicative of the presence of HO unhybridized with CTO; wherein the kit further comprises (i) a label linked to the HO, (ii) a label linked to the CTO, (iii) a label linked to the HO and a label linked to the CTO, or (iv) an intercalating label.

Common Descriptions for the Present Inventions

The common descriptions for the first, second and third aspects of the present invention are described as follows:

The primer, PTO, CTO and HO may be comprised of naturally occurring dNMPs and/or NMPs. Alternatively, the primer, PTO, CTO and HO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The primer, PTO, CTO and HO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the CTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the CTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the CTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the CTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the CTO. The strategies using universal bases and degenerate sequences in the CTO ensure to use one type or minimal types of the CTO for screening multiple target nucleic acid sequences.

According to an embodiment, the present method further comprises repeating all or some of the steps (a)-(f) with denaturation between repeating cycles. This repetition permits to amplify the target nucleic acid sequence and/or the target signal. According to an embodiment, the steps (a)-(b), (a)-(d) or (a)-(f) may be repeated with denaturation. In certain embodiment, the number of the repeating cycles may be optionally adjusted. The denaturation may be carried out by conventional technologies, including, but not limited to, heating, alkali, formamide, urea and glycoxal treatment, enzymatic methods (e.g., helicase action), and binding proteins. For instance, the melting can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

According to an embodiment, the steps (a)-(f) are performed in a reaction vessel or in separate reaction vessels. For example, the steps (a)-(b), (c)-(d) and (e)-(f) may be performed in a single reaction vessel or separate reaction vessels. For example, where the sequences of the PTO and CTO, and the reaction conditions are determined such that the hybridization between the 3'-targeting portion of the PTO and the target nucleic acid sequence may be performed under higher stringent conditions than the hybridization between the PTO fragment and the CTO, the steps (a)-(b) may be repeated with no undertaking the steps (c)-(f). Following the repetition of the steps (a)-(b), the steps (c)-(f) may be performed.

In certain embodiment, the steps (a)-(d) and (e)-(f) may be performed in separate reaction vessels.

In certain embodiment, the steps (a)-(b) may be repeated with denaturation.

It would be appreciated by one of skill in the art that repetition of certain steps, intervention of denaturation in repetition, separate performance of certain step(s) and time point of detection may be widely varied.

According to an embodiment, where the repetition is performed with denaturation using the upstream primer to the PTO, the repetition is carried out in the presence of a downstream primer, particularly according to PCR. The use of the upstream primer and downstream primer to the PTO can amplify the target nucleic acid sequence.

According to an embodiment, where the repetition is performed with denaturation using the upstream probe to the PTO, the repetition is carried out in the presence of a downstream primer to the PTO.

The term used herein "nucleic acid sample" refers to a non-biological sample (e.g., food, water, air, soil and waste) or biological sample containing nucleic acid molecules. The biological sample may be derived from animal, plant, human, fungus, bacterium and virus. The biological sample may be cell, tissue, or fluid from a biological source, blood, plasma, serum, serum, plasma, lymph, milk, urine, faeces, ocular fluid, saliva, semen, brain extracts, spinal cord fluid, appendix, spleen and tonsillar tissue extracts.

The present invention does not require that target nucleic acid sequences to be detected and/or amplified have any particular sequence or length, including any DNA (gDNA and cDNA) and RNA molecules. The target nucleic acid sequence may be in a single- or double-strand.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The target nucleic acid sequence to be detected by the present invention includes a wide variety of nucleic acid sequences, e.g., sequences in a genome, artificially isolated or fragmented sequences and synthesized sequences (e.g., cDNA sequences and barcode sequences). For instance, the target nucleic acid sequence includes nucleic acid marker sequences for Immuno-PCR (IPCR). IPCR employs conjugates between nucleic acid marker sequences and antibodies together with PCR, which is widely applied for detecting various types of targets including proteins (see Sano et al., Science 258 pp:120-122(1992), U.S. Pat. No. 5,665,539, Niemeyer et al., Trends in Biotechnology 23 pp:208-216 (2005), U.S. Pat. Pub. No. 2005/0239108 and Ye et al., Journal of Environmental Science 22 pp:796-800(2010)).

The target nucleic acid molecule of the present invention includes nucleic acid markers as used in IPCR method and the present invention may be applied to detect nucleic acid markers in IPCR method.

The present invention is also useful in detection of a nucleotide variation. Preferably, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to an embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. The resultant PTO fragment is hybridized with the CTO and extended, and the nucleic acid molecule is produced to provide the target signal. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the target signal.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the CTO and extended to form the extended duplex that prevents the formation of the hybrid between the CTO and the HO, thereby not providing the signal indicative of the presence of the CTO/HO hybrid. While, under the controlled conditions, the PTO is not hybridized with a mismatching template having non-complementary sequence in the nucleotide variation position and not cleaved. Preferably, in this case, the complementary sequence to the nucleotide variation in the PTO is positioned at its middle of the 3'-targeting portion of the PTO.

According to an embodiment, the use of an artificial mismatch nucleotide enhances discrimination potential of the PTO to nucleotide variations.

Alternatively, the present invention uses the PTO having the nucleotide variation discrimination site positioned on the 5'-end part of the 3'-targeting portion for selectivity of the PTO to a specific nucleotide variation. The 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence.

Where the PTO is hybridized with the target nucleic acid sequence (i.e., match template) having the nucleotide variation complementary to the nucleotide variation discrimination site, the 5'-end part of the 3'-targeting portion forms a double strand with the match template; however, where the PTO is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

The term used herein "nucleotide variation discrimination site" with reference to the PTO is a complementary sequence on the 5'-end part of the 3'-targeting portion of the PTO to a nucleotide variation in a target nucleic acid sequence.

According to a preferred embodiment, the nucleotide variation discrimination site is located within 10 nucleotides, more preferably 8 nucleotides, still more preferably 6 nucleotides, still much more preferably 4 nucleotides, 3 nucleotides, 2 nucleotides or 1 nucleotide apart from the 5'-end of the 3'-targeting portion of the PTO. Preferably, the nucleotide variation discrimination site is located at the 5'-end of the 3'-targeting portion of the PTO.

The term "site" with reference to either nucleotide variation discrimination site of probes or nucleotide variation site on target sequences is used herein to encompass not only a single nucleotide but also a plurality of nucleotides.

It is noteworthy that such distinct hybridization patterns on the nucleotide variation of interest are responsible for differences in initial cleavage sites of the PTO, thereby producing two types of PTO fragments to give signal differentiation depending on the presence of the nucleotide variation of interest.

In the presence of the nucleotide variation of interest, a first fragment is generated by cleavage of hybrid between the PTO and matching template, and in the absence of the nucleotide variation of interest, a second fragment is generate by cleavage of hybrid between the PTO and mismatching template. The second fragment comprises an additional 3'-end portion rendering the second fragment to be different from the first fragment.

In an embodiment for the detection of a single nucleotide variation, the 5'-end of the 3'-targeting portion of the PTO has a complementary sequence to the single nucleotide variation in a target nucleic acid sequence. As described above, the cleavage of the PTO hybridized with a matching template may be induced at a site immediately adjacent in a 3'-direction to the 5'-end of the 3'-targeting portion of the PTO, for example, under upstream primer extension-dependent cleavage induction. The 3'-end of the PTO fragment has the complementary nucleotide to the single nucleotide variation. The PTO fragment is hybridized with a CTO having a capturing portion comprising a sequence corresponding to the nucleotide variation and then extended to form the extended duplex that prevents the formation of the hybrid between the CTO and the HO, thereby not providing the signal indicative of the presence of the CTO/HO hybrid. If the same PTO is hybridized with a mismatching template having the identical sequence to the matching template except for the single nucleotide variation, the cleavage of the PTO may occur at a site two nucleotides apart in a 3'-direction from the 5'-end of the 3'-targeting portion of the PTO. The 3'-end of the PTO fragment has the further cleaved nucleotide than the complementary nucleotide to the single nucleotide variation. Where the site of the CTO hybridized with the additional-cleaved nucleotide is designed to have a non-complementary sequence to the further cleaved nucleotide, the 3'-end of the PTO fragment is not hybridized with the CTO, resulting in no extension of the PTO fragment in a controlled condition.

According to an embodiment, a cleavage site of the PTO having a complementary sequence to the nucleotide variation at its 5'-end part of the 3'-targeting portion is different depending on hybridization with a matching template or with a mismatching template, such that the PTO fragment released from either hybridization event has different sequence preferably, in its 3'-end part, more preferably, in its 3'-end.

According to an embodiment, the selection of the nucleotide sequence of CTO in consideration of the difference in 3'-end parts of the PTO fragments allows to discriminate the matching template from the mismatching template.

According to an embodiment, the production of either the PTO fragments may be distinctly detected by an extension reaction on the CTO.

According to an embodiment, the CTO has a sequence selected such that the CTO is not hybridized with the additional 3'-end portion of the second fragment to prevent the second fragment from extension when the second fragment is hybridized with the capturing portion of the CTO.

As described above, the extension of the first fragment is detected by non-hybridization with the HO due to the formation of the extended duplex.

According to an embodiment, the 5'-end part of the 3'-targeting portion of the PTO comprises a non-base pairing moiety located within 1-10 nucleotides (more preferably 1-5 nucleotides) apart from the nucleotide variation discrimination site.

The non-base pairing moiety prevents the 5'-end part of the 3'-targeting portion from formation of a double strand with the target nucleotide sequence when the PTO is hybridized with the target nucleic acid sequence having the nucleotide variation non-complementary to the variation discrimination site.

The use of the non-base pairing moiety (e.g., artificial mismatch nucleotide) enhances discrimination potential of the PTO to nucleotide variations.

According to an embodiment, the non-base pairing moiety does not inhibit the formation of a double strand between the 5'-end part and the target nucleic acid sequence when the PTO is hybridized with the target nucleic acid sequence having the nucleotide variation complementary to the nucleotide variation discrimination site.

According to an embodiment, the non-base pairing moiety widens the distance between the initial cleavage site on the hybrid of the PTO and the matching template and the initial cleavage site on the hybrid of the PTO and the mismatching template.

According to an embodiment, the introduction of a non-base paring moiety sequence enables the initial cleavage site to be adjusted, particularly the initial cleavage site on the hybrid of the PTO and the mismatching template.

According to an embodiment, the non-base pairing moiety is located downstream of the nucleotide variation discrimination site.

The non-base pairing moiety includes any moieties not forming a base pair between target nucleic acid sequences. Preferably, the non-base pairing moiety is (i) a nucleotide comprising an artificial mismatch base, a natural/non-natural base incapable of base-pairing, a base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PTO.

As base pairs containing universal bases such as deoxyinosine, 1-(2'-deoxy-beta-D-ribofuranosyl)-3-nitropyrrole and 5-nitroindole have a lower binding strength than those between natural bases, universal bases may be employed as non-base pairing moieties under certain hybridization conditions.

The non-base pairing moiety introduced into the 5'-end part has preferably 1-10, more preferably 1-5, still more preferably 1-2 moieties. A plurality of non-base pairing moieties in the 5'-end part may be present in a consecutive or intermittent manner. Preferably, the non-base pairing moiety has 2-5 consecutive moieties.

Preferably, the non-base pairing moiety is a non-base pairing chemical compound.

According to an embodiment, the nucleotide variation discrimination site and the non-base pairing moiety of the PTO are located within 10 nucleotides (more preferably 8 nucleotides, 7 nucleotides, 6 nucleotides, 5 nucleotides, 4 nucleotides, 3 nucleotides, 2 nucleotides or 1 nucleotide, still more preferably 1 nucleotide) apart from the 5'-end of the 3'-targeting portion.

According to an embodiment, the PTO has a blocker portion containing as a blocker at least one nucleotide resistant to cleavage by the enzyme having 5' nuclease activity and the blocker portion is positioned to control the initial cleavage site or prevent the cleavage at a site or sites.

For improving detection efficiency of nucleotide variations, the present invention may be performed with the clamping method. The representative clamping method using PNA is disclosed in Henrik et al., *Nucleic Acid Research* 21:5332-5336(1993) and Luo et al., *Nucleic Acid Research* Vol. 34, No 2 e12 (2006).

For instance, the clamping technology using PNA allows to amplify a nucleic acid sequence having a mutant type nucleotide variation but not to amplify a nucleic acid sequence having a wild type nucleotide variation, which is followed by the method disclosed herein, enabling more efficient detection of nucleotide variations. In particular, since the clamping technology permits to amplify only a nucleic acid sequence having a specific-typed nucleotide variation, its combination with the present method would allow for minority-variant detection in a more efficient manner.

In the present invention, the term "amplification blocker" means an oligonucleotide used for clamping.

In general, the amplification blockers for clamping are hybridized only with templates having perfectly complementary sequence to the amplification blockers under the same condition, which are designed not to be hybridized with templates having even single mismatch. The template hybridized with the amplification blocker inhibiting primer annealing or chain elongation is not amplified and only that not hybridized with the amplification blocker is amplified. Nucleic acid analogues such as PNA and LNA are useful as amplification blockers in the senses that they show significant $T_m$ differences for even a single base difference.

According to an embodiment, the amplification blocker is further used in the present invention particularly for minority-variant detection. According to an embodiment, the amplification blocker prevents the extension of the primer located upstream of the amplification blocker. According to an embodiment, the amplification blocker and PTO used may be designed to be hybridized with the same strand in a double strand or different strands from each other. According to an embodiment, an amplification blocker comprises nucleosides/nucleotides having a backbone resistant to the 5' nuclease activity. According to an embodiment, the amplification blocker comprises peptide nucleic acid (PNA), locked nucleic acid (LNA), Morpholino, glycol nucleic acid (GNA), threose nucleic acid (TNA), bridged nucleic acids (BNA), N3'-P5' phosphoramidate (NP) oligomers, minor groove binder-linked-oligonucleotides (MGB-linked oligonucleotides), phosphorothioate (PS) oligomers, $C_1$-$C_4$ alkylphosphonate oligomers, phosphoramidates, β-phosphodiester oligonucleotides, α-phosphodiester oligonucleotides or combination thereof.

Where a probe having at its 5'-end portion a nucleotide variation discrimination portion is hybridized with a mismatch temple, its 5'-end portion may form a single strand under a certain condition. The probe may correspond to a PTO. The signal may be generated by PTO assay of the present invention. This approach may be useful in detection of a target nucleic acid sequence having a nucleotide variation non-complementary to the nucleotide variation discrimination site of probes.

According to an embodiment, the target nucleic acid sequence used in the present invention is a pre-amplified nucleic acid sequence. The utilization of the pre-amplified nucleic acid sequence permits to significantly increase the sensitivity and specificity of target detection of the present invention.

According to an embodiment, the method is performed in the presence of a downstream primer to the PTO.

The advantages of the present invention may be highlighted in the simultaneous (multiplex) detection of at least two target nucleic acid sequences.

According to an embodiment, the method is performed to detect at least two types (more specifically, at least three types, still more specifically at least five types) of target nucleic acid sequences.

According to an embodiment, the method is performed to detect at least two types (more specifically, at least three types, still more specifically at least five types) of target nucleic acid sequences; wherein the upstream oligonucleotide comprises at least two types (more specifically at least three types, still more specifically at least five types) of oligonucleotides, the PTO comprises at least two types (more specifically at least three types, still more specifically at least five types) of the PTOs, the CTO comprises at least two types (specifically at least three types, more specifically at least five types) of the CTO, and the HO comprises at least two types (specifically at least three types, more specifically at least five types) of the HO.

In certain embodiment, when the at least two types of target nucleic acid sequences are present, their corresponding at least two types of signals are provided.

According to an embodiment, the present invention is performed using at least two types of downstream primers to the PTO.

It is also possible to provide additional fragments extendible on the CTO for enhancing the number of the extended strands by an additional 5' nuclease cleavage reaction using an additional PTO which comprises (i) a 3'-targeting portion comprising a hybridizing nucleotide sequence complementary to the extended strand and (ii) a 5'-tagging portion comprising a nucleotide sequence non-complementary to the extended strand but complementary to the capturing portion of the CTO. It is possible to use an additional upstream oligonucleotide comprising a hybridizing nucleotide sequence complementary to the extended strand and being located upstream of the additional PTO for 5' nuclease cleavage reaction. According to an embodiment, the HO may play a role as the additional PTO.

The above preferable embodiment has the feature that the formation of the additional fragments is dependent on the formation of an extended strand.

Alternatively, the additional fragments can be provided by using an additional PTO which comprises (i) a 3'-targeting portion comprising a hybridizing nucleotide sequence complementary to the CTO and (ii) a 5'-tagging portion comprising a nucleotide sequence non-complementary to the CTO but complementary to the capturing portion of the CTO.

According to an embodiment, additional extended duplexes are formed by additional production of the extended strands, contributing to amplification of the target signal.

The features and advantages of this invention will be summarized as follows:

(a) For determination of the presence of target sequences, the present invention employs (i) the PTO to be hybridized with target sequences, (ii) the CTO capable of forming the extended duplex in a target-dependent manner and (iii) the HO to be hybridized with the CTO, thereby dramatically increasing the specificity to target sequences. In addition, conditions for signal generation may be adjusted irrespective of target sequences and therefore reaction conditions for the present methods may be readily established. Such feature permits not only to easily determine conditions for signal generation but also to prevent false positive signals in multiplex target detection in samples, inter alia, versatile clinical samples.

(b) The $T_m$ value of the hybrid between the CTO and the HO may be adjustable by a sequence and/or length of the HO and therefore may be arbitrarily pre-determined. By using such feature, (i) the distinguishable $T_m$ value of the CTO/HO hybrid may be served as a discriminating factor for the presence of the CTO/HO hybrid (e.g., in a melting analysis); and (ii) the detection temperatures for maintaining the CTO/HO hybrid and reaction conditions for multiplex detection of at least two target sequences may be easily determined.

(c) The present invention adopts the occurrence of the inhibition of the hybridization between the intact HO with the CTO by the formation of the target-dependent extended duplex. Therefore, the present invention may detect target sequences even when the HO is not cleaved. In this regard, the detection of the hybrid between the CTO and the HO may be performed in a different vessel from that for the extension of the CTO.

(d) The first and third aspects of the present invention utilize the inhibition of the hybridization between the intact HO with the CTO as well as the cleavage of the HO. Therefore, the design of the 5'-tagging portion of PTO, CTO and HO sequences may be readily performed and the conditions for reactions may be also easily established.

(e) The first and third aspects of the present invention may utilize various labels to detect target sequences.

(f) In the first aspect of the present invention for detection of at least two target sequences, where the hybrids between the CTOs and the HOs have different $T_m$ values from each other, at least two target nucleic acid sequences may be detected by melting curve analysis even using a labeling system providing signals with the same fluorescence characteristics. The advantage permits to be free from limitations associated with the number of detectable fluorescence labels in multiplex real-time detection.

(g) Conventional technologies in which hybrids between probes and target sequences, or PCR amplicons of target sequences are analyzed by melting analysis are very likely to show analysis deviations in nucleotide variation-susceptible samples such as clinical samples. However, the first aspect of the present invention uses the CTO and the HO whose sequences may be designed irrelevant to sequences of targets and thus may yield analysis results with no deviations to samples.

(h) The conventional solid phase reactions to detect target sequences by direct hybridization between immobilized oligonucleotides and target sequences may fail to show efficient reaction results due to restricted solid-phase environment. In contrast, the present invention uses hybridization between the CTO and the HO on solid phase with no involvement of target sequences, such that even general reaction conditions may show more efficient reaction results.

(i) In the solid phase reaction of the present invention, at least two target sequences may detect simultaneously even using a single label.

(j) Where the HO comprises a nucleotide sequence being competitive with the fragment in terms of hybridization with the CTO, its cleavage may be substantially excluded. In such case, the detection of target sequences may be carried out with no influence of the HO cleavage.

(k) Where the HO comprises a nucleotide sequence being competitive with the fragment in terms of hybridization with the CTO, the PTO is more likely to hybridize with a target sequence rather than the CTO in a single reaction vessel because the HO inhibits the binding of the PTO to the CTO.

(l) In an embodiment using the HO comprising a nucleotide sequence being competitive with the fragment in terms of hybridization with the CTO, relatively short CTO may be used, which improves synthesis efficiency and cost effectiveness of the CTO.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of the Effect of the Extended Duplex Formation on the Hybridization of HO to CTO We examined whether the hybridization of Hybridizing Oligonucleotide (HO) to CTO is reduced by increasing the number of the extended duplexes, which indicates that the formation of the extended duplex inhibits the hybridization between HO and CTO. A synthetic extended strand (Syn-ES) having a nucleotide sequence complementary to CTO was prepared to control the amount of the extended duplex and a various amount of Syn-ES was used to form the extended duplex with a fixed amount of CTO.

Syn-ES and CTO have no label. CTO is blocked with a carbon spacer at its 3'-end. HO has a fluorescent reporter molecule (Cal Fluor Red 610) at its 5'-end and has a quencher molecule (BHQ-2) at its 3'-end.

In this Example, the presence of the CTO-HO hybrid was detected by melting analysis.

The sequences of Syn-ES, CTO and HO used in this Example are:

```
NG-Syn-ES
                                    (SEQ ID NO: 1)
5'-ACGACGGCTTGGCTGAGCGCTGGATACCCTGGACGATATG-3'

NG-CTO-1
                                    (SEQ ID NO: 2)
5'-CATATCGTCCAGGGTATCCAGCGCTCAGCCAAGCCGTCG

T[Spacer C3]-3'

NG-HO-1
                                    (SEQ ID NO: 3)
5'-[Cal Fluor Red 610]GCGCTGGATACCCTG[BHQ-2]-3'
```

The reaction was conducted in the final volume of 20 µl containing an amount of Syn-ES (3, 2, 1, 0.5, 0.1 or 0 pmole) (SEQ ID NO: 1), 1 pmole of CTO (SEQ ID NO: 2), 1 pmole of HO (SEQ ID NO: 3) and 10 µl of 2× Master Mix [containing 2.5 mM $MgCl_2$, 200 µM of dNTPs and 1.6 units of H-Taq DNA polymerase (Solgent, Korea)]; the tube containing the reaction mixture was placed in the real-time thermocycler (CFX96, Bio-Rad); and the reaction mixture was denatured for 15 min at 95° C. After the denaturation, a melting curve was obtained by cooling the reaction mixture to 40° C., holding at 40° C. for 10 min, and heating slowly at 40° C. to 85° C. The fluorescence was measured continuously during the temperature rise to monitor dissociation of the CTO-HO hybrid. Melting peak was derived from the melting curve data.

Figure 19A:
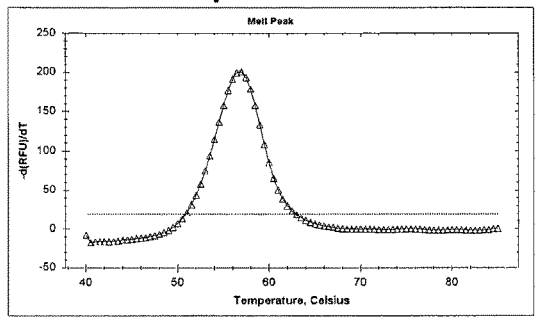
Figure 19A:
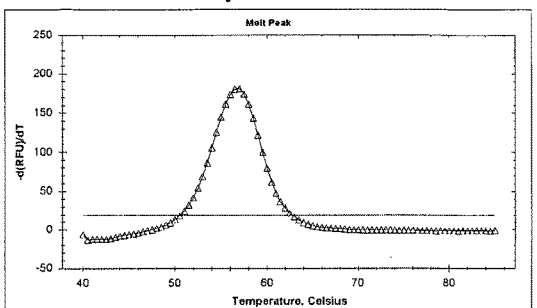
Figure 19A:
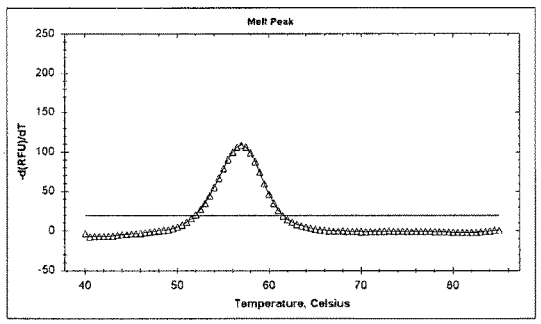
Figure 19A:
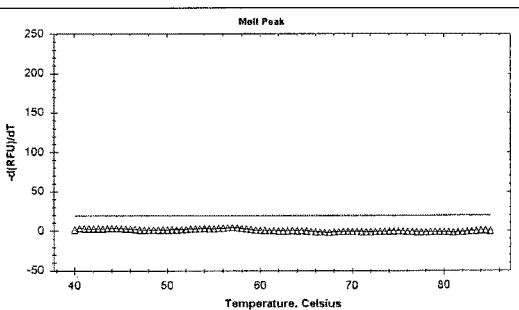
Figure 19A:
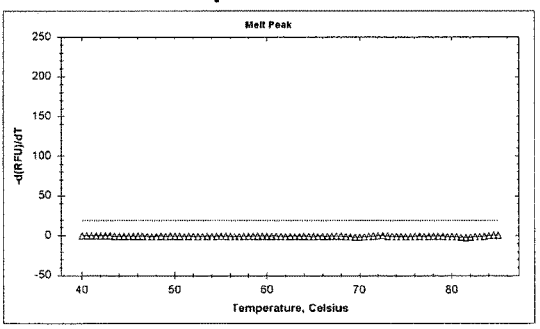
Figure 19A:
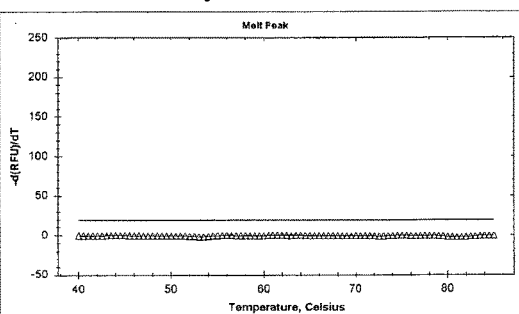

As shown in FIGS. 19A and 19B, in the range of 0~0.5 pmole of Syn-ES, melting peaks at 57.0° C. corresponding to the expected Tm value of the CTO-HO hybrid were detected and the heights of them were decreased inverse proportionally to the amount of Syn-ES. No peaks were detected when Syn-ES was used over 1 pmole.

This result shows that the hybridization of HO to CTO is reduced as the extended duplex forms, which indicates that the formation of the extended duplex inhibits the hybridization between HO and CTO.

Example 2: Detection of a Target Nucleic Acid Sequence Using PCE-NH Assay

We further examined whether PCE-NH assay can detect a target nucleic acid sequence in (i) real-time detection at a pre-determined temperature or (ii) melting analysis manner.

Taq DNA polymerase having a 5' nuclease activity was used for the extension of the upstream primer and downstream primer, the cleavage of PTO and the extension of PTO fragment.

PTO and CTO have no label. PTO and CTO are blocked with a carbon spacer at their 3'-ends. The genomic DNA of *Neisseria gonorrhoeae* (NG) gene was used as a target. HO has a fluorescent reporter molecule (Cal Fluor Red 610) at its 5'-end and has a quencher molecule (BHQ-2) at its 3'-end.

The sequences of upstream primer, downstream primer, PTO, CTO and HO used in this Example are:

```
NG-F-1
                                           (SEQ ID NO: 4)
5'-TACGCCTGCTACTTTCACGCTIIIIIGTAATCAGATG-3'

NG-R-1
                                           (SEQ ID NO: 5)
5'-CAATGGATCGGTATCACTCGCIIIIICGAGCAAGAAC-3'

NG-PTO
                                           (SEQ ID NO: 6)
5'-ACGACGGCTTGGCTGCCCCTCATTGGCGTGTTTC

G[Spacer C3]-3'

NG-CTO-1
                                           (SEQ ID NO: 2)
5'-CATATCGTCCAGGGTATCCAGCGCTCAGCCAAGCCGTCG

T[Spacer C3]-3'

NG-HO-1
                                           (SEQ ID NO: 3)
5'-[Cal Fluor Red 610]GCGCTGGATACCCTG[BHQ-2]-3'
(Underlined letters indicate the 5'-tagging
portion of PTO)
```

2-1. Real-Time Detection at a Pre-Determined Temperature During PCR

The reaction was conducted in the final volume of 20 μl containing 100 pg of genomic DNA of NG, 10 pmole of upstream primer (SEQ ID NO: 4), 10 pmole of downstream primer (SEQ ID NO: 5), 5 pmole of PTO (SEQ ID NO: 6), 0.5 pmole of CTO (SEQ ID NO: 2), 0.5 pmole of HO (SEQ ID NO: 3) and 10 μl of 2× Master Mix [containing 2.5 mM $MgCl_2$, 200 μM of dNTPs and 1.6 units of H-Taq DNA polymerase (Solgent, Korea)]; the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 55° C., and 30 sec at 72° C. Detection of signal was performed at the hybridization step (55° C.) of each cycle at which the CTO-HO hybrid was expected to maintain a double-stranded form. Also, a signal was measured at the denaturation step (95° C.) of each cycle.

The PCE-NH assay comprising real-time detection at a pre-determined temperature employs the fact that the signal from a double strand formed by hybridization of the HO with the CTO is different from the signal from the single stranded HO existing by inhibition of hybridization between the HO with the CTO.

In this Example, the HO has an interactive dual label. When the HO is in a single stranded state, the reporter molecule and the quencher molecule on the HO are conformationally adjacent to each other to allow the quencher molecule to quench the signal from the reporter molecule. Where the target nucleic acid sequence is absent and the CTO/HO hybrid is formed, the reporter molecule and the quencher molecule on the HO are conformationally separated to allow the quencher molecule to unquench the signal from the reporter molecule.

When the target nucleic acid sequence is present, the target-dependent formation of the extended duplex inhibits the hybridization of the HO with the CTO, thereby enabling the HO to be in a single stranded state, resulting in quenching the signal form the reporter molecule. Therefore, the number of the HOs in a single strand is increased upon increasing the number of the extended duplex, and in turn the signal intensity finally detected shows decreased patterns.

Meanwhile, when the target nucleic acid sequence is present, the HO hybridized with the CTO may be cleaved during the extension of the PTO fragment. The cleavage causes the reporter molecule and the quencher molecule to be separated permanently, which results in unquenching perfectly the signal from the reporter molecule. The unquenching extent by cleavage of the HO is larger than the unquenching extent by hybridization of the HO with the CTO. Therefore, where signal provided by cleavage of the HO is detected, the signal intensity shows increased patterns upon increasing the number of the cleaved HOs. The signal provided by cleavage of the HO may be detected at various temperatures. The detection at higher temperatures may remove signals to be provided by hybridization between the HO and CTO.

In this Example, while both situations including the inhibition of hybridization between the intact HO and the CTO and the cleavage of the HO may coexist, the signal pattern may be provided depending on a prevailing situation.

As shown in FIG. 20A, the intensity of fluorescent signal measured at the hybridization step (55° C.) showed the decreasing pattern in the presence of the target. No signal was detected in the absence of the target. This result shows that PCE-NH assay can detect a target nucleic acid sequence in real-time detection manner and further that the inhibition of the hybridization of intact HO to CTO allows detecting the presence of the target sequence by PCE-NH assay.

In addition, to observe the presence of the cleavage of some HOs during the reaction, the detection of signal was also performed at the denaturation step (95° C.) of each cycle during the above reaction. As shown in FIG. 20B, the intensity of fluorescent signal was increased in the presence of the target. No signal was detected in the absence of the target. This result shows that some HOs can be cleaved during the reaction.

2-2. Melting Analysis

After the reaction in Example 2-1, melting curve was obtained by cooling the reaction mixture to 40° C., holding at 40° C. for 10 min, and heating slowly at 40° C. to 85° C. The fluorescence was measured continuously during the temperature rise to monitor dissociation of the CTO-HO hybrid. Melting peak was derived from the melting curve data.

As shown in FIG. 20C, a melting peak at 59.0° C. corresponding to the expected Tm value of the CTO-HO hybrid was detected in the absence of the target. No peak was detected in the presence of the target. This result shows that PCE-NH assay can detect a target nucleic acid sequence in melting analysis manner.

Example 3: Evaluation of PCE-NH Assay Using a Competitive HO for the Detection of a Target Nucleic Acid Sequence We additionally examined whether PCE-NH assay can detect a target nucleic acid sequence by using the signal provided from the inhibition of the hybridization of intact HO to CTO without the signal provided from the cleavage of HO in (i) real-time detection at a pre-determined temperature or (ii) melting analysis manner. To exclude the effect of cleavage of HO during the PTO fragment extension, a competitive HO is designed to compete against the PTO fragment in terms of the hybridization site on CTO. The competitive HO in this Example includes a PTO fragment sequence and an additional sequence, at its 3'-end part, complementary to the templating portion of CTO.

Taq DNA polymerase having a 5' nuclease activity was used for the extension of upstream primer and downstream primer, the cleavage of PTO and the extension of PTO fragment.

PTO and CTO have no label. PTO and CTO are blocked with a carbon spacer at their 3'-ends. The genomic DNA of NG gene was used as a target. The competitive HO has a fluorescent reporter molecule (Cal Fluor Red 610) at its 5'-end and has a quencher molecule (BHQ-2) at its 3'-end.

The sequences of upstream primer, downstream primer, PTO, CTO and competitive HO used in this Example are:

NG-F-2
(SEQ ID NO: 7)
5'-TACGCCTGCTACTTTCACGCT-3'

NG-R-2
(SEQ ID NO: 8)
5'-CAATGGATCGGTATCACTCGC-3'

NG-PTO
(SEQ ID NO: 6)
5'-ACGACGGCTTGGCTGCCCCTCATTGGCGTGTTTC

G[Spacer C3]-3'

NG-CTO-1
(SEQ ID NO: 2)
5'-CATATCGTCCAGGGTATCCAGCGCTCAGCCAAGCCGTCG

T[Spacer C3]-3'

NG-HO-2
(SEQ ID NO: 9)
5'-[Cal Fluor Red 610]ACGACGGCTTGGCTGAGCG

C[BHQ-2]-3'
(Underlined letters indicate the 5'-tagging portion of PTO)

3-1. Real-Time Detection at a Pre-Determined Temperature

The reaction was conducted in the final volume of 20 µl containing 100 pg of genomic DNA of NG, 10 pmole of upstream primer (SEQ ID NO: 7), 10 pmole of downstream primer (SEQ ID NO: 8), 5 pmole of PTO (SEQ ID NO: 6), 0.5 pmole of CTO (SEQ ID NO: 2), 1 pmole of competitive HO (SEQ ID NO: 9) and 10 µl of 2× Master Mix [containing 2.5 mM MgCl$_2$, 200 µM of dNTPs and 1.6 units of H-Taq DNA polymerase (Solgent, Korea)]; the tube containing the reaction mixture was placed in the real-time thermocycler (CFX96, Bio-Rad); the reaction mixture was denatured for 15 min at 95° C. and subjected to 50 cycles of 30 sec at 95° C., 60 sec at 60° C., and 30 sec at 72° C. Detection of the signal was performed at the hybridization step (60° C.) at which the CTO-HO hybrid was expected to maintain a double-stranded form. Also, a signal was measured at the denaturation step (95° C.) of each cycle.

As shown in FIG. 21A, the decreasing pattern of the intensity of the fluorescent signal measured at the hybridization step (60° C.) was obtained in the presence of the target. No signal was detected in the absence of the target.

This result shows that PCE-NH assay can detect a target nucleic acid sequence by using the inhibition of the hybridization of intact HO to CTO without the cleavage of HO.

In addition, to observe the presence of the cleavage of some HOs during the reaction, the detection of signal was also performed at the denaturation step (95° C.) of each cycle during the above reaction. As shown in FIG. 21B, No signal was detected in the presence of the target as well as in the absence of the target. This result shows that the HOs were not cleaved during the reaction.

3-2. Melting Analysis

After the reaction in Example 4-1, melting curve was obtained by cooling the reaction mixture to 55° C., holding at 55° C. for 30 sec, and heating slowly at 55° C. to 85° C. The fluorescence was measured continuously during the temperature rise to monitor dissociation of the CTO-HO hybrid. Melting peak was derived from the melting curve data.

As shown in FIG. 21C, a melting peak at 70.0° C. corresponding to the expected Tm value of the CTO-HO hybrid was detected in the absence of target. No peak was detected in the presence of the target.

This result shows that PCE-NH comprising melting analysis can detect a target nucleic acid sequence by using the inhibition of the hybridization of intact HO to CTO without HO cleavage.

Example 4: Evaluation of PCE-NH Assay Using a Single-Labeled CTO and an Immobilized HO on Microarray We further examined PCE-NH assay using the single-labeled CTO and the immobilized HO on microarray. The cleavage of PTO and the extension of PTO fragment, the hybridization of CTO to immobilized HO were conducted simultaneously on the microarray. After the reaction, the presence or absence of the CTO-HO duplex was analyzed. When the PTO fragment is extended in the presence of the HO, the formation of the hybrid between the CTO and the HO can be prevented by (i) the inhibition of the hybridization between HO and CTO and/or (ii) the cleavage of HO during the extension of the PTO fragment.

Taq DNA polymerase having 5' nuclease activity was used for the extension of upstream primer and downstream primer, the cleavage and the extension of the PTO fragment. PTO is blocked with a carbon spacer at its 3'-end. CTO has a fluorescent reporter molecule (Quasar670) at its 3'-end. HO has poly(T)$_{10}$ as a linker arm and was immobilized on the surface of a glass slide by using an amino group (AminnoC7) at its 3'-end. A marker probe having a fluorescent reporter molecule (Quasar670) at its 5'-end was immobilized on the surface of the glass slide by using an amino group at its 3'-end.

The sequences of upstream primer, downstream primer, PTO, CTO, HO and marker used in this Example are:

NG-F-2
(SEQ ID NO: 7)
5'-TACGCCTGCTACTTTCACGCT-3'

NG-R-2
(SEQ ID NO: 8)
5'-CAATGGATCGGTATCACTCGC-3'

NG-PTO
(SEQ ID NO: 6)
5'-ACGACGGCTTGGCTGCCCCTCATTGGCGTGTTTC

G[C3 spacer]-3'

NG-CTO-2
(SEQ ID NO: 10)
5'-CATATCGTCCAGGGTATCCAGCGCTCAGCCAAGCCGTCG

T[Quasar670]-3'

NG-HO-3
(SEQ ID NO: 11)
5'-GCGCTGGATACCCTGGACGATATGTTTTTTTT

T[Amino C7]-3'

Marker
(SEQ ID NO: 12)
5'-[Quasar67]ATATATATAT[AminoC7]-3'
(Underlined letters indicate the 5'-tagging portion of PTO)

NSB9 NHS slides (NSBPOSTECH, Korea) were used for fabrication of the HO and marker (SEQ ID NOs: 11 and 12). The HO and marker dissolved in NSB spotting buffer at the final concentration of 50 μM were printed on the NSB9 NHS slides with PersonalArrayer™16 Microarray Spotter (CapitalBio, China). The HO and marker were spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound CTO and marker and rinsed with distilled water. Then, the DNA-functionalized slides were dried using a slide centrifuge and stored in dark at 4° C. until use.

The PCE-NH reaction was conducted in the final volume of 30 μl containing 100 pg of genomic DNA of NG gene, 10 pmole of upstream primer (SEQ ID NO: 7), 10 pmole of downstream primer (SEQ ID NO: 8), 5 pmole of PTO (SEQ ID NO: 6), 0.5 pmole of CTO (SEQ ID NO: 10) and 15 μl of 2× Master Mix [containing 2.5 mM MgCl$_2$, 200 μM of dNTPs, and 2.4 units of H-Taq DNA polymerase (Solgent, Korea)]; the whole mixture was applied to a chamber assembled on the surface of NSB glass slide on which the HO (SEQ ID NO: 11) was cross-linked. The slide was placed on in situ block in a thermocycler (GenePro B4I, China). The PCE-NH reaction was carried out as follows: 15 min denaturation at 95° C. and 40 cycles of 30 sec at 95° C., 60 sec at 60° C., 30 sec at 72° C. and 5 min hybridization at 55° C.

After the reaction, the slides were washed in distilled water for 1 min. The image acquisition was carried out by the use of Confocal Laser Scanner, Axon GenePix4300A (Molecular Device, US) with scanning at 5-μm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 22, the fluorescent intensity was apparently decreased in the presence of the target in comparison to that in the absence of the target. This result shows that PCE-NH assay using single-labeled CTO and immobilized HO on microarray can detect a target nucleic acid sequence.

Example 5: Evaluation of PCE-NH Assay Using a Single-Labeled CTO and an Immobilized HO on Microarray without Cleavage of HO We further examined PCE-NH assay using the single-labeled CTO and the immobilized HO on microarray. The cleavage of PTO and the extension of PTO fragment were conducted in a vessel and the resultant was taken into the microarray where the HO was immobilized, which allowed to exclude the cleavage of HO during the PTO fragment extension. After the hybridization reaction, the presence or absence of the CTO-HO duplex was analyzed.

The same Taq DNA polymerase, PTO, CTO, HO and marker were used as Example 4.

Slide preparation was conducted as the same protocol used in Example 4.

The cleavage of PTO and the extension of PTO fragment was conducted in the final volume of 30 μl containing 100 pg of genomic DNA of NG, 10 pmole of upstream primer (SEQ ID NO: 7), 10 pmole of downstream primer (SEQ ID NO: 8), 5 pmole of PTO (SEQ ID NO: 6), 0.5 pmole of CTO (SEQ ID NO: 10) and 15 μl of 2× Master Mix [containing 2.5 mM MgCl$_2$, 200 μM of dNTPs, and 2.4 units of H-Taq DNA polymerase (Solgent, Korea)]; the tube containing the reaction mixture was placed in the real-time thermocycler (CFX96, Bio-Rad); the reaction mixture was denatured for 15 min at 95° C. and subjected to 40 cycles of 30 sec at 95° C., 60 sec at 60° C., 30 sec at 72° C.

The resulting mixture was applied to a chamber assembled on the surface of NSB glass slide on which the HO (SEQ ID NO: 11) was cross-linked. The slide was placed on in situ block in a thermocycler (GenePro B4I, China). The hybridization reaction was allowed for 30 min at 55° C. Finally the slide was washed in distilled water for 1 min. The image acquisition was carried out by the use of Confocal Laser Scanner, Axon GenePix4300A (Molecular Device, US) with scanning at 5 μm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 23, the fluorescent intensity was apparently decreased in the presence of the target in comparison to that in the absence of the target. This result shows that PCE-NH assay using single-labeled CTO and immobilized HO on microarray can detect a target nucleic acid sequence without involving the step of HO cleavage.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence in a nucleic acid sample by a PCE-NH (PTO Cleavage and Extension-Dependent Non-Hybridization) assay, comprising:
   (a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;
   (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;
   (c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;
   (d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;
   (e) performing a melting analysis or a hybridization analysis for the resultant of the step (d) over a range of temperatures with a HO (hybridizing oligonucleotide) comprising a hybridizing nucleotide sequence complementary to the CTO; wherein when the target nucleic acid sequence is not present in the nucleic acid sample, the extended duplex is not formed and the CTO and the HO form a hybrid, thereby providing a signal indicative of the presence of the hybrid between the CTO and the HO; wherein when the target nucleic acid sequence is present in the nucleic acid sample, the extended duplex is formed to prevent the formation of the hybrid between the CTO and the HO, thereby not providing the signal; wherein the signal is provided by (i) a label linked to the HO, (ii) a label linked to the CTO, (iii) a label linked to the HO and a label linked to the CTO, or (iv) an intercalating label; and
   (f) detecting the signal indicative of the presence of the hybrid between the CTO and the HO; wherein the presence of the hybrid between the CTO and the HO indicates the absence of the target nucleic acid sequence; wherein the absence of the hybrid between the CTO and the HO indicates the presence of the target nucleic acid sequence.

2. The method according to claim 1, wherein the step (d) is performed in the presence of the HOs; wherein (i) the fragment hybridized with the capturing portion of the CTO is extended prior to the hybridization of the HO and/or (ii) when the HO is hybridized with the CTO prior to the extension of the fragment, the extension of the fragment cleaves or displaces the HO from the CTO, thereby the formation of the extended duplex prevents the formation of the hybrid between the CTO and the HO in the step (e) due to the inhibition of the hybridization of the HO with the CTO and/or the consumption of the HO by the cleavage.

3. The method according to claim 1, wherein the HO or the CTO has an interactive dual label comprising a reporter molecule and a quencher molecule; wherein the interactive dual label is positioned at a site such that a signal from the interactive dual label in the case of the formation of the hybrid between the CTO and the HO is different from a signal from the interactive dual label in the case of no formation of the hybrid between the CTO and the HO.

4. The method according to claim 1, wherein the HO has one of an interactive dual label comprising a reporter molecule and a quencher molecule and the CTO has the other of the interactive dual label; wherein the interactive dual label is positioned at a site such that a signal from the interactive dual label in the case of the formation of the hybrid between the CTO and the HO is different from a signal from the interactive dual label in the case of no formation of the hybrid between the CTO and the HO.

5. The method according to claim 1, wherein the method is performed using one additional HO comprising a hybridizing nucleotide sequence complementary to the CTO and the two HOs are hybridized with the CTO in an adjacent manner to each other; wherein one of the two HOs has one of an interactive dual label comprising a reporter molecule and a quencher molecule and the other of the two HOs has the other of the interactive dual label; wherein the interactive dual label is positioned at a site such that a signal from the interactive dual label in the case of the formation of the hybrid between the CTO and the two HOs is different from a signal from the interactive dual label in the case of no formation of the hybrid between the CTO and the two HOs.

6. The method according to claim 1, wherein the HO or the CTO has a single label; wherein the single label is positioned at a site such that a signal from the single label in the case of the formation of the hybrid between the CTO and the HO is different from a signal from the single label in the case of no formation of the hybrid between the CTO and the HO.

7. The method according to claim 1, wherein the HO comprises a nucleotide sequence being competitive with the fragment in terms of hybridization with the CTO.

8. The method according to claim 7, wherein the HO is not cleaved by the fragment or its extension product.

9. The method according to claim 1, wherein the PTO, the CTO and/or the HO is blocked at its 3'-end to prohibit its extension.

10. The method according to claim 1, wherein the upstream oligonucleotide is an upstream primer or an upstream probe.

11. The method according to claim 1, wherein the method further comprises repeating all or some of the steps (a)-(f) with denaturation between repeating cycles.

12. The method according to claim 1, wherein the method is performed to detect at least two types of target nucleic acid sequences; wherein the upstream oligonucleotide comprises at least two types of oligonucleotides, the PTO comprises at least two types of the PTOs, the CTO comprises at least two types of the CTOs and the HO comprises at least two types of the HOs.

13. The method according to claim 1, wherein the target nucleic acid sequence comprises a nucleotide variation.

14. The method according to claim 1, wherein the method is performed in the presence of a downstream primer.

15. The method according to claim 1, wherein the method is performed with no use of the upstream oligonucleotide and the cleavage of the PTO in the step (b) occurs with no help of the upstream oligonucleotide or its extended strand.

16. A method for detecting a target nucleic acid sequence in a nucleic acid sample on a solid phase by a PCE-NH (PTO Cleavage and Extension-Dependent Non-Hybridization) assay, comprising:
- (a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;
- (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;
- (c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;
- (d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;
- (e) hybridizing the resultant of the step (d) with a HO (hybridizing oligonucleotide) comprising a hybridizing nucleotide sequence complementary to the CTO under conditions suitable for hybridization between the CTO and the HO; wherein one of the CTO and the HO is labeled with a single label and the other unlabeled is immobilized on a solid substrate or is to become immobilized on a solid substrate before the detection of the signal in the step (f); wherein when the target nucleic acid sequence is not present in the nucleic acid sample, the extended duplex is not formed and the CTO and the HO form the hybrid, thereby providing a signal from the single label on the solid substrate; wherein when the target nucleic acid sequence is present in the nucleic acid sample, the extended duplex is formed to prevent the formation of the hybrid between the CTO and the HO, thereby providing no signal from the single label on the solid substrate; and
- (f) detecting the signal on the solid substrate to detect the hybrid between the CTO and the HO on the solid substrate; wherein the presence of the hybrid between the CTO and the HO indicates the absence of the target nucleic acid sequence; wherein the absence of the hybrid between the CTO and the HO indicates the presence of the target nucleic acid sequence.

17. The method according to claim 16, wherein the step (d) is performed in the presence of the HOs; wherein (i) the fragment hybridized with the capturing portion of the CTO is extended prior to the hybridization of the HO and/or (ii) when the HO is hybridized with the CTO prior to the extension of the fragment, the extension of the fragment cleaves or displaces the HO from the CTO, thereby the formation of the extended duplex prevents the formation of the hybrid between the CTO and the HO in the step (e) due to the inhibition of the hybridization of the HO with the CTO and/or the consumption of the HO by the cleavage.

18. The method according to claim 16, wherein (i) the CTO has the single label and the HO is immobilized on the solid substrate or to become immobilized on a solid substrate before the detection of the signal in the step (f) or (ii) the HO has the single label and the CTO is immobilized on the solid substrate or to become immobilized on a solid substrate before the detection of the signal in the step (f).

19. A method for detecting a target nucleic acid sequence in a nucleic acid sample by a PCE-NH (PTO Cleavage and Extension-Dependent Non-Hybridization) assay, comprising:
- (a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;
- (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;
- (c) hybridizing the fragment released from the PTO with a CTO (Capturing and Templating Oligonucleotide);

wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to produce an extended strand complementary to the templating portion of the CTO and an extended duplex is formed; wherein when the target nucleic acid sequence is not present in the nucleic acid sample, the extended duplex is not formed;

(e) hybridizing the resultant of the step (d) with a HO (hybridizing oligonucleotide) comprising a hybridizing nucleotide sequence complementary to the CTO under conditions suitable for hybridization between the CTO and the HO; wherein when the target nucleic acid sequence is not present in the nucleic acid sample, the extended duplex is not formed and the CTO and the HO form a hybrid, thereby providing a first signal indicative of the presence of the hybrid between the CTO and the HO; wherein when the target nucleic acid sequence is present in the nucleic acid sample, the extended duplex inhibits the hybridization of the HO with the CTO, thereby providing a second signal indicative of the presence of HO unhybridized with CTO; wherein the signals are provided by (i) a label linked to the HO, (ii) a label linked to the CTO, (iii) a label linked to the HO and a label linked to the CTO, or (iv) an intercalating label; and (f) detecting the first signal or the second signal at a predetermined temperature at which the hybrid between the CTO and the HO maintains its double-stranded form; wherein the presence of the hybrid between the CTO and the HO indicates the absence of the target nucleic acid sequence; wherein the absence of the hybrid between the CTO and the HO indicates the presence of the target nucleic acid sequence; wherein the difference in the first signal and the second signal allows to determine the presence or absence of the hybrid between the CTO and the HO to indicate the presence or absence of the target nucleic acid sequence in the nucleic acid sample.

20. The method according to claim 19, wherein the step (d) is performed in the presence of the HOs; wherein (i) the fragment hybridized with the capturing portion of the CTO is extended prior to the hybridization of the HO and/or (ii) when the HO is hybridized with the CTO prior to the extension of the fragment, the extension of the fragment cleaves or displaces the HO from the CTO.

21. The method according to claim 19, wherein the HO or the CTO has an interactive dual label comprising a reporter molecule and a quencher molecule; wherein the interactive dual label is positioned at a site such that a signal from the interactive dual label in the case that the CTO and the HO are associated to form a hybrid is different from a signal from the interactive dual label in the case that the CTO and the HO are dissociated from each other.

22. The method according to claim 19, wherein the HO has one of an interactive dual label comprising a reporter molecule and a quencher molecule and the CTO has the other of the interactive dual label; wherein the interactive dual label is positioned at a site such that a signal from the interactive dual label in the case that the CTO and the HO are associated to form a hybrid is different from a signal from the interactive dual label in the case that the CTO and the HO are dissociated from each other.

23. The method according to claim 19, wherein the method is performed using one additional HO comprising a hybridizing nucleotide sequence complementary to the CTO and the two HOs are hybridized with the CTO in an adjacent manner to each other; wherein one of the two HOs has one of an interactive dual label comprising a reporter molecule and a quencher molecule and the other of the two HOs has the other of the interactive dual label; wherein the interactive dual label is positioned at a site such that a signal from the interactive dual label in the case that the CTO and the two HOs are associated to form a hybrid is different from a signal from the interactive dual label in the case that the CTO and the two HOs are dissociated from each other.

24. The method according to claim 19, wherein the HO or the CTO has a single label; wherein the single label is positioned at a site such that a signal from the single label in the case that the CTO and the HO are associated to form a hybrid is different from a signal from the single label in the case that the CTO and the HO are dissociated from each other.

25. The method according to claim 19, wherein one of the CTO and HO is immobilized on the solid substrate or to become immobilized on a solid substrate before the detection of the signal in the step (f) and the signal is detected on the solid substrate.

* * * * *